United States Patent [19]
Fischer et al.

[11] Patent Number: 6,150,304
[45] Date of Patent: *Nov. 21, 2000

[54] 2-ARYL-CYCLOPENTANE-1,3-DIONE DERIVATIVES

[75] Inventors: Reiner Fischer, Monheim; Jacques Dumas, Köln; Thomas Bretschneider, Lohmar; Christoph Erdelen, Leichlingen; Ulrike Wachendorff-Neumann, Neuwied; Hans-Joachim Santel; Markus Dollinger, both of Leverkusen; Andreas Turberg, Erkrath; Norbert Mencke, Leverkusen, all of Germany

[73] Assignee: Bayer Aktiengesellschaft, Leverkusen, Germany

[ * ] Notice: This patent is subject to a terminal disclaimer.

[21] Appl. No.: 09/131,043

[22] Filed: Aug. 6, 1998

Related U.S. Application Data

[62] Division of application No. 08/765,429, Dec. 31, 1996, Pat. No. 5,840,661.

[30] Foreign Application Priority Data

Jul. 7, 1994 [DE] Germany ............... 44 23 943
Jan. 30, 1995 [DE] Germany .............. 195 02 815
May 23, 1995 [DE] Germany .............. 195 18 962

[51] Int. Cl.⁷ .................. A01N 37/10; A01N 37/34; C07C 255/06
[52] U.S. Cl. ................. 504/309; 504/310; 504/348; 514/520; 558/70; 558/194; 558/423
[58] Field of Search ................ 504/309, 310, 504/348; 558/70, 194, 423; 514/520; 546/194; 549/66; 544/244; 548/201, 369.4, 370.4, 370.7

[56] References Cited

U.S. PATENT DOCUMENTS 5,840,661 11/1998 Fischer et al. ............ 504/348

*Primary Examiner*—Deborah C. Lambkin
*Assistant Examiner*—Ebenezer Sackey
*Attorney, Agent, or Firm*—Norris, McLaughlin & Marcus, P.A.

[57] ABSTRACT

The present invention relates to novel 2-aryl-3-hydroxy-cyclopent-2-en-1-one derivatives of the formula (I)

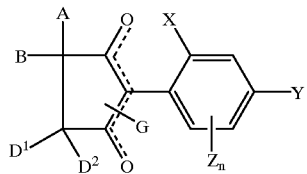

(I)

in which

X represents halogen, nitro, cyano, alkyl, alkoxy, alkenyloxy, alkylthio, alkylsulphinyl, alkylsulphonyl, halogenoalkyl or halogenoalkoxy, Y represents hydrogen, halogen, nitro, cyano, alkyl, alkoxy, alkenyloxy, alkylthio, alkylsulphinyl, alkylsulphonyl, halogenoalkyl or halogenoalkoxy, Z represents halogen, nitro, cyano, alkyl, alkoxy or halogenoalkoxy and A, B, $D^1$, $D^2$, G and n have the meaning given in the description, several processes for their preparation and their use as compositions for controlling pests and as herbicides.

14 Claims, No Drawings

2-ARYL-CYCLOPENTANE-1,3-DIONE DERIVATIVES

This application is a divisional of application Ser. No. 08/765,429, filed on Dec. 31, 1996 (now allowed) now U.S. Pat. No. 5,840,661.

The present invention relates to novel 2-aryl-3-hydroxy-$\Delta^2$-cyclopenten-1-one: derivatives, processes for their preparation and their use as herbicides and pest control agents.

It is known that certain substituted 2-arylcyclopentanediones have herbicidal and acaricidal properties (cf., for example, U.S. Pat. Nos. 4,283,348; 4,338,122; 4,436,666; 4,526,723; 4,551,547 and 4,632,698). Similarly substituted compounds are furthermore known; 3-hydroxy-5,5-dimethyl-2-phenylcyclopent-2-en-1-one from the publication Micklefield et al., Tetrahedron, (1992), 7519-26 and the natural substance involutin, (−)-cis-5-(3,4-dihydroxyphenyl)-3,4-dihydroxy-2-)4-hydroxyphenyl)-cyclopent-2-enone from the publication Edwards et al., J. Chem. Soc. S, (1967), 405–9. No insecticidal or acaricidal action is described.

Novel 2-aryl-3-hydroxy-cyclopent-2-en-1-one derivatives of the formula (I)

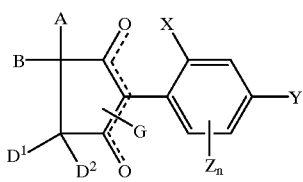

(I)

in which

X represents halogen, nitro, cyano, alkyl, alkoxy, alkenyloxy, alkylthio, alkylsulphinyl, alkylsulphonyl, halogenoalkyl or halogenoalkoxy, Y represents hydrogen, halogen, nitro, cyano, alkyl, alkoxy, alkenyloxy, alkylthio, alkylsulphinyl, alkylsulphonyl, halogenoalkyl or halogenoalkoxy, Z represents halogen, nitro, cyano, alkyl, alkoxy or halogenoalkoxy, n represents an integer from 0 to 3, or wherein the radicals X and Z, together with the phenyl radical to which they are bonded, form the naphthalene radical of the formula

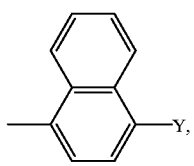

in which

Y has the abovementioned meaning,

A and B independently of one another represent alkyl, alkenyl, alkinyl, alkoxyalkyl, polyalkoxyated or alkylthioalkyl in each case optionally substituted once or several times in an identical or different manner by halogen, or saturated or unsaturated, unsubstituted or substituted cycloalkyl which is optionally interrupted by at least one heteroatom, or phenyl or phenylalkyl, in each case optionally substituted once or several times in an identical or different manner by halogen, alkyl, halogenoalkyl, alkoxy, halogenoalkoxy, cyano or nitro, or A and B, together with the carbon atom to which they are bonded, form a saturated or unsaturated ring which is optionally interrupted by at least one heteroatom and is optionally substituted, or A and B, together with the carbon atom to which they are bonded, form a ring in which two substituents, together with the carbon atoms to which they are bonded, form a saturated or unsaturated ring which is optionally substituted once or several times in an identical or different manner by halogen, alkyl or alkoxy an d can contain oxygen or sulphur, $D^1$ and $D^2$ independently of one another represent hydrogen, halogen or alkyl which is optionally substituted by halogen or optionally substituted phenyl, G represents hydrogen (a), or represents one of the groups (b)

—CO—$R^1$ (c)

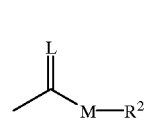

(d)

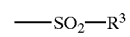
—SO$_2$—$R^3$ (e)

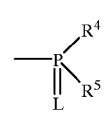

(f)

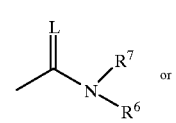
or (g)

E

E represents a metal ion equivalent or an ammonium ion,

L represents oxygen or sulphur,

M represents oxygen or sulphur, $R^1$ represents alkyl, alkenyl, alkoxyalkyl, alkylthioalkyl or polyalkoxyalkyl, in each case optionally substituted once or several times in an identical or different manner by halogen, or optionally substituted, saturated or unsaturated cycloalkyl, which can be interrupted by at least one heteroatom, or represents in each case optionally substituted phenyl, phenylalkyl, hetaryl, phenoxyalkyl or hetaryloxyalkyl, $R^2$ represents alkyl, alkenyl, alkoxyalkyl or polyalkoxyalkyl, in each case optionally substituted once or several times in an identical or different manner by halogen, or in each case optionally substituted cycloalkyl, phenyl or benzyl, $R^3$ represents alkyl which is in each case optionally substituted once or several times in an identical or different manner by halogen, or represents in each case optionally substituted phenyl or phenylalkyl, R⁴ and R⁵ independently of one another represent alkyl, alkoxy, alkylamino, alkenylamino, dialkylamino, dialkenylamino, alkylthio, alkenylthio, alkinylthio or cycloalkylthio, in each case optionally substituted once or several times in an identical or different manner by halogen, or represent in each case optionally substituted phenyl, phenoxy or phenylthio, R⁶ and R⁷ independently of one another represent hydrogen or alkyl, alkenyl, alkoxy or alkoxyalkyl, in each case optionally substituted once or several times in an identical or different manner by halogen, or represent optionally substituted phenyl or optionally substituted benzyl, or R⁶ and R⁷ together represent an alkylene radical which is optionally interrupted by oxygen or sulphur, and the enantiomerically pure forms of compounds of the formula (I) have now been found.

Depending on the position of the substituent G, the compounds of the formula (I) can be present in the two isomeric forms of the formula I-A and I-B

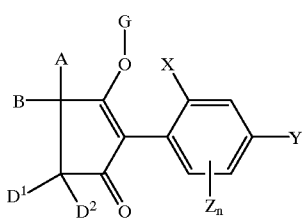

I-A

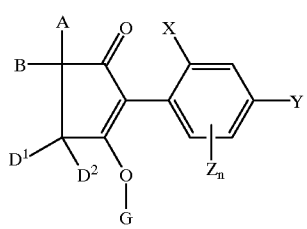

I-B which the broken line in the formula (I) is intended to illustrate.

The compounds of the formulae I-A and I-B can be present both as mixtures and in the form of their pure isomers. If appropriate, mixtures of the compounds of the formulae I-A and I-B can be separated by physical methods, for example by chromatographic methods.

For reasons of better clarity, in the following in each case only one of the possible isomers is shown. This does not exclude the possibility that the compounds, where appropriate, are present in the form of the isomer mixtures or in the other respective isomeric form.

Incorporating the various meanings (a), (b), (c), (d), (e), (f) and (g) of the group G, the following main structures (Ia) to (Ig) result:

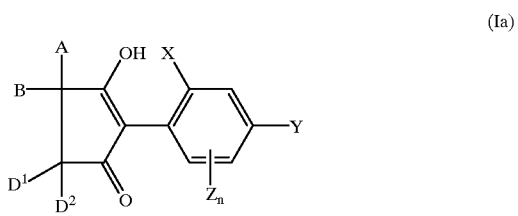

(Ia)

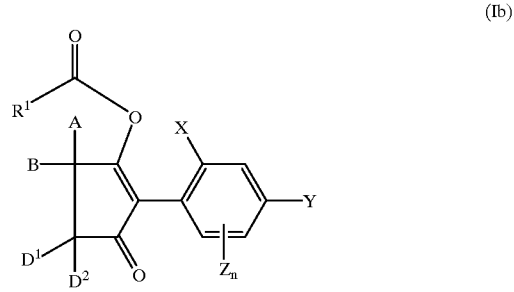

(Ib)

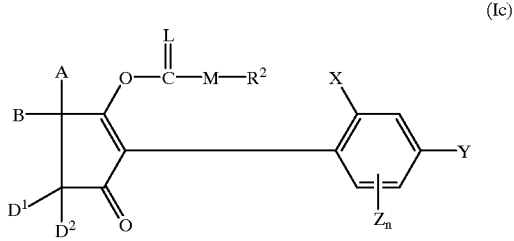

(Ic)

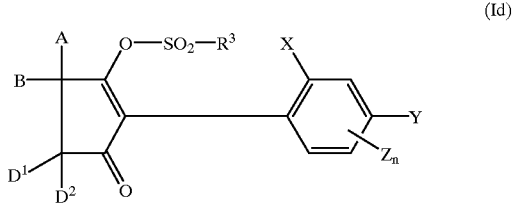

(Id)

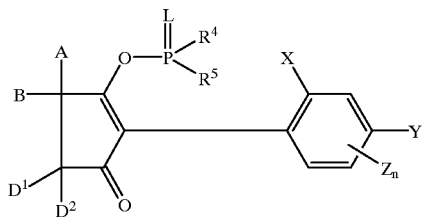
(Ie)

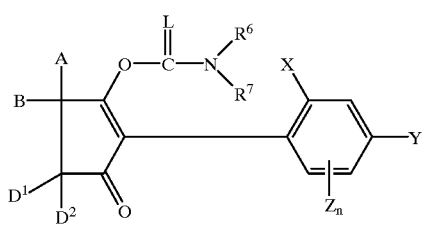
(If)

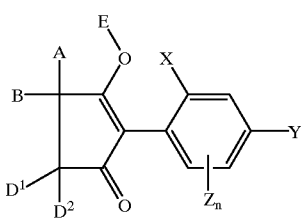
(Ig)

wherein

A, B, D$^1$, D$^2$, E, L, M, X, Y, Z, R$^1$, R$^2$, R$^3$, R$^4$, R$^5$, R$^6$, R$^7$ and n have the abovementioned meanings.

It has furthermore been found (A) that compounds of the formula (Ia)

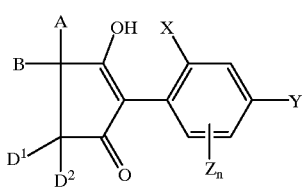
(Ia)

in which

A, B, D$^1$, D$^2$, X, Y, Z and n have the abovementioned meaning, are obtained when ketocarboxylic acid esters of the formula (II)

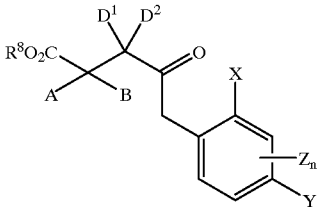
(II)

in which

A, B, D$^1$, D$^2$, X, Y, Z and n have the abovementioned meaning and

R$^8$ represents alkyl (in particular $C_1$–$C_8$-alkyl), are subjected to intermolecular cyclization, if appropriate in the presence of a diluent and in the presence of a base, and (B) that compounds of the formula (Ib)

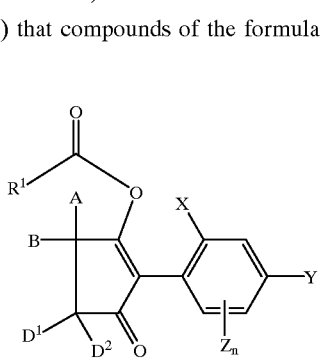
(Ib)

in which

A, B, D$^1$, D$^2$, X, Y, Z, R$^1$ and n have the abovementioned meaning, are obtained when compounds of the formula (Ia)

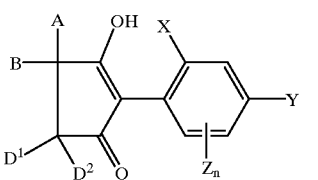
(Ia)

in which

A, B, D$^1$, D$^2$, X, Y, Z and n have the abovementioned meaning,

α) are reacted with acid halides of the formula (III)

(III)

in which

R$^1$ has the abovementioned meaning and

Hal represents halogen (in particular chlorine or bromine), if appropriate in the presence of a diluent and if appropriate in the presence of an acid-binding agent, or β) are reacted with carboxylic acid anhydrides of the formula (IV)

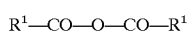  (IV)

in which
  $R^1$ has the abovementioned meaning,
if appropriate in the presence of a diluent and if appropriate in the presence of an acid-binding agent, and (C) that compounds of the formula (Ic)

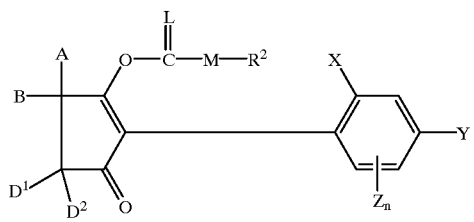  (Ic)

in which
  A, B, $D^1$, $D^2$, X, Y, Z, $R^2$ and n have the abovementioned meaning,
  L represents oxygen and
  M represents oxygen or sulphur,
are obtained when compounds of the formula (Ia)

(Ia)

in which
  A, B, $D^1$, $D^2$, X, Y, Z and n have the abovementioned meaning,
are reacted with a chloroformic acid ester or chloroformic acid thiol ester of the formula (V)

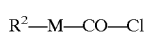  (V)

in which
  $R^2$ and M have the abovementioned meaning,
if appropriate in the presence of a diluent and if appropriate in the presence of an acid-binding agent, and (D) that compounds of the formula (Ic)

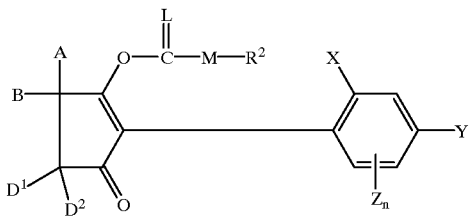  (Ic)

in which
  A, B, $D^1$, $D^2$, $R^2$, X, Y, Z and n have the abovementioned meaning,
  L represents sulphur and
  M represents oxygen or sulphur,
are obtained when compounds of the formula (Ia)

(Ia)

in which
  A, B, $D^1$, $D^2$, X, Y, Z and n have the abovementioned meaning,
  α) are reacted with a chloromonothioformic acid ester or chlorodithioformic acid ester of the formula (VI)

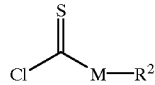  (VI)

in which
  M and $R^2$ have the abovementioned meaning,
if appropriate in the presence of a diluent and if appropriate in the presence of an acid-binding agent, or β) are reacted with carbon disulphide and then with alkyl halides of the formula (VII)

$R^2$—Hal  (VII)

in which
  $R^2$ has the abovementioned meaning
and
  Hal represents chlorine, bromine or iodine,
if appropriate in the presence of a diluent and if appropriate in the presence of a base, and (E) that compounds of the formula (Id)

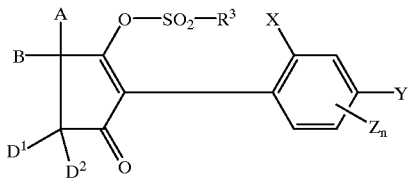 (Id)

in which

A, B, $D^1$, $D^2$, X, Y, Z, $R^3$ and n have the abovementioned meaning, are obtained when compounds of the formula (Ia)

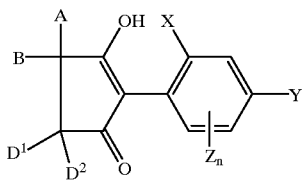 (Ia)

in which

A, B, $D^1$, $D^2$, X, Y, Z and n have the abovementioned meaning, are reacted with sulphonic acid chlorides of the formula (VIII)

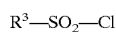

$R^3$—$SO_2$—Cl (VIII)

in which $R^3$ has the abovementioned meaning, if appropriate in the presence of a diluent and if appropriate in the presence of an acid-binding agent, and (F) that compounds of the formula (Ie)

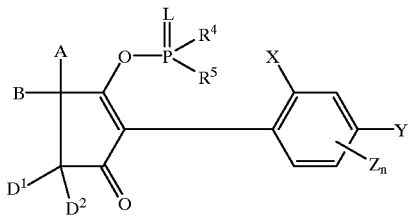 (Ie)

in which

A, B, $D^1$, $D^2$, L, X, Y, Z, $R^4$, $R^5$ and n have the abovementioned meaning, are obtained when compounds of the formula (Ia)

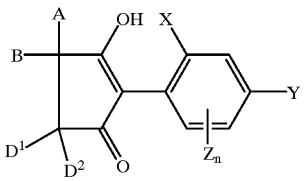 (Ia)

in which

A, B, $D^1$, $D^2$, X, Y, Z and n have the abovementioned meaning, are reacted with phosphorus compounds of the formula (IX)

 (IX)

in which

L, $R^4$ and $R^5$ have the abovementioned meaning and Hal represents halogen (in particular chlorine or bromine), if appropriate in the presence of a diluent and if appropriate in the presence of an acid-binding agent, and (G) that compounds of the formula (If)

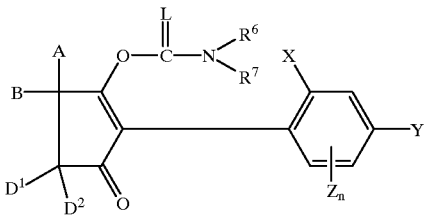 (If)

in which

A, B, $D^1$, $D^2$, L, X, Y, Z, $R^6$, $R^7$ and n have the abovementioned meaning, are obtained when compounds of the formula (Ia)

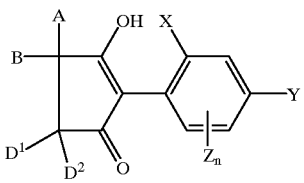 (Ia)

in which

A, B, $D^1$, $D^2$, X, Y, Z and n have the abovementioned meaning,

α) are reacted with isocyanates or isothiocyanates of the formula (X)

$R^6$—N=C=L (X)

in which

R$^6$ and L have the abovementioned meaning,
if appropriate in the presence of a diluent and if appropriate in the presence of a catalyst or β) are reacted with carbamic acid chlorides or thiocarbamic acid chlorides of the formula (XI)

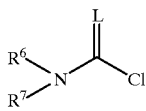
(XI)

in which

L, R$^6$ and R$^7$ have the abovementioned meaning,
if appropriate in the presence of a diluent and if appropriate in the presence of an acid-binding agent, and (H) that compounds of the formula (Ig)

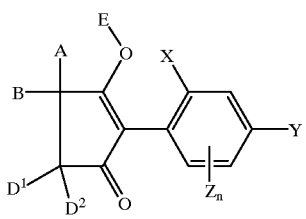
(Ig)

in which

X, Y, D$^1$, D$^2$, Z, A, B and n have the abovementioned meaning, and

E represents a metal ion equivalent (in particular an alkali metal or alkaline earth metal, such as lithium, sodium, potassium, magnesium or calcium) or an ammonium ion, are obtained when compounds of the formula (Ia)

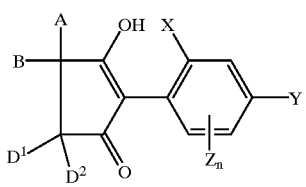
(Ia)

in which

X, Y, Z, A, B, D$^1$, D$^2$ and n have the abovementioned meaning, are reacted with metal compounds of the formula (XII) or amines of the formula (XIII)

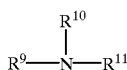
(XIII)

in which

Me represents mono- or divalent metal ions (as mentioned above for E) and t represents the number 1 or 2 and R$^9$, R$^{10}$ and R$^{11}$ independently of one another represent hydrogen, alkyl (preferably C$_1$–C$_8$-alkyl), alkoxy (preferably C$_1$–C$_8$-alkoxy) or hydroxyl, if appropriate in the presence of a diluent.

It has furthermore been found that the novel 2-aryl-3-hydroxy-Δ$^2$-cyclopentenone derivatives of the formula (I) are distinguished by outstanding herbicidal, acaricidal and insecticidal actions.

Formula (I) provides a general definition of the compounds according to the invention.

Preferred substituents and ranges of the radicals listed in the formulae mentioned above and below are explained in the following.

X preferably represents halogen, nitro, cyano, C$_1$–C$_6$-alkyl, C$_1$–C$_6$-alkoxy, C$_3$–C$_6$-alkenyloxy, C$_1$–C$_6$-alkylthio, C$_1$–C$_6$-alkylsulphinyl, C$_1$–C$_6$-alkylsulphonyl, C$_1$–C$_3$-halogenoalkyl or C$_1$–C$_3$-halogenoalkoxy.

Y preferably represents hydrogen, halogen, nitro, cyano, C$_1$–C$_6$-alkyl, C$_1$–C$_6$-alkoxy, C$_3$–C$_6$-alkenyloxy, C$_1$–C$_6$-alkylthio, C$_1$–C$_6$-alkylsulphinyl, C$_1$–C$_6$-alkylsulphonyl, C$_1$–C$_3$-halogenoalkyl or C$_1$–C$_3$-halogenoalkoxy.

Z preferably represents halogen, nitro, cyano, C$_1$–C$_6$-alkyl, C$_1$–C$_6$-alkoxy or C$_1$–C$_3$-halogenoalkoxy.

n preferably represents 0, 1, 2 or 3, or the radicals X and Z, together with the phenyl radical to which they are bonded, preferably represent the naphthalene radical of the formula

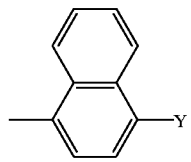

in which

Y has the abovementioned meaning.

A and B independently of one another preferably represent C$_1$–C$_{12}$-alkyl, C$_3$–C$_8$-alkenyl, C$_3$–C$_8$-alkinyl, C$_1$–C$_{10}$-alkoxy-C$_1$–C$_8$-alkyl, poly-C$_1$–C$_8$-alkoxy-C$_1$–C$_8$-alkyl or C$_1$–C$_{10}$-alkylthio-C$_1$–C$_8$-alkyl, in each case optionally substituted once or several times in an identical or different manner by halogen, or saturated or unsaturated cycloalkyl which has 3 to 8 ring atoms, is optionally substituted once or several times in an identical or different manner by halogen, C$_1$–C$_6$-alkyl or C$_1$–C$_6$-alkoxy and in which at least one methylene group is optionally replaced by oxygen and/or sulphur, or phenyl or phenyl-C$_1$–C$_6$-alkyl, in each case optionally substituted once or several times in an identical or different manner by halogen, C$_1$–C$_6$-alkyl, C$_1$–C$_6$-halogenoalkyl, C$_1$–C$_6$-alkoxy, C$_1$–C$_6$-halogenoalkoxy, cyano or nitro, or A and B, together with the carbon atom to which they are bonded, preferably form a saturated or unsaturated 3- to 8-membered ring which optionally contains oxygen and/or sulphur and is optionally substituted once or several times in an identical or different manner by halogen, C$_1$–C$_6$-alkyl, C$_1$–C$_6$-alkoxy, C$_1$–C$_4$-halogenoalkyl, C$_1$–C$_4$-halogen alkoxy, C$_1$–C$_4$-alkylthio or phenyl which is optionally substituted by halogen, C$_1$–C$_6$-alkyl or C$_1$–C$_6$-alkoxy, or A and B, together with the carbon atom to which they are bonded, preferably represent C$_3$–C$_8$-cycloalkyl, in which two substituents, together with the carbon atoms to which they are bonded, represent a saturated or unsaturated 5- to 7-membered ring which is optionally substituted once or several times in an identical or different manner by halogen, $C_1$–$C_6$-alkyl or $C_1$–$C_6$-alkoxy and can contain oxygen or sulphur.

$D^1$ and $D^2$ independently of one another preferably represent hydrogen, halogen or $C_1$–$C_6$-alkyl which is optionally substituted once or several times in an identical or different manner by halogen, or represent phenyl which is optionally substituted once or several times in an identical or different manner by halogen, $C_1$–$C_6$-alkyl, $C_1$–$C_6$-alkoxy, nitro, $C_1$–$C_6$-halogenoalkyl or $C_1$–$C_6$-halogenoalkoxy.

G preferably represents hydrogen (a), or represents one of the groups (b)
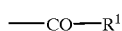

(c)
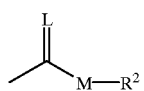

(d)

(e)
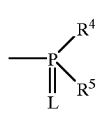

(f)
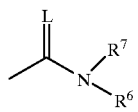

or (g)

E in which

E represents a metal ion equivalent or an ammonium ion,

L represents oxygen or sulphur and

M represents oxygen or sulphur.

$R^1$ preferably represents $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl or poly-$C_1$–$C_8$-alkoxy-$C_2$–$C_8$-alkyl, in each case optionally substituted once or several times in an identical or different manner by halogen, or saturated or unsaturated cycloalkyl having 3 to 8 ring atoms, which is optionally substituted once or several times in an identical or different manner by halogen, $C_1$–$C_6$-alkyl or $C_1$–$C_6$-alkoxy and in which at least one methylene group can be replaced by an oxygen and/or sulphur atom, or represents phenyl which is optionally substituted once or several times in an identical or different manner by halogen, nitro, cyano, $C_1$–$C_6$-alkyl, $C_1$–$C_6$-alkoxy, $C_1$–$C_6$-halogenoalkyl or $C_1$–$C_6$-halogenoalkoxy, or represents phenyl-$C_1$–$C_6$-alkyl which is optionally substituted once or several times in an identical or different manner by halogen, $C_1$–$C_6$-alkyl, $C_1$–$C_6$-alkoxy, $C_1$–$C_6$-halogenoalkyl or $C_1$–$C_6$-halogenoalkoxy, or represents hetaryl which has 5 or 6 ring atoms and is optionally substituted once or several times in an identical or different manner by halogen or $C_1$–$C_6$-alkyl, or represents phenoxy-$C_1$–$C_6$-alkyl which is optionally substituted once or several times in an identical or different manner by halogen or $C_1$–$C_6$-alkyl, or represents hetaryloxy-$C_1$–$C_6$-alkyl which has 5 or 6 ring atoms and is optionally substituted once or several times in an identical or different manner by halogen, amino or $C_1$–$C_6$-alkyl.

$R^2$ preferably represents $C_1$–$C_{20}$-alkyl, $C_2$–$C_{20}$-alkenyl, $C_1$–$C_8$-alkoxy-$C_2$–$C_8$-alkyl or poly-$C_1$–$C_8$-alkoxy-$C_2$–$C_8$-alkyl, in each case optionally substituted once or several times in an identical or different manner by halogen, or represents $C_3$–$C_8$-cycloalkyl which is optionally substituted once or several times in an identical or different manner by halogen, $C_1$–$C_6$-alkyl or $C_1$–$C_6$-alkoxy, or represents phenyl or benzyl, in each case optionally substituted once or several times in an identical or different manner by halogen, nitro, cyano, $C_1$–$C_6$-alkyl, $C_1$–$C_6$-alkoxy or $C_1$–$C_6$-halogenoalkyl.

$R^3$ preferably represents $C_1$–$C_{12}$-alkyl in each case optionally substituted once or several times in an identical or different manner by halogen, or represents phenyl or phenyl-$C_1$–$C_4$-alkyl, in each case optionally substituted once or several times in an identical or different manner by halogen, $C_1$–$C_6$-alkyl, $C_1$–$C_6$-alkoxy, $C_1$–$C_3$-halogenoalkyl, $C_1$–$C_3$-halogenoalkoxy, cyano or nitro.

$R^4$ and $R^5$ independently of one another preferably represent $C_1$–$C_8$-alkyl, $C_1$–$C_8$-alkoxy, $C_1$–$C_8$-alkylamino, $C_3$–$C_8$-alkenylamino, di-($C_1$–$C_8$-alkyl)-amino, di-($C_3$–$C_8$-alkenyl)-amino, $C_1$–$C_8$-alkylthio, $C_3$–$C_5$-alkenylthio, $C_3$–$C_5$-alkinylthio or $C_3$–$C_7$-cycloalkylthio, in each case optionally substituted once or several times in an identical or different manner by halogen, or represent phenyl, phenoxy or phenylthio, in each case optionally substituted once or several times in an identical or different manner by halogen, nitro, cyano, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkyl or $C_1$–$C_4$-halogenoalkyl.

$R^6$ and $R^7$ independently of one another preferably represent hydrogen, or represent $C_1$–$C_{10}$-alkyl, $C_1$–$C_{10}$-alkoxy, $C_3$–$C_8$-alkenyl or $C_1$–$C_{10}$-alkoxy-$C_1$–$C_{10}$-alkyl, in each case optionally substituted once or several times in an identical or different manner by halogen, or represent phenyl which is optionally substituted once or several times in an identical or different manner by halogen, $C_1$–$C_3$-halogenoalkyl, $C_1$–$C_8$-alkyl or $C_1$–$C_8$-alkoxy, or represent benzyl which is optionally substituted once or several times in an identical or different manner by halogen, $C_1$–$C_8$-alkyl, $C_1$–$C_8$-halogenoalkyl or $C_1$–$C_8$-alkoxy, or together represent a $C_2$–$C_6$-alkylene radical, in which a methylene group can be replaced by oxygen or sulphur.

X particularly preferably represents fluorine, chlorine, bromine, nitro, cyano, $C_1$–$C_4$-alkyl, $C_1$–$C_4$-alkoxy, $C_1$–$C_2$-halogenoalkyl or $C_1$–$C_2$-halogenoalkoxy.

Y particularly preferably represents hydrogen, fluorine, chlorine, bromine, nitro, cyano, $C_1$–$C_6$-alkyl, $C_1$–$C_6$-alkoxy, $C_1$–$C_2$-halogenoalkyl or $C_1$–$C_2$-halogenoalkoxy.

Z particularly preferably represents fluorine, chlorine, bromine, nitro, cyano, $C_1$–$C_4$-alkyl, $C_1$–$C_4$-alkoxy or $C_1$–$C_2$-halogenoalkoxy.

n particularly preferably represents 0, 1 or 2.

A and B independently of one another particularly preferably represent $C_1$–$C_{10}$-alkyl, $C_3$–$C_6$-alkenyl, $C_3$–$C_6$-alkinyl, $C_1$–$C_8$-alkoxy-$C_1$–$C_6$-alkyl, poly-$C_1$–$C_6$-alkoxy-$C_1$–$C_6$-alkyl, $C_1$–$C_8$-alkylthio-$C_1$–$C_6$-alkyl, in each case optionally substituted once to five times in an identical or different manner by fluorine or chlorine, or saturated or unsaturated cycloalkyl which has 3 to 7 ring atoms, is optionally substituted once to three times in an identical or different manner by fluorine, chlorine, $C_1$–$C_4$-alkyl or $C_1$–$C_4$-alkoxy, and in which one or two methylene groups are optionally replaced by oxygen and/or sulphur atoms, or phenyl or phenyl-$C_1$–$C_4$-alkyl, in each case optionally substituted once to three times in an identical or different manner by fluorine, chlorine, bromine, $C_1$–$C_4$-alkyl, $C_1$–$C_4$-halogenoalkyl, $C_1$–$C_4$-alkoxy, cyano or nitro, or A and B, together with the carbon atom to which they are bonded, particularly preferably form a saturated or unsaturated 3 to 7-membered ring which optionally contains oxygen and/or sulphur and is optionally substituted once to three times in an identical or different manner by fluorine, chlorine, $C_1$–$C_5$-alkyl, $C_1$–$C_5$-alkoxy, $C_1$–$C_3$-halogenoalkyl, $C_1$–$C_4$-halogenoalkoxy, $C_1$–$C_3$-alkylthio or phenyl which is optionally substituted once or several times in an identical or different manner by fluorine, chlorine, bromine, $C_1$–$C_4$-alkyl or $C_1$–$C_4$-alkoxy, or A and B, together with the carbon atom to which they are bonded, particularly preferably represent $C_4$–$C_7$-cycloalkyl, in which two substituents, together with the carbon atoms to which they are bonded, represent a saturated or unsaturated 5- or 6-membered ring which is optionally substituted once to three times in an identical or different manner by fluorine, chlorine, $C_1$–$C_3$-alkyl or $C_1$–$C_3$-alkoxy and can contain oxygen or sulphur.

$D^1$ and $D^2$ independently of one another particularly preferably represent hydrogen, fluorine, chlorine or $C_1$–$C_4$-alkyl which is optionally substituted once to five times in an identical or different manner by fluorine or chlorine, or represent phenyl which is optionally substituted once to three times in an identical or different manner by fluorine, chlorine, bromine, $C_1$–$C_4$-alkyl, $C_1$–$C_4$-alkoxy, nitro, $C_1$–$C_2$-halogenoalkyl or $C_1$–$C_2$-halogenoalkoxy.

G particularly preferably represents hydrogen (a), or represents one of the groups (b)

—CO—$R^1$ (c)

(d)

—SO$_2$—$R^3$ (e)

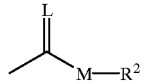

(f)

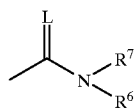

or E (g)

in which

E represents a metal ion equivalent or an ammonium ion,

L represents oxygen or sulphur and

M represents oxygen or sulphur.

$R^1$ particularly preferably represents $C_1$–$C_{16}$-alkyl, $C_2$–$C_{16}$-alkenyl, $C_1$–$C_6$-alkoxy-$C_1$–$C_6$-alkyl, $C_1$–$C_6$-alkylthio-$C_1$–$C_6$-alkyl or poly-$C_1$–$C_6$-alkoxy-$C_2$–$C_6$-alkyl, in each case optionally substituted once to nine times in an identical or different manner by halogen, or cycloalkyl which has 3 to 7 ring atoms, and is optionally substituted once or six times in an identical or different manner by fluorine, chlorine, $C_1$–$C_4$-alkyl or $C_1$–$C_4$-alkoxy, and in which one or two methylene groups are optionally replaced by oxygen and/or sulphur atoms, or represents phenyl which is optionally substituted once to three times in an identical or different manner by fluorine, chlorine, bromine, nitro, cyano, $C_1$–$C_4$-alkyl, $C_1$–$C_4$-alkoxy, $C_1$–$C_3$-halogenoalkyl or $C_1$–$C_3$-halogenoalkoxy, or represents phenyl-$C_1$–$C_4$-alkyl which is optionally substituted once to three times in an identical or different manner by fluorine, chlorine, bromine, $C_1$–$C_4$-alkyl, $C_1$–$C_4$-alkoxy, $C_1$–$C_3$-halogenoalkyl or $C_1$–$C_3$-halogenoalkoxy, or represents pyridyl, thienyl, furanyl, pyrimidyl, thiazolyl or pyrazolyl, in each case optionally substituted once or twice in an identical or different manner by fluorine, chlorine or $C_1$–$C_6$-alkyl, or represents phenoxy-$C_1$–$C_5$-alkyl which is optionally substituted once to three times in an identical or different manner by fluorine, chlorine, bromine or $C_1$–$C_4$-alkyl, or represents pyridyloxy-$C_1$–$C_5$-alkyl, pyrimidyloxy-$C_1$–$C_5$-alkyl or thiazolyloxy-$C_1$–$C_5$-alkyl, in each case optionally substituted once or twice in an identical or different manner by fluorine, chlorine, bromine, amino or $C_1$–$C_4$-alkyl.

$R^2$ particularly preferably represents $C_1$–$C_{16}$-alkyl, $C_2$–$C_{16}$-alkenyl, $C_1$–$C_6$-alkoxy-$C_2$–$C_6$-alkyl or poly-$C_1$–$C_6$-alkoxy-$C_2$–$C_6$-alkyl, in each case optionally substituted once to nine times in an identical or different manner by fluorine or chlorine, or represents $C_3$–$C_7$-cycloalkyl which is optionally substituted once to five times in an identical or different manner by fluorine, chlorine, $C_1$–$C_4$-alkyl or $C_1$–$C_4$-alkoxy, or represents phenyl or benzyl, in each case optionally substituted once to three times in an identical or different manner by fluorine, chlorine, bromine, nitro, cyano, $C_1$–$C_4$-alkyl, $C_1$–$C_3$-alkoxy or $C_1$–$C_3$-halogenoalkyl.

$R^3$ particularly preferably represents $C_1$–$C_8$-alkyl in each case optionally substituted once to five times in an identical or different manner by fluorine or chlorine, or represents phenyl or phenyl-$C_1$–$C_2$-alkyl, in each case optionally substituted once to three times in an identical or different manner by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro.

$R^4$ and $R^5$ independently of one another particularly preferably represent $C_1$–$C_6$-alkyl, $C_1$–$C_6$-alkoxy, $C_1$–$C_6$-alkylamino, $C_3$–$C_6$-alkenylamino, di-($C_1$–$C_6$-alkyl)-amino, di-($C_3$–$C_6$-alkenyl)-amino, $C_1$–$C_6$-alkylthio, $C_3$–$C_4$-alkenylthio, $C_3$–$C_4$-alkinylthio or $C_3$–$C_6$-cycloalkylthio, in each case optionally substituted once to five times in an identical or different manner by fluorine or chlorine, or represent phenyl, phenoxy or phenylthio, in each case optionally substituted once to three times in an identical or different manner by fluorine, chlorine, bromine, nitro, cyano, $C_1$–$C_3$-alkoxy, $C_1$–$C_3$-halogenoalkoxy, $C_1$–$C_3$-alkylthio, $C_1$–$C_3$-halogenoalkylthio, $C_1$–$C_3$-alkyl or $C_1$–$C_3$-halogenoalkyl.

$R^6$ and $R^7$ independently of one another particularly preferably represent hydrogen, or represent $C_1$–$C_6$-alkyl, $C_1$–$C_6$-alkoxy, $C_3$–$C_6$-alkenyl or $C_1$–$C_6$-alkoxy-$C_1$–$C_6$-alkyl, in each case optionally substituted once to five times in an identical or different manner by fluorine or chlorine, or represent phenyl which is optionally substituted once to three times in an identical or different manner by fluorine, chlorine, $C_1$–$C_3$-halogenoalkyl, $C_1$–$C_3$-alkyl or $C_1$–$C_3$-alkoxy, or represent benzyl which is optionally substituted once to three times in an identical or different manner by fluorine, chlorine, $C_1$–$C_3$-alkyl, $C_1$–$C_3$-halogenoalkyl or $C_1$–$C_3$-alkoxy, or together represent a $C_4$–$C_6$-alkylene radical, in which a methylene group can be replaced by oxygen or sulphur.

X especially preferably represents fluorine, chlorine, bromine, nitro, cyano, methyl, ethyl, n-propyl, i-propyl, methoxy, ethoxy, tirfluoromethyl, trifluoromethoxy, difluoromethoxy or chlorodifluoromethoxy.

Y especially preferably represents hydrogen, fluorine, chlorine, bromine, nitro, cyano, methyl, ethyl, n-propyl, i-propyl, n-butyl, i-butyl, tert-butyl, methoxy, ethoxy, trifluoromethyl, trifluoromethoxy, difluoromethoxy or chlorodifluoromethoxy.

Z especially preferably represents fluorine, chlorine, bromine, nitro, cyano, methyl, ethyl, n-propyl, i-propyl, n-butyl, i-butyl, tert-butyl, methoxy, ethoxy, trifluoromethoxy, difluoromethoxy or chlorodifluoromethoxy.

n especially preferably represents 0 or 1.

A and B independently of one another especially preferably represent $C_1$–$C_8$-alkyl. $C_3$–$C_4$-alkenyl, $C_3$–$C_4$-alkinyl, $C_1$–$C_6$-alkoxy-$C_1$–$C_4$-alkyl, poly-$C_1$–$C_4$-alkoxy-$C_1$–$C_4$-alkyl or $C_1$–$C_6$-alkylthio-$C_1$–$C_4$-alkyl, in each case optionally substituted once to three times in an identical or different manner by fluorine or chlorine, or cycloalkyl which has 3 to 6 ring atoms, is, optionally substituted once or twice in an identical or different manner by, fluorine, chlorine, methyl, ethyl, methoxy or ethoxy, and in which one or two methylene groups are optionally replaced by oxygen and/or sulphur atoms, or phenyl or benzyl, in each case optionally substituted once or twice in an identical or different manner by fluorine, chlorine, methyl, ethyl, propyl, iso-propyl, methoxy, ethoxy, trifluoromethyl, cyano or nitro, or A and B, together with the carbon atom to which they are bonded, especially preferably form a saturated or unsaturated 3- to 6-membered ring which optionally contains oxygen and/or sulphur and is optionally substituted once or twice in an identical or different manner by fluorine, chlorine, $C_1$–$C_4$-alkyl, $C_1$–$C_4$-alkoxy, trifluoromethyl, $C_1$–$C_2$-alkylthio or phenyl which is optionally substituted once or twice in an identical or different manner by fluorine, chlorine, methyl or methoxy, or A and B, together with the carbon atom to which they are bonded, especially preferably represent $C_5$–$C_6$-cycloalkyl, in which two substituents, together with the carbon atoms to which they are bonded, represent a saturated or unsaturated 5- or 6-membered ring which is optionally substituted once or twice in an identical or different manner by fluorine, chlorine, methyl, ethyl, methoxy or ethoxy and can contain oxygen or sulphur.

$D^1$ and $D^2$ independently of one another especially preferably represent hydrogen, fluorine, chlorine, methyl or ethyl, or represent phenyl which is optionally substituted once or twice in an identical or different manner by fluorine, chlorine, methyl, methoxy or trifluoromethyl.

G especially preferably represents hydrogen (a), or represents one of the groups (b)

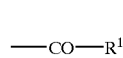

(c)

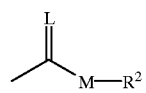

(d)

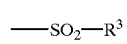

(e)

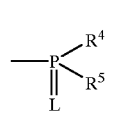

(f)

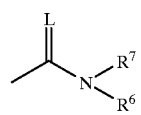

(g)

or E in which

E represents a metal ion equivalent or an ammonium ion,

L represents oxygen or sulphur and

M represents oxygen or sulphur.

$R^1$ especially preferably represents $C_1$–$C_{14}$-alkyl, $C_2$–$C_{14}$-alkenyl, $C_1$–$C_4$ alkoxy-$C_1$–$C_6$-alkyl, $C_1$–$C_4$-alkylthio-$C_1$–$C_6$-alkyl or poly-$C_1$–$C_4$-alkoxy-$C_2$–$C_4$-alkyl, in each case optionally substituted once to three times in an identical or different manner by fluorine or chlorine, or cycloalkyl which has 3 to 6 ring atoms, is optionally substituted once or twice in an identical or different manner by fluorine, chlorine, methyl, ethyl, methoxy or ethoxy, and in which one or two methylene groups are optionally replaced by oxygen and/or sulphur atoms, or represents phenyl which is optionally substituted once or twice in an identical or different manner by fluorine, chlorine, bromine, methyl, ethyl, propyl, i-propyl, methoxy, ethoxy, trifluoromethyl, trifluoromethoxy, cyano or nitro, or represents phenyl-$C_1$–$C_3$-alkyl, in particular benzyl which is optionally substituted once or twice in an identical or different manner by fluorine, chlorine, bromine, methyl, ethyl, propyl, i-propyl, methoxy, ethoxy, trifluoromethyl or trifluoromethoxy, or represents pyridyl, thienyl or furanyl, in each case optionally substituted once or twice in an identical or different manner by fluorine, chlorine, methyl or ethyl, or represents phenoxy-$C_1$–$C_4$-alkyl which is optionally substituted once or twice in an identical or different manner by fluorine, chlorine, methyl or ethyl, or represents pyridyloxy-$C_1$–$C_3$-alkyl, pyrimidyloxy-$C_1$–$C_3$-alkyl or thiazolyloxy-$C_1$–$C_3$-alkyl, in each case optionally substituted once or twice in an identical or different manner by fluorine, chlorine, amino, methyl or ethyl.

$R^2$ especially preferably represents $C_1$–$C_{14}$-alkyl, $C_2$–$C_{14}$-alkenyl, $C_1$–$C_4$-alkoxy-$C_2$–$C_6$-alkyl or poly-$C_1$–$C_4$-alkoxy-$C_2$–$C_6$-alkyl, in each case optionally substituted once to five times in an identical or different manner by fluorine or chlorine, or represents $C_3$–$C_6$-cycloalkyl which is optionally substituted once to three times in an identical or different manner by fluorine, chlorine, methyl, ethyl, methoxy or ethoxy, or represents phenyl or benzyl, in each case optionally substituted once or twice in an identical or different manner by fluorine, chlorine, nitro, cyano, methyl, ethyl, propyl, i-propyl, methoxy, ethoxy or trifluoromethyl.

$R^3$ especially preferably represents $C_1$–$C_6$-alkyl which is optionally substituted once to three times in an identical or different manner by fluorine or chlorine, or represents phenyl or benzyl, in each case optionally substitutes once or twice in an identical or different manner by fluorine, chlorine, bromine, methyl, methoxy, trifluoromethyl, trifluoromethoxy, cyano or nitro.

$R^4$ and $R^5$ independently of one another especially preferably represent $C_1$–$C_4$-alkyl, $C_1$–$C_4$-alkoxy, $C_1$–$C_4$-alkylamino, $C_3$–$C_4$-alkenylamino, di-($C_1$–$C_4$-alkyl)-amino, di-($C_3$–$C_4$-alkenyl)-amino, $C_1$–$C_4$-alkylthio, in each case optionally substituted once to three times in an identical or different manner by fluorine or chlorine, or represent phenyl, phenoxy or phenylthio, in each case optionally substituted once or twice in an identical or different manner by fluorine, chlorine, bromine, nitro, cyano, $C_1$–$C_2$-alkoxy, $C_1$–$C_2$-fluoroalkoxy, $C_1$–$C_2$-chloroalkoxy, $C_1$–$C_2$-alkylthio, $C_1$–$C_2$-fluoroalkylthio, $C_1$–$C_2$-chloroalkylthio or $C_1$–$C_3$-alkyl.

$R^6$ and $R^7$ independently of one another especially preferably represent hydrogen, or represent $C_1$–$C_4$-alkyl, $C_1$–$C_4$-alkoxy or $C_1$–$C_4$-alkoxy-$C_1$–$C_4$-alkyl, in each case optionally substituted once to three times in an identical or different manner by fluorine or chlorine, or represent phenyl which is optionally substituted once or twice in an identical or different manner by fluorine, chlorine, $C_1$–$C_2$-halogenoalkyl, $C_1$–$C_2$-alkyl or $C_1$–$C_2$-alkoxy, or represent benzyl which is optionally substituted once or twice in an identical or different manner by fluorine, chlorine, bromine, $C_1$–$C_2$-alkyl, $C_1$–$C_2$-halogenoalkyl or $C_1$–$C_2$-alkoxy, or together represent a $C_4$–$C_6$-alkylene radical, in which a methylene group can be replaced by oxygen or sulphur.

The enantiomerically pure forms of compounds of the formula (I) are included in, each case here.

A preferred group of compounds are compounds of the formula (Ih)

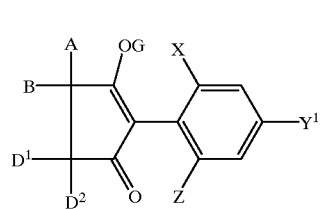

(Ih)

in which $Y^1$ has the meanings given above for Y in the definition of the compounds of the formula (I) with the exception of hydrogen, and A, B, $D^1$, $D^2$, X, Z and G have the meanings given above in the definition of the compounds of the formula (I).

A particularly preferred group of compounds are those compounds of the formula (Ih)

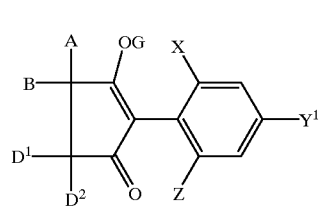

(Ih)

in which $Y^1$ has the abovementioned meaning,

A and B, together with the carbon atom to which they are bonded, form a saturated or unsaturated ring which is optionally interrupted by at least one heteroatom and is optionally substituted, or A and B, together with the carbon atom to which they are bonded, form a ring in which two substituents, together with the carbon atoms to which they are bonded, form a saturated or unsaturated ring which is optionally substituted once or several times in an identical or different manner by halogen, alkyl or alkoxy and can contain oxygen or sulphur and $D^1$, $D^2$, X, Z and G have the meanings given above in the definition of the compounds of the formula (I).

Another preferred group of compounds are the compounds of the formula (Ii)

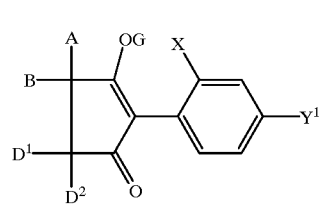

(Ii)

in which $Y^1$ has the abovementioned meaning and

A, B, $D^1$, $D^2$, X and G have the meanings given above in the definition of the compounds of the formula (I).

Another particularly preferred group of compounds are those compounds of the formula (Ii)

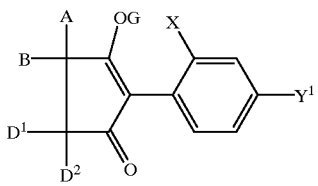

(Ii)

in which
- $Y^1$ has the abovementioned meaning,
- A and B, together with the carbon atom to which they are bonded, form a saturated or unsaturated ring which is optionally interrupted by at least one heteroatom and is optionally substituted, or
- A and B, together with the carbon atom to which they are bonded, form a ring in which two substituents, together with the carbon atoms to which they are bonded, form a saturated or unsaturated ring which is optionally substituted once or several times in an identical or different manner by halogen, alkyl or alkoxy and can contain oxygen or sulphur and
- $D^1$, $D^2$, X and G have the meanings given above in the definition of the compounds of the formula (I).

Another preferred group of compounds are compounds of the formula (Ij)

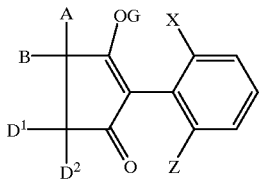

(Ij)

in which
A, B, $D^1$, $D^2$, G, X and Z have the meanings given above in the definition of the compounds of the formula (I).

Another particularly preferred group of compounds are those compounds of the formula (Ij)

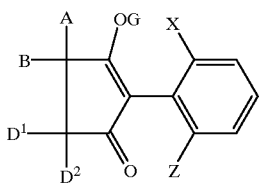

(Ij)

in which
- A and B, together with the carbon atom to which they are bonded, form a saturated or unsaturated ring which is optionally interrupted by at least one heteroatom and is optionally substituted, or
- A and B, together with the carbon atom to which they are bonded, form a ring in which two substituents, together with the carbon atoms to which they are bonded, form a saturated or unsaturated ring which is optionally substituted once or several times in an identical or different manner by halogen, alkyl or alkoxy and can contain oxygen or sulphur and
- $D^1$, $D^2$, X, Z and G have the meanings given above in the definition of the compounds of the formula (I).

The abovementioned definitions of radicals and explanations given generally or in preferred ranges can be combined as desired with one another, that is to say also between the particular ranges and preferred ranges. They apply to the end products and, correspondingly, to the precursors and intermediates.

The compounds of the formula (I) which are preferred according to the invention are those in which a combination of the meanings given above as preferred (preferably) is present.

The compounds of the formula (I) which are particularly preferred according to the invention are those in which a combination of the meanings given above as particularly preferred is present.

The compounds of the formula (I) which are especially preferred according to the invention are those in which a combination of the meanings given above as especially preferred is present.

In addition to the compounds mentioned in the preparation examples, the following 2-aryl-3-hydroxy-$\Delta^2$-cyclopentenone derivatives of the formula (Ia) may be mentioned specifically:

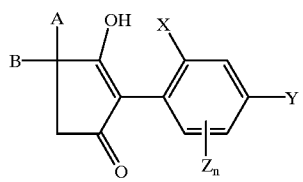

(Ia)

TABLE 1

| A | B | X | Y | $Z_N$ |
|---|---|---|---|---|
| —CH$_3$ | —CH$_3$ | —CH$_3$ | —CH$_3$ | 6-CH$_3$ |
| —C$_2$H$_5$ | —CH$_3$ | —CH$_3$ | —CH$_3$ | 6-CH$_3$ |
| —CH(CH$_3$)$_2$ | —CH$_3$ | —CH$_3$ | —CH$_3$ | 6-CH$_3$ |
| —CH$_2$—CH(CH$_3$)$_2$ | —CH$_3$ | —CH$_3$ | —CH$_3$ | 6-CH$_3$ |
| —C$_6$H$_5$ (phenyl) | —CH$_3$ | —CH$_3$ | —CH$_3$ | 6-CH$_3$ |
| —CH$_2$—C$_6$H$_5$ | —CH$_3$ | —CH$_3$ | —CH$_3$ | 6-CH$_3$ |
| —CH$_2$CH$_2$—C$_6$H$_5$ | —CH$_3$ | —CH$_3$ | —CH$_3$ | 6-CH$_3$ |
| —C$_2$H$_5$ | —C$_2$H$_5$ | —CH$_3$ | —CH$_3$ | 6-CH$_3$ |
| —(CH$_2$)$_2$— | | —CH$_3$ | —CH$_3$ | 6-CH$_3$ |
| —(CH$_2$)$_4$— | | —CH$_3$ | —CH$_3$ | 6-CH$_3$ |
| —(CH$_2$)$_5$— | | —CH$_3$ | —CH$_3$ | 6-CH$_3$ |
| —(CH$_2$)$_6$— | | —CH$_3$ | —CH$_3$ | 6-CH$_3$ |
| —(CH$_2$)$_7$— | | —CH$_3$ | —CH$_3$ | 6-CH$_3$ |
| —CH$_2$—CHCH$_3$(CH$_2$)$_2$— | | —CH$_3$ | —CH$_3$ | 6-CH$_3$ |
| —CH(CH$_3$)—(CH$_2$)$_4$— | | —CH$_3$ | —CH$_3$ | 6-CH$_3$ |
| —CH$_2$—CH(CH$_3$)—(CH$_2$)$_3$— | | —CH$_3$ | —CH$_3$ | 6-CH$_3$ |
| —(CH$_2$)$_2$—CH(CH$_3$)—(CH$_2$)$_2$— | | —CH$_3$ | —CH$_3$ | 6-CH$_3$ |
| —C(CH$_2$)$_2$—CH(—C(CH$_3$)$_3$)—(CH$_2$)$_2$— | | —CH$_3$ | —CH$_3$ | 6-CH$_3$ |

TABLE 1-continued

| A | B | X | Y | $Z_N$ |
|---|---|---|---|---|
| o-xylylene (—CH₂-C₆H₄-CH₂—) | | —CH₃ | —CH₃ | 6-CH₃ |
| —(CH₂)₂—CH(C₂H₅)—(CH₂)₂— | | —CH₃ | —CH₃ | 6-CH₃ |
| —(CH₂)₂—CH(i-C₃H₇)—(CH₂)₂— | | —CH₃ | —CH₃ | 6-CH₃ |
| —CH₂—CHCH₃—CHCH₃—(CH₂)₂— | | —CH₃ | —CH₃ | 6-CH₃ |
| —(CH₂)₂—CHOCH₃—(CH₂)₂— | | —CH₃ | —CH₃ | 6-CH₃ |
| —(CH₂)₂—CHOC₂H₅—(CH₂)₂— | | —CH₃ | —CH₃ | 6-CH₃ |
| —CH₃ | —CH₃ | Cl | Cl | H |
| —C₂H₅ | —CH₃ | Cl | Cl | H |
| —CH(CH₃)₂ | —CH₃ | Cl | Cl | H |
| —CH₂—CH(CH₃)₂ | —CH₃ | Cl | Cl | H |
| —(CH₂)₄— | | Cl | Cl | H |
| —(CH₂)₅— | | Cl | Cl | H |
| —(CH₂)₆— | | Cl | Cl | H |
| —CH₂—CH(CH₃)—(CH₂)₃— | | Cl | Cl | H |
| —(CH₂)₂—CH(CH₃)—(CH₂)₂— | | Cl | Cl | H |
| —(CH₂)₂—CH(C₂H₅)—(CH₂)₂— | | Cl | Cl | H |
| —(CH₂)₂—CH(i-C₃H₇)—(CH₂)₂— | | Cl | Cl | H |
| —CH₂—CHCH₃—CHCH₃—(CH₂)₂— | | Cl | Cl | H |
| —(CH₂)₂—CHOCH₃—(CH₂)₂— | | Cl | Cl | H |
| —(CH₂)₂—CHOC₂H₅—(CH₂)₂— | | Cl | Cl | H |
| —CH₃ | —CH₃ | Cl | H | 6-Cl |
| —C₂H₅ | —CH₃ | Cl | H | 6-Cl |
| —CH(CH₃)₂ | —CH₃ | Cl | H | 6-Cl |
| —CH₂—CH(CH₃)₂ | —CH₃ | Cl | H | 6-Cl |
| —(CH₂)₄— | | Cl | H | 6-Cl |
| —(CH₂)₅— | | Cl | H | 6-Cl |
| —(CH₂)₆— | | Cl | H | 6-Cl |
| —CH₂—CH(CH₃)—(CH₂)₃— | | Cl | H | 6-Cl |
| —(CH₂)₂—CH(CH₃)—(CH₂)₂— | | Cl | H | 6-Cl |
| —(CH₂)₂—CH(C₂H₅)—(CH₂)₂— | | Cl | H | 6-Cl |
| —(CH₂)₂—CH(i-C₃H₇)—(CH₂)₂— | | Cl | H | 6-Cl |
| —(CH₂)₂—CHOCH₃—(CH₂)₂— | | Cl | H | 6-Cl |
| —(CH₂)₂—CHOC₂H₅—(CH₂)₂— | | Cl | H | 6-Cl |
| —CH₃ | —CH₃ | Cl | H | 6-F |
| —C₂H₅ | —CH₃ | Cl | H | 6-F |
| —CH(CH₃)₂ | —CH₃ | Cl | H | 6-F |
| —CH₂—CH(CH₃)₂ | —CH₃ | Cl | H | 6-F |
| —(CH₂)₄— | | Cl | H | 6-F |
| —(CH₂)₅— | | Cl | H | 6-F |
| —(CH₂)₆— | | Cl | H | 6-F |
| —CH₂—CH(CH₃)—(CH₂)₃— | | Cl | H | 6-F |
| —(CH₂)₂—CH(CH₃)—(CH₂)₂— | | Cl | H | 6-F |
| —(CH₂)₂—CH(C₂H₅)—(CH₂)₂— | | Cl | H | 6-F |
| —(CH₂)₂—CH(i-C₃H₇)—(CH₂)₂— | | Cl | H | 6-F |
| —(CH₂)₂—CHOCH₃—(CH₂)₂— | | Cl | H | 6-F |
| —(CH₂)₂—CHOC₂H₅—(CH₂)₂— | | Cl | H | 6-F |
| —CH₃ | —CH₃ | —CH₃ | —CH₃ | H |
| —C₂H₅ | —CH₃ | —CH₃ | —CH₃ | H |
| —CH(CH₃)₂ | —CH₃ | —CH₃ | —CH₃ | H |
| —CH₂—CH(CH₃)₂ | —CH₃ | —CH₃ | —CH₃ | H |
| —(CH₂)₄— | | —CH₃ | —CH₃ | H |
| —(CH₂)₅— | | —CH₃ | —CH₃ | H |
| —(CH₂)₆— | | —CH₃ | —CH₃ | H |
| —CH₂—CH(CH₃)—(CH₂)₃— | | —CH₃ | —CH₃ | H |
| —(CH₂)₂—CH(CH₃)—(CH₂)₂— | | —CH₃ | —CH₃ | H |
| —(CH₂)₂—CH(C₂H₅)—(CH₂)₂— | | —CH₃ | —CH₃ | H |
| —(CH₂)₂—CH(i-C₃H₇)—(CH₂)₂— | | —CH₃ | —CH₃ | H |
| —CH₂—CHCH₃—CHCH₃—(CH₂)₂— | | —CH₃ | —CH₃ | H |
| —(CH₂)₂—CHOCH₃—(CH₂)₂— | | —CH₃ | —CH₃ | H |
| —(CH₂)₂—CHOC₂H₅—(CH₂)₂— | | —CH₃ | —CH₃ | H |
| —CH₃ | —CH₃ | —Cl | —CF₃ | 6-Cl |
| —C₂H₅ | —CH₃ | —Cl | —CF₃ | 6-Cl |
| —CH(CH₃)₂ | —CH₃ | —Cl | —CF₃ | 6-Cl |
| —CH₂—CH(CH₃)₂ | —CH₃ | —Cl | —CF₃ | 6-Cl |
| —(CH₂)₄— | | —Cl | —CF₃ | 6-Cl |
| —(CH₂)₅— | | —Cl | —CF₃ | 6-Cl |
| —(CH₂)₆— | | —Cl | —CF₃ | 6-Cl |
| —CH₂—CH(CH₃)—(CH₂)₃— | | —Cl | —CF₃ | 6-Cl |
| —(CH₂)₂—CH(CH₃)—(CH₂)₂— | | —Cl | —CF₃ | 6-Cl |
| —(CH₂)₂—CH(C₂H₅)—(CH₂)₂— | | —Cl | —CF₃ | 6-Cl |
| —(CH₂)₂—CH(i-C₃H₇)—(CH₂)₂— | | —Cl | —CF₃ | 6-Cl |
| —(CH₂)₂—CHOCH₃—(CH₂)₂— | | —Cl | —CF₃ | 6-Cl |
| —(CH₂)₂—CHOC₂H₅—(CH₂)₂— | | —Cl | —CF₃ | 6-Cl |

In addition to the compounds mentioned in the preparation examples, the following 2-aryl-3-hydroxy-Δ²-cyclopentenone derivatives of the formula (Ib) may be mentioned specifically (Table 2):

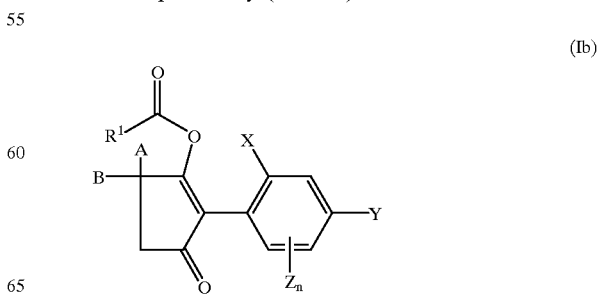

(Ib)

TABLE 2

| A | B | X | Y | Z$_n$ | R$^1$ |
|---|---|---|---|---|---|
| —CH$_3$ | —CH$_3$ | —CH$_3$ | —CH$_3$ | 6-CH$_3$ | —CH$_3$ |
| —CH$_3$ | —CH$_3$ | —CH$_3$ | —CH$_3$ | 6-CH$_3$ | —C$_2$H$_5$ |
| —CH$_3$ | —CH$_3$ | —CH$_3$ | —CH$_3$ | 6-CH$_3$ | —C$_3$H$_7$ |
| —CH$_3$ | —CH$_3$ | —CH$_3$ | —CH$_3$ | 6-CH$_3$ | —C$_4$H$_9$ |
| —CH$_3$ | —CH$_3$ | —CH$_3$ | —CH$_3$ | 6-CH$_3$ | —CH(CH$_3$)$_2$ |
| —CH$_3$ | —CH$_3$ | —CH$_3$ | —CH$_3$ | 6-CH$_3$ | —CH$_2$CH(CH$_3$)$_2$ |
| —CH$_3$ | —CH$_3$ | —CH$_3$ | —CH$_3$ | 6-CH$_3$ | —C(CH$_3$)$_3$ |
| —CH$_3$ | —CH$_3$ | —CH$_3$ | —CH$_3$ | 6-CH$_3$ | —C(CH$_3$)$_2$—C$_2$H$_5$ |
| —CH$_3$ | —CH$_3$ | —CH$_3$ | —CH$_3$ | 6-CH$_3$ | —C(CH$_3$)$_2$—CH(CH$_3$)$_2$ |
| —CH$_3$ | —CH$_3$ | —CH$_3$ | —CH$_3$ | 6-CH$_3$ | —CH$_2$—C(CH$_3$)$_3$ |
| —CH$_3$ | —CH$_3$ | —CH$_3$ | —CH$_3$ | 6-CH$_3$ | —CH(C$_2$H$_5$)—C$_4$H$_9$ |
| —CH$_3$ | —CH$_3$ | —CH$_3$ | —CH$_3$ | 6-CH$_3$ | —C(CH$_3$)$_2$—CH$_2$Cl |
| —CH$_3$ | —CH$_3$ | —CH$_3$ | —CH$_3$ | 6-CH$_3$ | —C(CH$_3$)(CH$_2$Cl)$_2$ |
| —CH$_3$ | —CH$_3$ | —CH$_3$ | —CH$_3$ | 6-CH$_3$ | —C(CH$_3$)$_2$—CH$_2$OCH$_3$ |
| —CH$_3$ | —CH$_3$ | —CH$_3$ | —CH$_3$ | 6-CH$_3$ | —C(CH$_3$)—(CH$_2$—OCH$_3$)$_2$ |
| —CH$_3$ | —CH$_3$ | —CH$_3$ | —CH$_3$ | 6-CH$_3$ | —CH=C(CH$_3$)$_2$ |
| —CH$_3$ | —CH$_3$ | —CH$_3$ | —CH$_3$ | 6-CH$_3$ | cyclopropyl |
| —CH$_3$ | —CH$_3$ | —CH$_3$ | —CH$_3$ | 6-CH$_3$ | cyclohexyl |
| —CH$_3$ | —CH$_3$ | —CH$_3$ | —CH$_3$ | 6-CH$_3$ | 1-methylcyclohexyl |
| —CH$_3$ | —CH$_3$ | —CH$_3$ | —CH$_3$ | 6-CH$_3$ | phenyl |
| —CH$_3$ | —CH$_3$ | —CH$_3$ | —CH$_3$ | 6-CH$_3$ | 2-thienyl |
| —CH$_3$ | —CH$_3$ | —CH$_3$ | —CH$_3$ | 6-CH$_3$ | 2-furyl |
| —CH$_3$ | —CH$_3$ | —CH$_3$ | —CH$_3$ | 6-CH$_3$ | —CH$_2$-phenyl |
| —CH$_3$ | —CH$_3$ | —CH$_3$ | —CH$_3$ | 6-CH$_3$ | 3-pyridyl |
| —CH(CH$_3$)$_2$ | —CH$_3$ | —CH$_3$ | —CH$_3$ | 6-CH$_3$ | —CH$_3$ |
| —CH(CH$_3$)$_2$ | —CH$_3$ | —CH$_3$ | —CH$_3$ | 6-CH$_3$ | —C$_2$H$_5$ |
| —CH(CH$_3$)$_2$ | —CH$_3$ | —CH$_3$ | —CH$_3$ | 6-CH$_3$ | —C$_3$H$_7$ |
| —CH(CH$_3$)$_2$ | —CH$_3$ | —CH$_3$ | —CH$_3$ | 6-CH$_3$ | —C$_4$H$_9$ |
| —CH(CH$_3$)$_2$ | —CH$_3$ | —CH$_3$ | —CH$_3$ | 6-CH$_3$ | —CH(CH$_3$)$_2$ |
| —CH(CH$_3$)$_2$ | —CH$_3$ | —CH$_3$ | —CH$_3$ | 6-CH$_3$ | —CH$_2$CH(CH$_3$)$_2$ |
| —CH(CH$_3$)$_2$ | —CH$_3$ | —CH$_3$ | —CH$_3$ | 6-CH$_3$ | —C(CH$_3$)$_3$ |
| —CH(CH$_3$)$_2$ | —CH$_3$ | —CH$_3$ | —CH$_3$ | 6-CH$_3$ | —C(CH$_3$)$_2$—C$_2$H$_5$ |

TABLE 2-continued

| A | B | X | Y | $Z_n$ | $R^1$ |
|---|---|---|---|---|---|
| —CH(CH₃)₂ | —CH₃ | —CH₃ | —CH₃ | 6-CH₃ | —C(CH₃)₂—CH(CH₃)₂ |
| —CH(CH₃)₂ | —CH₃ | —CH₃ | —CH₃ | 6-CH₃ | —CH₂—C(CH₃)₃ |
| —CH(CH₃)₂ | —CH₃ | —CH₃ | —CH₃ | 6-CH₃ | —CH(C₂H₅)—C₄H₉ |
| —CH(CH₃)₂ | —CH₃ | —CH₃ | —CH₃ | 6-CH₃ | —C(CH₃)₂—CH₂Cl |
| —CH(CH₃)₂ | —CH₃ | —CH₃ | —CH₃ | 6-CH₃ | —C(CH₃)(CH₂Cl)₂ |
| —CH(CH₃)₂ | —CH₃ | —CH₃ | —CH₃ | 6-CH₃ | —C(CH₃)₂—CH₂OCH₃ |
| —CH(CH₃)₂ | —CH₃ | —CH₃ | —CH₃ | 6-CH₃ | —C(CH₃)—(CH₂—OCH₃)₂ |
| —CH(CH₃)₂ | —CH₃ | —CH₃ | —CH₃ | 6-CH₃ | —CH=C(CH₃)₂ |
| —CH(CH₃)₂ | —CH₃ | —CH₃ | —CH₃ | 6-CH₃ |  |
| —CH(CH₃)₂ | —CH₃ | —CH₃ | —CH₃ | 6-CH₃ |  |
| —CH(CH₃)₂ | —CH₃ | —CH₃ | —CH₃ | 6-CH₃ |  |
| —CH(CH₃)₂ | —CH₃ | —CH₃ | —CH₃ | 6-CH₃ | 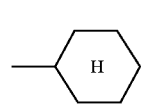 |
| —CH(CH₃)₂ | —CH₃ | —CH₃ | —CH₃ | 6-CH₃ | 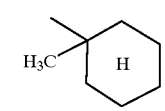 |
| —CH(CH₃)₂ | —CH₃ | —CH₃ | —CH₃ | 6-CH₃ | 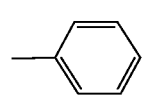 |
| —CH(CH₃)₂ | —CH₃ | —CH₃ | —CH₃ | 6-CH₃ | 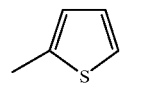 |
| —CH(CH₃)₂ | —CH₃ | —CH₃ | —CH₃ | 6-CH₃ | 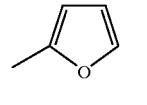 |
| | —(CH₂)₄— | —CH₃ | —CH₃ | 6-CH₃ | —CH₃ |
| | —(CH₂)₄— | —CH₃ | —CH₃ | 6-CH₃ | —C₂H₅ |
| | —(CH₂)₄— | —CH₃ | —CH₃ | 6-CH₃ | —C₃H₇ |
| | —(CH₂)₄— | —CH₃ | —CH₃ | 6-CH₃ | —C₄H₉ |
| | —(CH₂)₄— | —CH₃ | —CH₃ | 6-CH₃ | —CH(CH₃)₂ |
| | —(CH₂)₄— | —CH₃ | —CH₃ | 6-CH₃ | —CH₂CH(CH₃)₂ |
| | —(CH₂)₄— | —CH₃ | —CH₃ | 6-CH₃ | —C(CH₃)₃ |
| | —(CH₂)₄— | —CH₃ | —CH₃ | 6-CH₃ | —C(CH₃)₂—C₂H₅ |
| | —(CH₂)₄— | —CH₃ | —CH₃ | 6-CH₃ | —C(CH₃)₂—CH(CH₃)₂ |
| | —(CH₂)₄— | —CH₃ | —CH₃ | 6-CH₃ | —CH₂—C(CH₃)₃ |
| | —(CH₂)₄— | —CH₃ | —CH₃ | 6-CH₃ | —CH(C₂H₅)—C₄H₉ |
| | —(CH₂)₄— | —CH₃ | —CH₃ | 6-CH₃ | —C(CH₃)₂—CH₂Cl |

TABLE 2-continued

| A | B | X | Y | $Z_n$ | $R^1$ |
|---|---|---|---|---|---|
|  | —(CH$_2$)$_4$— | —CH$_3$ | —CH$_3$ | 6-CH$_3$ |  |
|  | —(CH$_2$)$_4$— | —CH$_3$ | —CH$_3$ | 6-CH$_3$ | —C(CH$_3$)$_2$—CH$_2$OCH$_3$ |
|  | —(CH$_2$)$_4$— | —CH$_3$ | —CH$_3$ | 6-CH$_3$ | —C(CH$_3$)—(CH$_2$—OCH$_3$)$_2$ |
|  | —(CH$_2$)$_4$— | —CH$_3$ | —CH$_3$ | 6-CH$_3$ | —CH=C(CH$_3$)$_2$ |
|  | —(CH$_2$)$_4$— | —CH$_3$ | —CH$_3$ | 6-CH$_3$ |  |
|  | —(CH$_2$)$_4$— | —CH$_3$ | —CH$_3$ | 6-CH$_3$ | 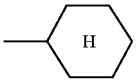 |
|  | —(CH$_2$)$_4$— | —CH$_3$ | —CH$_3$ | 6-CH$_3$ | 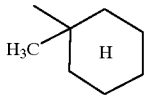 |
|  | —(CH$_2$)$_4$— | —CH$_3$ | —CH$_3$ | 6-CH$_3$ | 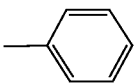 |
|  | —(CH$_2$)$_4$— | —CH$_3$ | —CH$_3$ | 6-CH$_3$ | 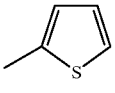 |
|  | —(CH$_2$)$_4$— | —CH$_3$ | —CH$_3$ | 6-CH$_3$ | 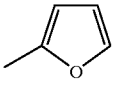 |
|  | —(CH$_2$)$_4$— | —CH$_3$ | —CH$_3$ | 6-CH$_3$ | 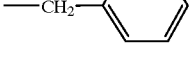 |
|  | —(CH$_2$)$_4$— | —CH$_3$ | —CH$_3$ | 6-CH$_3$ | 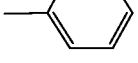 |
|  | —(CH$_2$)$_5$— | —CH$_3$ | —CH$_3$ | 6-CH$_3$ | —CH$_3$ |
|  | —(CH$_2$)$_5$— | —CH$_3$ | —CH$_3$ | 6-CH$_3$ | —C$_2$H$_5$ |
|  | —(CH$_2$)$_5$— | —CH$_3$ | —CH$_3$ | 6-CH$_3$ | —C$_3$H$_7$ |
|  | —(CH$_2$)$_5$— | —CH$_3$ | —CH$_3$ | 6-CH$_3$ | —C$_4$H$_9$ |
|  | —(CH$_2$)$_5$— | —CH$_3$ | —CH$_3$ | 6-CH$_3$ | —CH(CH$_3$)$_2$ |
|  | —(CH$_2$)$_5$— | —CH$_3$ | —CH$_3$ | 6-CH$_3$ | —CH$_2$CH(CH$_3$)$_2$ |
|  | —(CH$_2$)$_5$— | —CH$_3$ | —CH$_3$ | 6-CH$_3$ | —C(CH$_3$)$_3$ |
|  | —(CH$_2$)$_5$— | —CH$_3$ | —CH$_3$ | 6-CH$_3$ | —C(CH$_3$)$_2$—C$_2$H$_5$ |
|  | —(CH$_2$)$_5$— | —CH$_3$ | —CH$_3$ | 6-CH$_3$ | —C(CH$_3$)$_2$—CH(CH$_3$)$_2$ |
|  | —(CH$_2$)$_5$— | —CH$_3$ | —CH$_3$ | 6-CH$_3$ | —CH$_2$—C(CH$_3$)$_3$ |
|  | —(CH$_2$)$_5$— | —CH$_3$ | —CH$_3$ | 6-CH$_3$ | —CH(C$_2$H$_5$)—C$_4$H$_9$ |
|  | —(CH$_2$)$_5$— | —CH$_3$ | —CH$_3$ | 6-CH$_3$ | —C(CH$_3$)$_2$—CH$_2$Cl |
|  | —(CH$_2$)$_5$— | —CH$_3$ | —CH$_3$ | 6-CH$_3$ | 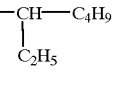 |
|  | —(CH$_2$)$_5$— | —CH$_3$ | —CH$_3$ | 6-CH$_3$ | —C(CH$_3$)$_2$—CH$_2$OCH$_3$ |
|  | —(CH$_2$)$_5$— | —CH$_3$ | —CH$_3$ | 6-CH$_3$ | —C(CH$_3$)—(CH$_2$—OCH$_3$)$_2$ |
|  | —(CH$_2$)$_5$— | —CH$_3$ | —CH$_3$ | 6-CH$_3$ | —CH=C(CH$_3$)$_2$ |

TABLE 2-continued

| A | B | X | Y | $Z_n$ | $R^1$ |
|---|---|---|---|---|---|
| | —(CH$_2$)$_5$— | —CH$_3$ | —CH$_3$ | 6-CH$_3$ |  |
| | —(CH$_2$)$_5$— | —CH$_3$ | —CH$_3$ | 6-CH$_3$ | 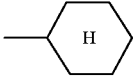 |
| | —(CH$_2$)$_5$— | —CH$_3$ | —CH$_3$ | 6-CH$_3$ | 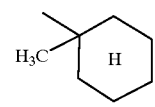 |
| | —(CH$_2$)$_5$— | —CH$_3$ | —CH$_3$ | 6-CH$_3$ | 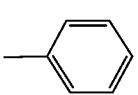 |
| | —(CH$_2$)$_5$— | —CH$_3$ | —CH$_3$ | 6-CH$_3$ | 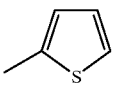 |
| | —(CH$_2$)$_5$— | —CH$_3$ | —CH$_3$ | 6-CH$_3$ | 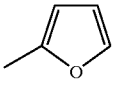 |
| | —(CH$_2$)$_5$— | —CH$_3$ | —CH$_3$ | 6-CH$_3$ | 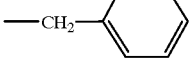 |
| | —(CH$_2$)$_5$— | —CH$_3$ | —CH$_3$ | 6-CH$_3$ | 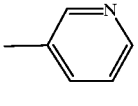 |
| | —CH$_2$—CH(CH$_3$)—(CH$_2$)$_3$— | —CH$_3$ | —CH$_3$ | 6-CH$_3$ | —CH$_3$ |
| | —CH$_2$—CH(CH$_3$)—(CH$_2$)$_3$— | —CH$_3$ | —CH$_3$ | 6-CH$_3$ | —C$_2$H$_5$ |
| | —CH$_2$—CH(CH$_3$)—(CH$_2$)$_3$— | —CH$_3$ | —CH$_3$ | 6-CH$_3$ | —C$_3$H$_7$ |
| | —CH$_2$—CH(CH$_3$)—(CH$_2$)$_3$— | —CH$_3$ | —CH$_3$ | 6-CH$_3$ | —C$_4$H$_9$ |
| | —CH$_2$—CH(CH$_3$)—(CH$_2$)$_3$— | —CH$_3$ | —CH$_3$ | 6-CH$_3$ | —CH(CH$_3$)$_2$ |
| | —CH$_2$—CH(CH$_3$)—(CH$_2$)$_3$— | —CH$_3$ | —CH$_3$ | 6-CH$_3$ | —CH$_2$CH(CH$_3$)$_2$ |
| | —CH$_2$—CH(CH$_3$)—(CH$_2$)$_3$— | —CH$_3$ | —CH$_3$ | 6-CH$_3$ | —C(CH$_3$)$_3$ |
| | —CH$_2$—CH(CH$_3$)—(CH$_2$)$_3$— | —CH$_3$ | —CH$_3$ | 6-CH$_3$ | —C(CH$_3$)$_2$—C$_2$H$_5$ |
| | —CH$_2$—CH(CH$_3$)—(CH$_2$)$_3$— | —CH$_3$ | —CH$_3$ | 6-CH$_3$ | —C(CH$_3$)$_2$—CH(CH$_3$)$_2$ |
| | —CH$_2$—CH(CH$_3$)—(CH$_2$)$_3$— | —CH$_3$ | —CH$_3$ | 6-CH$_3$ | —CH$_2$—C(CH$_3$)$_3$ |
| | —CH$_2$—CH(CH$_3$)—(CH$_2$)$_3$— | —CH$_3$ | —CH$_3$ | 6-CH$_3$ | —CH(C$_2$H$_5$)—C$_4$H$_9$ |
| | —CH$_2$—CH(CH$_3$)—(CH$_2$)$_3$— | —CH$_3$ | —CH$_3$ | 6-CH$_3$ | —C(CH$_3$)$_2$—CH$_2$Cl |
| | —CH$_2$—CH(CH$_3$)—(CH$_2$)$_3$— | —CH$_3$ | —CH$_3$ | 6-CH$_3$ | —C(CH$_3$)(CH$_2$Cl)$_2$ |
| | —CH$_2$—CH(CH$_3$)—(CH$_2$)$_3$— | —CH$_3$ | —CH$_3$ | 6-CH$_3$ | —C(CH$_3$)$_2$—CH$_2$OCH$_3$ |
| | —CH$_2$—CH(CH$_3$)—(CH$_2$)$_3$— | —CH$_3$ | —CH$_3$ | 6-CH$_3$ | —C(CH$_3$)—(CH$_2$—OCH$_3$)$_2$ |
| | —CH$_2$—CH(CH$_3$)—(CH$_2$)$_3$— | —CH$_3$ | —CH$_3$ | 6-CH$_3$ | —CH═C(CH$_3$)$_2$ |
| | —CH$_2$—CH(CH$_3$)—(CH$_2$)$_3$— | —CH$_3$ | —CH$_3$ | 6-CH$_3$ |  |

TABLE 2-continued

| A | B | X | Y | Z$_n$ | R$^1$ |
|---|---|---|---|---|---|
| | —CH$_2$—CH(CH$_3$)—(CH$_2$)$_3$— | —CH$_3$ | —CH$_3$ | 6-CH$_3$ | cyclohexyl (H) |
| | —CH$_2$—CH(CH$_3$)—(CH$_2$)$_3$— | —CH$_3$ | —CH$_3$ | 6-CH$_3$ | 1-methyl-cyclohexyl (H$_3$C, H) |
| | —CH$_2$—CH(CH$_3$)—(CH$_2$)$_3$— | —CH$_3$ | —CH$_3$ | 6-CH$_3$ | phenyl |
| | —CH$_2$—CH(CH$_3$)—(CH$_2$)$_3$— | —CH$_3$ | —CH$_3$ | 6-CH$_3$ | 2-thienyl |
| | —CH$_2$—CH(CH$_3$)—(CH$_2$)$_3$— | —CH$_3$ | —CH$_3$ | 6-CH$_3$ | 2-furyl |
| | —CH$_2$—CH(CH$_3$)—(CH$_2$)$_3$— | —CH$_3$ | —CH$_3$ | 6-CH$_3$ | —CH$_2$-phenyl |
| | —CH$_2$—CH(CH$_3$)—(CH$_2$)$_3$— | —CH$_3$ | —CH$_3$ | 6-CH$_3$ | 3-pyridyl |
| | —(CH$_2$)$_2$—CH(CH$_3$)—(CH$_2$)$_2$— | —CH$_3$ | —CH$_3$ | 6-CH$_3$ | —CH$_3$ |
| | —(CH$_2$)$_2$—CH(CH$_3$)—(CH$_2$)$_2$— | —CH$_3$ | —CH$_3$ | 6-CH$_3$ | —C$_2$H$_5$ |
| | —(CH$_2$)$_2$—CH(CH$_3$)—(CH$_2$)$_2$— | —CH$_3$ | —CH$_3$ | 6-CH$_3$ | —C$_3$H$_7$ |
| | —(CH$_2$)$_2$—CH(CH$_3$)—(CH$_2$)$_2$— | —CH$_3$ | —CH$_3$ | 6-CH$_3$ | —C$_4$H$_9$ |
| | —(CH$_2$)$_2$—CH(CH$_3$)—(CH$_2$)$_2$— | —CH$_3$ | —CH$_3$ | 6-CH$_3$ | —CH(CH$_3$)$_2$ |
| | —(CH$_2$)$_2$—CH(CH$_3$)—(CH$_2$)$_2$— | —CH$_3$ | —CH$_3$ | 6-CH$_3$ | —CH$_2$CH(CH$_3$)$_2$ |
| | —(CH$_2$)$_2$—CH(CH$_3$)—(CH$_2$)$_2$— | —CH$_3$ | —CH$_3$ | 6-CH$_3$ | —C(CH$_3$)$_3$ |
| | —(CH$_2$)$_2$—CH(CH$_3$)—(CH$_2$)$_2$— | —CH$_3$ | —CH$_3$ | 6-CH$_3$ | —C(CH$_3$)$_2$—C$_2$H$_5$ |
| | —(CH$_2$)$_2$—CH(CH$_3$)—(CH$_2$)$_2$— | —CH$_3$ | —CH$_3$ | 6-CH$_3$ | —C(CH$_3$)$_2$—CH(CH$_3$)$_2$ |
| | —(CH$_2$)$_2$—CH(CH$_3$)—(CH$_2$)$_2$— | —CH$_3$ | —CH$_3$ | 6-CH$_3$ | —CH$_2$—C(CH$_3$)$_3$ |
| | —(CH$_2$)$_2$—CH(CH$_3$)—(CH$_2$)$_2$— | —CH$_3$ | —CH$_3$ | 6-CH$_3$ | —CH(C$_2$H$_5$)—C$_4$H$_9$ |
| | —(CH$_2$)$_2$—CH(CH$_3$)—(CH$_2$)$_2$— | —CH$_3$ | —CH$_3$ | 6-CH$_3$ | —C(CH$_3$)$_2$—CH$_2$Cl |
| | —(CH$_2$)$_2$—CH(CH$_3$)—(CH$_2$)$_2$— | —CH$_3$ | —CH$_3$ | 6-CH$_3$ | —C(CH$_2$Cl)$_2$—CH$_3$ |
| | —(CH$_2$)$_2$—CH(CH$_3$)—(CH$_2$)$_2$— | —CH$_3$ | —CH$_3$ | 6-CH$_3$ | —C(CH$_3$)$_2$—CH$_2$OCH$_3$ |
| | —(CH$_2$)$_2$—CH(CH$_3$)—(CH$_2$)$_2$— | —CH$_3$ | —CH$_3$ | 6-CH$_3$ | —C(CH$_3$)—(CH$_2$OCH$_3$)$_2$ |
| | —(CH$_2$)$_2$—CH(CH$_3$)—(CH$_2$)$_2$— | —CH$_3$ | —CH$_3$ | 6-CH$_3$ | —CH═C(CH$_3$)$_2$ |
| | —(CH$_2$)$_2$—CH(CH$_3$)—(CH$_2$)$_2$— | —CH$_3$ | —CH$_3$ | 6-CH$_3$ | cyclopropyl |
| | —(CH$_2$)$_2$—CH(CH$_3$)—(CH$_2$)$_2$— | —CH$_3$ | —CH$_3$ | 6-CH$_3$ | cyclohexyl (H) |

TABLE 2-continued

| A | B | X | Y | $Z_n$ | $R^1$ |
|---|---|---|---|---|---|
| | —(CH$_2$)$_2$—CH(CH$_3$)—(CH$_2$)$_2$— | —CH$_3$ | —CH$_3$ | 6-CH$_3$ | 1-methylcyclohexyl (H$_3$C, H) |
| | —(CH$_2$)$_2$—CH(CH$_3$)—(CH$_2$)$_2$— | —CH$_3$ | —CH$_3$ | 6-CH$_3$ | phenyl |
| | —(CH$_2$)$_2$—CH(CH$_3$)—(CH$_2$)$_2$— | —CH$_3$ | —CH$_3$ | 6-CH$_3$ | 2-thienyl |
| | —(CH$_2$)$_2$—CH(CH$_3$)—(CH$_2$)$_2$— | —CH$_3$ | —CH$_3$ | 6-CH$_3$ | 2-furyl |
| | —(CH$_2$)$_2$—CH(CH$_3$)—(CH$_2$)$_2$— | —CH$_3$ | —CH$_3$ | 6-CH$_3$ | —CH$_2$-phenyl |
| | —(CH$_2$)$_2$—CH(CH$_3$)—(CH$_2$)$_2$— | —CH$_3$ | —CH$_3$ | 6-CH$_3$ | 3-pyridyl |
| | —(CH$_2$)$_2$—CH(OCH$_3$)—(CH$_2$)$_2$— | —CH$_3$ | —CH$_3$ | 6-CH$_3$ | —CH$_3$ |
| | —(CH$_2$)$_2$—CH(OCH$_3$)—(CH$_2$)$_2$— | —CH$_3$ | —CH$_3$ | 6-CH$_3$ | —C$_2$H$_5$ |
| | —(CH$_2$)$_2$—CH(OCH$_3$)—(CH$_2$)$_2$— | —CH$_3$ | —CH$_3$ | 6-CH$_3$ | —C$_3$H$_7$ |
| | —(CH$_2$)$_2$—CH(OCH$_3$)—(CH$_2$)$_2$— | —CH$_3$ | —CH$_3$ | 6-CH$_3$ | —C$_4$H$_9$ |
| | —(CH$_2$)$_2$—CH(OCH$_3$)—(CH$_2$)$_2$— | —CH$_3$ | —CH$_3$ | 6-CH$_3$ | —CH(CH$_3$)$_2$ |
| | —(CH$_2$)$_2$—CH(OCH$_3$)—(CH$_2$)$_2$— | —CH$_3$ | —CH$_3$ | 6-CH$_3$ | —CH$_2$CH(CH$_3$)$_2$ |
| | —(CH$_2$)$_2$—CH(OCH$_3$)—(CH$_2$)$_2$— | —CH$_3$ | —CH$_3$ | 6-CH$_3$ | —C(CH$_3$)$_3$ |
| | —(CH$_2$)$_2$—CH(OCH$_3$)—(CH$_2$)$_2$— | —CH$_3$ | —CH$_3$ | 6-CH$_3$ | —C(CH$_3$)$_2$—C$_2$H$_5$ |
| | —(CH$_2$)$_2$—CH(OCH$_3$)—(CH$_2$)$_2$— | —CH$_3$ | —CH$_3$ | 6-CH$_3$ | —C(CH$_3$)$_2$—CH(CH$_3$)$_2$ |
| | —(CH$_2$)$_2$—CH(OCH$_3$)—(CH$_2$)$_2$— | —CH$_3$ | —CH$_3$ | 6-CH$_3$ | —CH$_2$—C(CH$_3$)$_3$ |
| | —(CH$_2$)$_2$—CH(OCH$_3$)—(CH$_2$)$_2$— | —CH$_3$ | —CH$_3$ | 6-CH$_3$ | —CH(C$_2$H$_5$)—C$_4$H$_9$ |
| | —(CH$_2$)$_2$—CH(OCH$_3$)—(CH$_2$)$_2$— | —CH$_3$ | —CH$_3$ | 6-CH$_3$ | —C(CH$_3$)$_2$—CH$_2$Cl |
| | —(CH$_2$)$_2$—CH(OCH$_3$)—(CH$_2$)$_2$— | —CH$_3$ | —CH$_3$ | 6-CH$_3$ | —C(CH$_3$)(CH$_2$Cl)$_2$ |
| | —(CH$_2$)$_2$—CH(OCH$_3$)—(CH$_2$)$_2$— | —CH$_3$ | —CH$_3$ | 6-CH$_3$ | —C(CH$_3$)$_2$—CH$_2$OCH$_3$ |
| | —(CH$_2$)$_2$—CH(OCH$_3$)—(CH$_2$)$_2$— | —CH$_3$ | —CH$_3$ | 6-CH$_3$ | —C(CH$_3$)—(CH$_2$—OCH$_3$)$_2$ |
| | —(CH$_2$)$_2$—CH(OCH$_3$)—(CH$_2$)$_2$— | —CH$_3$ | —CH$_3$ | 6-CH$_3$ | —CH=C(CH$_3$)$_2$ |
| | —(CH$_2$)$_2$—CH(OCH$_3$)—(CH$_2$)$_2$— | —CH$_3$ | —CH$_3$ | 6-CH$_3$ | cyclopropyl |
| | —(CH$_2$)$_2$—CH(OCH$_3$)—(CH$_2$)$_2$— | —CH$_3$ | —CH$_3$ | 6-CH$_3$ | cyclohexyl |
| | —(CH$_2$)$_2$—CH(OCH$_3$)—(CH$_2$)$_2$— | —CH$_3$ | —CH$_3$ | 6-CH$_3$ | 1-methylcyclohexyl |

TABLE 2-continued

| A | B | X | Y | $Z_n$ | $R^1$ |
|---|---|---|---|-------|-------|
| —$(CH_2)_2$—CH(OCH$_3$)—$(CH_2)_2$— | | —CH$_3$ | —CH$_3$ | 6-CH$_3$ | 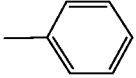 |
| —$(CH_2)_2$—CH(OCH$_3$)—$(CH_2)_2$— | | —CH$_3$ | —CH$_3$ | 6-CH$_3$ | 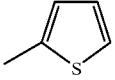 |
| —$(CH_2)_2$—CH(OCH$_3$)—$(CH_2)_2$— | | —CH$_3$ | —CH$_3$ | 6-CH$_3$ | 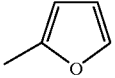 |
| —$(CH_2)_2$—CH(OCH$_3$)—$(CH_2)_2$— | | —CH$_3$ | —CH$_3$ | 6-CH$_3$ | 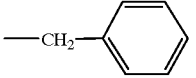 |
| —$(CH_2)_2$—CH(OCH$_3$)—$(CH_2)_2$— | | —CH$_3$ | —CH$_3$ | 6-CH$_3$ | 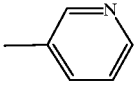 |

Table 3

Table 3 contains the compounds of the formula (Ib) in which A, B and $R^1$ have the meanings given in Table 2 and X and Y in each case represent chlorine and $Z_n$ represents hydrogen.

Table 4

Table 4 contains the compounds of the formula (Ib) in which A, B and $R^1$ have the meanings given in Table 2 and X and Y in each case represent CH$_3$ and $Z_n$ represents hydrogen.

In addition to the compounds mentioned in the preparation examples, the following 2-aryl-3-hydroxy-$\Delta^2$-cyclopentenone derivatives of the formula (Ic) may be mentioned specifically (Table 5):

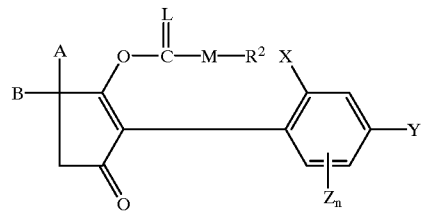

(Ic)

TABLE 5

| A | B | X | Y | $Z_n$ | L | M | $R^2$ |
|---|---|---|---|-------|---|---|-------|
| —CH$_3$ | —CH$_3$ | —CH$_3$ | —CH$_3$ | 6-CH$_3$ | O | O | —CH$_3$ |
| —C$_2$H$_5$ | —CH$_3$ | —CH$_3$ | —CH$_3$ | 6-CH$_3$ | O | O | —CH$_3$ |
| —CH(CH$_3$)$_2$ | —CH$_3$ | —CH$_3$ | —CH$_3$ | 6-CH$_3$ | O | O | —CH$_3$ |
| —(CH$_2$)$_4$— | | —CH$_3$ | —CH$_3$ | 6-CH$_3$ | O | O | —CH$_3$ |
| —(CH$_2$)$_5$— | | —CH$_3$ | —CH$_3$ | 6-CH$_3$ | O | O | —CH$_3$ |
| —(CH$_2$)$_6$— | | —CH$_3$ | —CH$_3$ | 6-CH$_3$ | O | O | —CH$_3$ |
| —CH$_2$—CH(CH$_3$)—(CH$_2$)$_3$— | | —CH$_3$ | —CH$_3$ | 6-CH$_3$ | O | O | —CH$_3$ |
| —(CH$_2$)$_2$—CH(CH$_3$)—(CH$_2$)$_2$— | | —CH$_3$ | —CH$_3$ | 6-CH$_3$ | O | O | —CH$_3$ |
| —(CH$_2$)$_2$—CH(C$_2$H$_5$)—(CH$_2$)$_2$— | | —CH$_3$ | —CH$_3$ | 6-CH$_3$ | O | O | —CH$_3$ |
| —(CH$_2$)$_2$—CH(OCH$_3$)—(CH$_2$)$_2$— | | —CH$_3$ | —CH$_3$ | 6-CH$_3$ | O | O | —CH$_3$ |
| —CH$_3$ | —CH$_3$ | —CH$_3$ | —CH$_3$ | 6-CH$_3$ | O | O | —C$_2$H$_5$ |
| —C$_2$H$_5$ | —CH$_3$ | —CH$_3$ | —CH$_3$ | 6-CH$_3$ | O | O | —C$_2$H$_5$ |
| —CH(CH$_3$)$_2$ | —CH$_3$ | —CH$_3$ | —CH$_3$ | 6-CH$_3$ | O | O | —C$_2$H$_5$ |
| —(CH$_2$)$_4$— | | —CH$_3$ | —CH$_3$ | 6-CH$_3$ | O | O | —C$_2$H$_5$ |
| —(CH$_2$)$_5$— | | —CH$_3$ | —CH$_3$ | 6-CH$_3$ | O | O | —C$_2$H$_5$ |
| —(CH$_2$)$_6$— | | —CH$_3$ | —CH$_3$ | 6-CH$_3$ | O | O | —C$_2$H$_5$ |

TABLE 5-continued

| A | B | X | Y | $Z_n$ | L | M | $R^2$ |
|---|---|---|---|---|---|---|---|
| | —CH₂—CH(CH₃)—(CH₂)₃— | —CH₃ | —CH₃ | 6-CH₃ | O | O | —C₂H₅ |
| | —(CH₂)₂—CH(CH₃)—(CH₂)₂— | —CH₃ | —CH₃ | 6-CH₃ | O | O | —C₂H₅ |
| | —(CH₂)₂—CH(C₂H₅)—(CH₂)₂— | —CH₃ | —CH₃ | 6-CH₃ | O | O | —C₂H₅ |
| | —(CH₂)₂—CH(OCH₃)—(CH₂)₂— | —CH₃ | —CH₃ | 6-CH₃ | O | O | —C₂H₅ |
| —CH₃ | —CH₃ | —CH₃ | —CH₃ | 6-CH₃ | O | O | —CH(CH₃)₂ |
| —C₂H₅ | —CH₃ | —CH₃ | —CH₃ | 6-CH₃ | O | O | —CH(CH₃)₂ |
| —CH(CH₃)₂ | —CH₃ | —CH₃ | —CH₃ | 6-CH₃ | O | O | —CH(CH₃)₂ |
| | —(CH₂)₄— | —CH₃ | —CH₃ | 6-CH₃ | O | O | —CH(CH₃)₂ |
| | —(CH₂)₅— | —CH₃ | —CH₃ | 6-CH₃ | O | O | —CH(CH₃)₂ |
| | —(CH₂)₆— | —CH₃ | —CH₃ | 6-CH₃ | O | O | —CH(CH₃)₂ |
| | —CH₂—CH(CH₃)—(CH₂)₃— | —CH₃ | —CH₃ | 6-CH₃ | O | O | —CH(CH₃)₂ |
| | —(CH₂)₂—CH(CH₃)—(CH₂)₂— | —CH₃ | —CH₃ | 6-CH₃ | O | O | —CH(CH₃)₂ |
| | —(CH₂)₂—CH(C₂H₅)—(CH₂)₂— | —CH₃ | —CH₃ | 6-CH₃ | O | O | —CH(CH₃)₂ |
| | —(CH₂)₂—CH(OCH₃)—(CH₂)₂— | —CH₃ | —CH₃ | 6-CH₃ | O | O | —CH(CH₃)₂ |
| —CH₃ | —CH₃ | —CH₃ | —CH₃ | 6-CH₃ | O | O | —CH₂—CH(CH₃)₂ |
| —C₂H₅ | —CH₃ | —CH₃ | —CH₃ | 6-CH₃ | O | O | —CH₂—CH(CH₃)₂ |
| —CH(CH₃)₂ | —CH₃ | —CH₃ | —CH₃ | 6-CH₃ | O | O | —CH₂—CH(CH₃)₂ |
| | —(CH₂)₄— | —CH₃ | —CH₃ | 6-CH₃ | O | O | —CH₂—CH(CH₃)₂ |
| | —(CH₂)₅— | —CH₃ | —CH₃ | 6-CH₃ | O | O | —CH₂—CH(CH₃)₂ |
| | —(CH₂)₆— | —CH₃ | —CH₃ | 6-CH₃ | O | O | —CH₂—CH(CH₃)₂ |
| | —CH₂—CH(CH₃)—(CH₂)₃— | —CH₃ | —CH₃ | 6-CH₃ | O | O | —CH₂—CH(CH₃)₂ |
| | —(CH₂)₂—CH(CH₃)—(CH₂)₂— | —CH₃ | —CH₃ | 6-CH₃ | O | O | —CH₂—CH(CH₃)₂ |
| | —(CH₂)₂—CH(C₂H₅)—(CH₂)₂— | —CH₃ | —CH₃ | 6-CH₃ | O | O | —CH₂—CH(CH₃)₂ |
| | —(CH₂)₂—CH(OCH₃)—(CH₂)₂— | —CH₃ | —CH₃ | 6-CH₃ | O | O | —CH₂—CH(CH₃)₂ |
| —CH₃ | —CH₃ | CH₃ | CH₃ | 6-CH₃ | O | O | —CH(CH₃)—C₂H₅ |
| —C₂H₅ | —CH₃ | CH₃ | CH₃ | 6-CH₃ | O | O | —CH(CH₃)—C₂H₅ |
| —CH(CH₃)₂ | —CH₃ | CH₃ | CH₃ | 6-CH₃ | O | O | —CH(CH₃)—C₂H₅ |
| | —(CH₂)₄— | CH₃ | CH₃ | 6-CH₃ | O | O | —CH(CH₃)—C₂H₅ |
| | —(CH₂)₅— | CH₃ | CH₃ | 6-CH₃ | O | O | —CH(CH₃)—C₂H₅ |
| | —(CH₂)₆— | CH₃ | CH₃ | 6-CH₃ | O | O | —CH(CH₃)—C₂H₅ |
| | —CH₂—CH(CH₃)—(CH₂)₃— | CH₃ | CH₃ | 6-CH₃ | O | O | —CH(CH₃)—C₂H₅ |
| | —(CH₂)₂—CH(CH₃)—(CH₂)₂— | CH₃ | CH₃ | 6-CH₃ | O | O | —CH(CH₃)—C₂H₅ |
| | —(CH₂)₂—CH(C₂H₅)—(CH₂)₂— | —CH₃ | —CH₃ | 6-CH₃ | O | O | —CH(CH₃)—C₂H₅ |
| | —(CH₂)₂—CH(OCH₃)—(CH₂)₂— | —CH₃ | —CH₃ | 6-CH₃ | O | O | —CH(CH₃)—C₂H₅ |
| —CH₃ | —CH₃ | —CH₃ | —CH₃ | 6-CH₃ | O | O | —CH₂—C(CH₃)₃ |
| —C₂H₅ | —CH₃ | —CH₃ | —CH₃ | 6-CH₃ | O | O | —CH₂—C(CH₃)₃ |
| —CH(CH₃)₂ | —CH₃ | —CH₃ | —CH₃ | 6-CH₃ | O | O | —CH₂—C(CH₃)₃ |
| | —(CH₂)₄— | —CH₃ | —CH₃ | 6-CH₃ | O | O | —CH₂—C(CH₃)₃ |
| | —(CH₂)₅— | —CH₃ | —CH₃ | 6-CH₃ | O | O | —CH₂—C(CH₃)₃ |
| | —(CH₂)₆— | —CH₃ | —CH₃ | 6-CH₃ | O | O | —CH₂—C(CH₃)₃ |
| | —CH₂—CH(CH₃)—(CH₂)₃— | —CH₃ | —CH₃ | 6-CH₃ | O | O | —CH₂—C(CH₃)₃ |
| | —(CH₂)₂—CH(CH₃)—(CH₂)₂— | —CH₃ | —CH₃ | 6-CH₃ | O | O | —CH₂—C(CH₃)₃ |

TABLE 5-continued

| A | B | X | Y | $Z_n$ | L | M | $R^2$ |
|---|---|---|---|---|---|---|---|
| —(CH$_2$)$_2$—CH(C$_2$H$_5$)—(CH$_2$)$_2$— | | —CH$_3$ | —CH$_3$ | 6-CH$_3$ | O | O | —CH$_2$—C(CH$_3$)$_3$ |
| —(CH$_2$)$_2$—CH(OCH$_3$)—(CH$_2$)$_2$— | | —CH$_3$ | —CH$_3$ | 6-CH$_3$ | O | O | —CH$_2$—C(CH$_3$)$_3$ |
| —CH$_3$ | —CH$_3$ | —CH$_3$ | —CH$_3$ | 6-CH$_3$ | O | O | —CH$_2$—C$_6$H$_5$ |
| —C$_2$H$_5$ | —CH$_3$ | —CH$_3$ | —CH$_3$ | 6-CH$_3$ | O | O | —CH$_2$—C$_6$H$_5$ |
| —CH(CH$_3$)$_2$ | —CH$_3$ | —CH$_3$ | —CH$_3$ | 6-CH$_3$ | O | O | —CH$_2$—C$_6$H$_5$ |
| —(CH$_2$)$_4$— | | —CH$_3$ | —CH$_3$ | 6-CH$_3$ | O | O | —CH$_2$—C$_6$H$_5$ |
| —(CH$_2$)$_5$— | | —CH$_3$ | —CH$_3$ | 6-CH$_3$ | O | O | —CH$_2$—C$_6$H$_5$ |
| —(CH$_2$)$_6$— | | —CH$_3$ | —CH$_3$ | 6-CH$_3$ | O | O | —CH$_2$—C$_6$H$_5$ |
| —CH$_2$—CH(CH$_3$)—(CH$_2$)$_3$— | | —CH$_3$ | —CH$_3$ | 6-CH$_3$ | O | O | —CH$_2$—C$_6$H$_5$ |
| —(CH$_2$)$_2$—CH(CH$_3$)—(CH$_2$)$_2$— | | —CH$_3$ | —CH$_3$ | 6-CH$_3$ | O | O | —CH$_2$—C$_6$H$_5$ |
| —(CH$_2$)$_2$—CH(C$_2$H$_5$)—(CH$_2$)$_2$— | | —CH$_3$ | —CH$_3$ | 6-CH$_3$ | O | O | —CH$_2$—C$_6$H$_5$ |
| —(CH$_2$)$_2$—CH(OCH$_3$)—(CH$_2$)$_2$— | | —CH$_3$ | —CH$_3$ | 6-CH$_3$ | O | O | —CH$_2$—C$_6$H$_5$ |
| —CH$_3$ | —CH$_3$ | —CH$_3$ | —CH$_3$ | 6-CH$_3$ | O | O | —CH$_2$—CH(C$_4$H$_9$)(C$_2$H$_5$) |
| —C$_2$H$_5$ | —CH$_3$ | —CH$_3$ | —CH$_3$ | 6-CH$_3$ | O | O | —CH$_2$—CH(C$_4$H$_9$)(C$_2$H$_5$) |
| —CH(CH$_3$)$_2$ | —CH$_3$ | —CH$_3$ | —CH$_3$ | 6-CH$_3$ | O | O | —CH$_2$—CH(C$_4$H$_9$)(C$_2$H$_5$) |

TABLE 5-continued

| A | B | X | Y | $Z_n$ | L | M | $R^2$ |
|---|---|---|---|---|---|---|---|
|  | —(CH$_2$)$_4$— | —CH$_3$ | —CH$_3$ | 6-CH$_3$ | O | O | —CH$_2$—CH(C$_4$H$_9$)(C$_2$H$_5$) |
|  | —(CH$_2$)$_5$— | —CH$_3$ | —CH$_3$ | 6-CH$_3$ | O | O | —CH$_2$—CH(C$_4$H$_9$)(C$_2$H$_5$) |
|  | —(CH$_2$)$_6$— | —CH$_3$ | —CH$_3$ | 6-CH$_3$ | O | O | —CH$_2$—CH(C$_4$H$_9$)(C$_2$H$_5$) |
|  | —CH$_2$—CH(CH$_3$)—(CH$_2$)$_3$— | —CH$_3$ | —CH$_3$ | 6-CH$_3$ | O | O | —CH$_2$—CH(C$_4$H$_9$)(C$_2$H$_5$) |
|  | —(CH$_2$)$_2$—CH(CH$_3$)—(CH$_2$)$_2$— | —CH$_3$ | —CH$_3$ | 6-CH$_3$ | O | O | —CH$_2$—CH(C$_4$H$_9$)(C$_2$H$_5$) |
|  | —(CH$_2$)$_2$—CH(C$_2$H$_5$)—(CH$_2$)$_2$— | —CH$_3$ | —CH$_3$ | 6-CH$_3$ | O | O | —CH$_2$—CH(C$_4$H$_9$)(C$_2$H$_5$) |
|  | —(CH$_2$)$_2$—CH(OCH$_3$)—(CH$_2$)$_2$— | —CH$_3$ | —CH$_3$ | 6-CH$_3$ | O | O | —CH$_2$—CH(C$_4$H$_9$)(C$_2$H$_5$) |
| —CH$_3$ | —CH$_3$ | —CH$_3$ | —CH$_3$ | 6-CH$_3$ | O | O | —C$_6$H$_5$ |
| —C$_2$H$_5$ | —CH$_3$ | —CH$_3$ | —CH$_3$ | 6-CH$_3$ | O | O | —C$_6$H$_5$ |
| —CH(CH$_3$)$_2$ | —CH$_3$ | —CH$_3$ | —CH$_3$ | 6-CH$_3$ | O | O | —C$_6$H$_5$ |
|  | —(CH$_2$)$_4$— | —CH$_3$ | —CH$_3$ | 6-CH$_3$ | O | O | —C$_6$H$_5$ |
|  | —(CH$_2$)$_5$— | —CH$_3$ | —CH$_3$ | 6-CH$_3$ | O | O | —C$_6$H$_5$ |
|  | —(CH$_2$)$_6$— | —CH$_3$ | —CH$_3$ | 6-CH$_3$ | O | O | —C$_6$H$_5$ |
|  | —CH$_2$—CH(CH$_3$)—(CH$_2$)$_3$— | —CH$_3$ | —CH$_3$ | 6-CH$_3$ | O | O | —C$_6$H$_5$ |
|  | —(CH$_2$)$_2$—CH(CH$_3$)—(CH$_2$)$_2$— | —CH$_3$ | —CH$_3$ | 6-CH$_3$ | O | O | —C$_6$H$_5$ |

TABLE 5-continued

| A | B | X | Y | $Z_n$ | L | M | $R^2$ |
|---|---|---|---|---|---|---|---|
| —(CH₂)₂—CH(C₂H₅)—(CH₂)₂— | | —CH₃ | —CH₃ | 6-CH₃ | O | O | 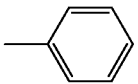 |
| —(CH₂)₂—CH(OCH₃)—(CH₂)₂— | | —CH₃ | —CH₃ | 6-CH₃ | O | O | 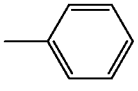 |
| —CH₃ | —CH₃ | —CH₃ | —CH₃ | 6-CH₃ | O | S | —C₂H₅ |
| —C₂H₅ | —CH₃ | —CH₃ | —CH₃ | 6-CH₃ | O | S | —C₂H₅ |
| —CH(CH₃)₂ | —CH₃ | —CH₃ | —CH₃ | 6-CH₃ | O | S | —C₂H₅ |
| —(CH₂)₄— | | —CH₃ | —CH₃ | 6-CH₃ | O | S | —C₂H₅ |
| —(CH₂)₅— | | —CH₃ | —CH₃ | 6-CH₃ | O | S | —C₂H₅ |
| —(CH₂)₆— | | —CH₃ | —CH₃ | 6-CH₃ | O | S | —C₂H₅ |
| —CH₂—CH(CH₃)—(CH₂)₃— | | —CH₃ | —CH₃ | 6-CH₃ | O | S | —C₂H₅ |
| —(CH₂)₂—CH(CH₃)—(CH₂)₂— | | —CH₃ | —CH₃ | 6-CH₃ | O | S | —C₂H₅ |
| —(CH₂)₂—CH(C₂H₅)—(CH₂)₂— | | —CH₃ | —CH₃ | 6-CH₃ | O | S | —C₂H₅ |
| —(CH₂)₂—CH(OCH₃)—(CH₂)₂— | | —CH₃ | —CH₃ | 6-CH₃ | O | S | —C₂H₅ |
| —CH₃ | —CH₃ | —CH₃ | —CH₃ | 6-CH₃ | O | S | —CH(CH₃)₂ |
| —C₂H₅ | —CH₃ | —CH₃ | —CH₃ | 6-CH₃ | O | S | —CH(CH₃)₂ |
| —CH(CH₃)₂ | —CH₃ | —CH₃ | —CH₃ | 6-CH₃ | O | S | —CH(CH₃)₂ |
| —CF₃ | —CH₃ | —CH₃ | —CH₃ | 6-CH₃ | O | S | —CH(CH₃)₂ |
| —(CH₂)₄— | | —CH₃ | —CH₃ | 6-CH₃ | O | S | —CH(CH₃)₂ |
| —(CH₂)₅— | | —CH₃ | —CH₃ | 6-CH₃ | O | S | —CH(CH₃)₂ |
| —(CH₂)₆— | | —CH₃ | —CH₃ | 6-CH₃ | O | S | —CH(CH₃)₂ |
| —CH₂—CH(CH₃)—(CH₂)₃— | | —CH₃ | —CH₃ | 6-CH₃ | O | S | —CH(CH₃)₂ |
| —(CH₂)₂—CH(CH₃)—(CH₂)₂— | | —CH₃ | —CH₃ | 6-CH₃ | O | S | —CH(CH₃)₂ |
| —(CH₂)₂—CH(C₂H₅)—(CH₂)₂— | | —CH₃ | —CH₃ | 6-CH₃ | O | S | —CH(CH₃)₂ |
| —(CH₂)₂—CH(OCH₃)—(CH₂)₂— | | —CH₃ | —CH₃ | 6-CH₃ | O | S | —CH(CH₃)₂ |

Table 6

Table 6 contains the compounds of the formula (Ic) in which A, B, L, M and $R^2$ have the meanings given in Table 5 and X and Y in each case represent chlorine and $Z_n$ represents hydrogen.

Table 7

Table 7 contains the compounds of the formula (Ic) in which A, B, L, M and $R^2$ have the meanings given in Table 5 and X and Y in each case represent $CH_3$ and $Z_n$ represents hydrogen.

In addition to the compounds mentioned in the preparation examples, the following 2-aryl-3-hydroxy-$\Delta^2$-cyclopentenone derivatives of the formula (Id) may be mentioned specifically:

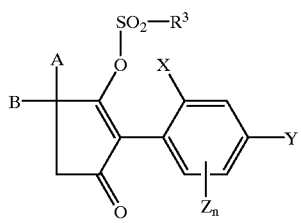

(Id)

TABLE 8

| A | B | X | Y | $Z_n$ | $R^3$ |
|---|---|---|---|---|---|
| —(CH$_2$)$_5$— | CH$_3$ | CH$_3$ | 6-CH$_3$ | | phenyl |
| —(CH$_2$)$_5$— | CH$_3$ | CH$_3$ | 6-CH$_3$ | | 4-Cl-phenyl |
| —(CH$_2$)$_5$— | CH$_3$ | CH$_3$ | 6-CH$_3$ | CH$_3$ | |

In addition to the compounds mentioned in the preparation examples, the following 2-aryl-3-hydroxy-Δ²-cyclopentenone derivatives of the formula (Ie) may be mentioned specifically:

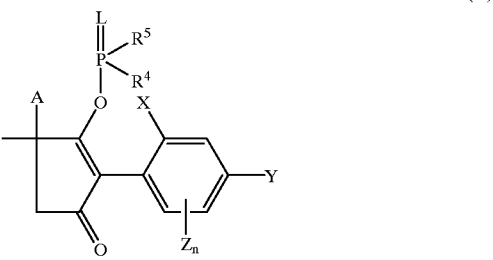

(Ie)

TABLE 9

| A | B | X | Y | $Z_n$ | L | $R^4$ | $R^5$ |
|---|---|---|---|---|---|---|---|
| —(CH$_2$)$_5$— | CH$_3$ | CH$_3$ | 6-CH$_3$ | S | CF$_3$CH$_2$O— | |
| —(CH$_2$)$_5$— | CH$_3$ | CH$_3$ | 6-CH$_3$ | O | CH$_3$—O— | CH$_3$ |
| —(CH$_2$)$_5$— | CH$_3$ | CH$_3$ | 6-CH$_3$ | O | CH$_3$—O— | C$_2$H$_5$—S— / (CH$_3$)$_2$CH—S— |
| —(CH$_2$)$_5$— | CH$_3$ | CH$_3$ | 6-CH$_3$ | O | CH$_3$—O— | (C$_2$H$_5$)(CH$_3$)CH—S— |
| —(CH$_2$)$_5$— | CH$_3$ | CH$_3$ | 6-CH$_3$ | O | C$_2$H$_5$O— | |
| —(CH$_2$)$_5$— | CH$_3$ | CH$_3$ | 6-CH$_3$ | O | C$_2$H$_5$O— | C$_2$H$_5$—S— / (CH$_3$)$_2$CH—S— |
| —(CH$_2$)$_5$— | CH$_3$ | CH$_3$ | 6-CH$_3$ | O | C$_2$H$_5$O | (C$_2$H$_5$)(CH$_3$)CH—S— |

In addition to the compounds mentioned in the preparation examples, the following 2-aryl-3-hydroxy-Δ²-cyclopentenone derivatives of the formula (If) may be mentioned specifically (Table 10):

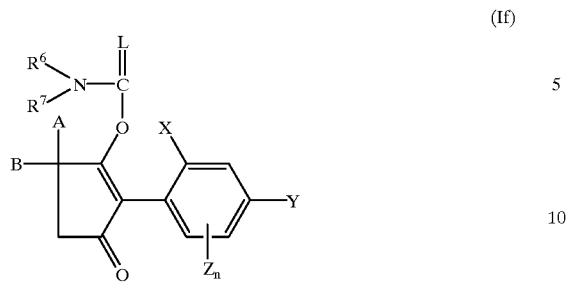

(If)

In addition to the compounds mentioned in the preparation examples, the following 2-aryl-3-hydroxy-Δ²-cyclopentenone derivatives of the formula (Ig) may be mentioned specifically (Table 11):

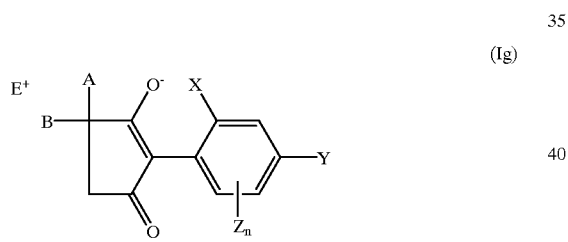

(Ig)

TABLE 10

| A | B | X | Y | $Z_n$ | L | $R^6$ | $R^7$ |
|---|---|---|---|---|---|---|---|
| —$(CH_2)_5$— | $CH_3$ | $CH_3$ | $CH_3$ | 6-$CH_3$ | O | $CH_3$— | $CH_3$— |
| —$(CH_2)_5$— | $CH_3$ | $CH_3$ | $CH_3$ | 6-$CH_3$ | S | $CH_3$— | $CH_3$— |
| —$(CH_2)_5$— | $CH_3$ | $CH_3$ | $CH_3$ | 6-$CH_3$ | O | $CH_2$=$CHCH_2$— | $CH_2$=$CH$—$CH_2$— |
| —$(CH_2)_5$— | $CH_3$ | $CH_3$ | $CH_3$ | 6-$CH_3$ | O | —$(CH_2)_2$—O—$(CH_2)_2$— | |
| —$(CH_2)_5$— | $CH_3$ | $CH_3$ | $CH_3$ | 6-$CH_3$ | O | —$(CH_2)_5$— | |
| —$(CH_2)_5$— | $CH_3$ | $CH_3$ | $CH_3$ | 6-$CH_3$ | O | (phenyl) | $C_2H_5$— |

TABLE 11

| A | B | X | Y | $Z_n$ | E |
|---|---|---|---|---|---|
| —$CH_3$ | $CH_3$ | —$CH_3$ | —$CH_3$ | 6-$CH_3$ | $NH_4$ |
| —$CH_3$ | —$CH_3$ | —$CH_3$ | —$CH_3$ | 6-$CH_3$ | Na |
| —$C_2H_5$ | —$CH_3$ | —$CH_3$ | —$CH_3$ | 6-$CH_3$ | Na |
| —$CH(CH_3)_2$ | —$CH_3$ | —$CH_3$ | —$CH_3$ | 6-$CH_3$ | Na |
| —$CF_3$ | —$CH_3$ | —$CH_3$ | —$CH_3$ | 6-$CH_3$ | Na |
| —$(CH_2)_4$— | | —$CH_3$ | —$CH_3$ | 6-$CH_3$ | Na |
| —$(CH_2)_5$— | | —$CH_3$ | —$CH_3$ | 6-$CH_3$ | Na |
| —$(CH_2)_6$— | | —$CH_3$ | —$CH_3$ | 6-$CH_3$ | Na |
| —$CH_2$—$CH(CH_3)$—$(CH_2)_3$— | | —$CH_3$ | —$CH_3$ | 6-$CH_3$ | Na |
| —$(CH_2)_2$—$CH(CH_3)$—$(CH_2)_2$— | | —$CH_3$ | —$CH_3$ | 6-$CH_3$ | Na |
| —$(CH_2)_2$—CH($C_2H_5$)—$(CH_2)_2$— | | —$CH_3$ | —$CH_3$ | 6-$CH_3$ | Na |

TABLE 11-continued

| A | B | X | Y | $Z_n$ | E |
|---|---|---|---|---|---|
| —(CH$_2$)$_2$—CH(OCH$_3$)—(CH$_2$)$_2$— | | —CH$_3$ | —CH$_3$ | 6-CH$_3$ | Na |
| —CH$_3$ | —CH$_3$ | —CH$_3$ | —CH$_3$ | 6-CH$_3$ | i-C$_3$H$_7$NH$_3$ |
| —C$_2$H$_5$ | —CH$_3$ | —CH$_3$ | —CH$_3$ | 6-CH$_3$ | i-C$_3$H$_7$NH$_3$ |
| —CH(CH$_3$)$_2$ | —CH$_3$ | —CH$_3$ | —CH$_3$ | 6-CH$_3$ | i-C$_3$H$_7$NH$_3$ |
| —CF$_3$ | —CH$_3$ | —CH$_3$ | —CH$_3$ | 6-CH$_3$ | i-C$_3$H$_7$NH$_3$ |
| | —(CH$_2$)$_4$— | —CH$_3$ | —CH$_3$ | 6-CH$_3$ | i-C$_3$H$_7$NH$_3$ |
| | —(CH$_2$)$_5$— | —CH$_3$ | —CH$_3$ | 6-CH$_3$ | i-C$_3$H$_7$NH$_3$ |
| | —(CH$_2$)$_6$— | —CH$_3$ | —CH$_3$ | 6-CH$_3$ | i-C$_3$H$_7$NH$_3$ |
| —CH$_2$—CH(CH$_3$)—(CH$_2$)$_3$— | | —CH$_3$ | —CH$_3$ | 6-CH$_3$ | i-C$_3$H$_7$NH$_3$ |
| —(CH$_2$)$_2$—CH(CH$_3$)—(CH$_2$)$_2$— | | —CH$_3$ | —CH$_3$ | 6-CH$_3$ | i-C$_3$H$_7$NH$_3$ |
| —(CH$_2$)$_2$—CH(C$_2$H$_5$)—(CH$_2$)$_2$— | | —CH$_3$ | —CH$_3$ | 6-CH$_3$ | i-C$_3$H$_7$NH$_3$ |
| —(CH$_2$)$_2$—CH(OCH$_3$)—(CH$_2$)$_2$— | | —CH$_3$ | —CH$_3$ | 6-CH$_3$ | i-C$_3$H$_7$NH$_3$ |

Table 12

Table 12 contains the compounds of the formula (Ig) in which A, B and E have the meanings given in Table 11 and X and Y in each case represent chlorine and $Z_n$ represents hydrogen Table 13

Table 13 contains the compounds of the formula (Ig) in which A, B and E have the meanings given in Table 11 and X and Y in each case represent CH$_3$ and $Z_n$ represents hydrogen.

If ethyl 5-(2,6-dichlorophenyl)-2,2-dimethyl-4-oxo-valerate is used according to process (A), the course of the process according to the invention can be represented by the following equation:

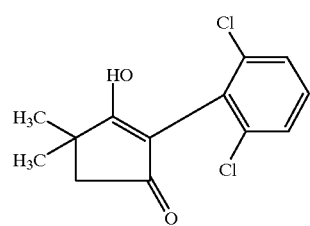

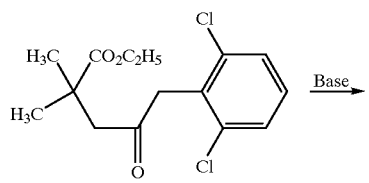

If 2-(2,4,6-trimethylphenyl)-3-hydroxy-4,4-dimethyl-Δ$^2$-cyclopentenone and pivaloyl chloride are used as starting material according to process (B) (version α), the course of the process according to the invention can be represented by the following equation:

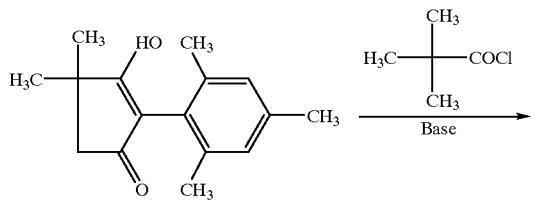

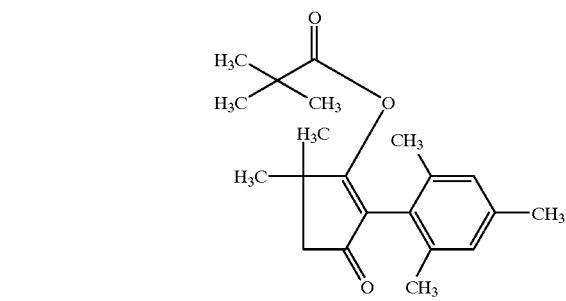

If 2-(2,4-dimethylphenyl)-3-hydroxy-4-methyl-4-phenyl-Δ$^2$-cyclopentenone and acetic anhydride are used as starting compounds according to process (B) (version B), the course of the process according to the invention can be represented by the following equation:

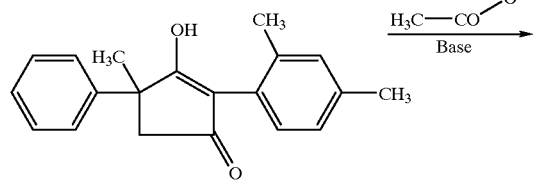

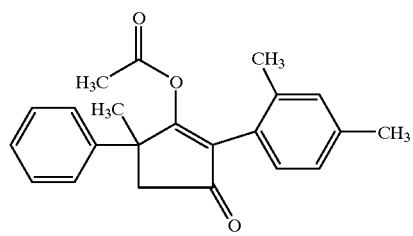

If 2-(2,4-dichlorophenyl)-3-hydroxy-4-isopropyl-4methyl-Δ²-cyclopentenone and ethoxyethyl chloroformate are used as starting compounds according to process (C), the course of the process according to the invention can be represented by the following equation:

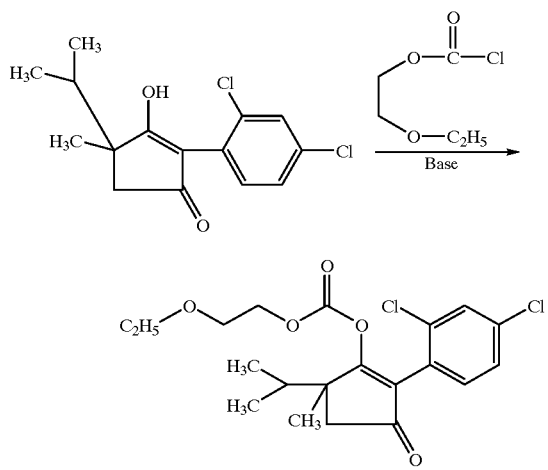

If 2-(2,4,6-trimethylphenyl)-3-hydroxy-4-ethyl-4-methyl-Δ²-cyclopentenone and methyl chloromonothioformate are used as starting substances according to process (D$_\alpha$), the course of the reaction can be represented as follows:

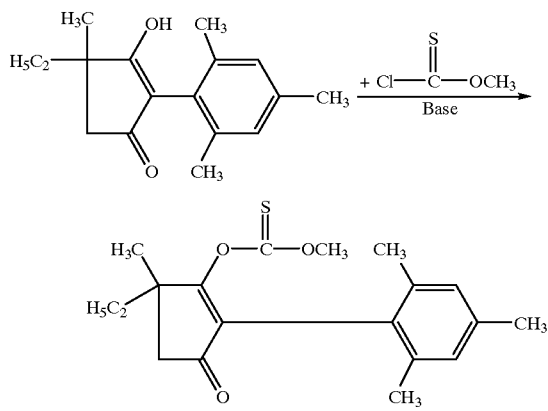

If 2-(2,4,6-trimethylphenyl)-3-hydroxy4,4-pentamethylene-Δ²-cyclopentenone, carbon disulphide and methyl iodide are used as starting components according to process (D$_\beta$), the course of the reaction can be represented as follows:

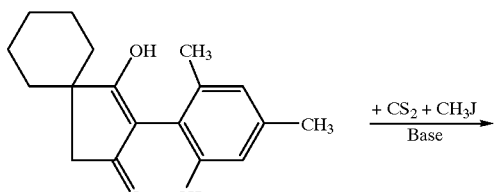

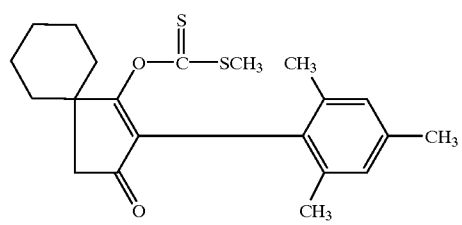

If 2-(2,4,6-trimethylphenyl)-3-hydroxy-4,4-(3-methoxy)-pentamethylene-Δ²-cyclopentenone and methanesulphonyl chloride are used as starting substance according to process (E), the course of the reaction can be represented by the following equation:

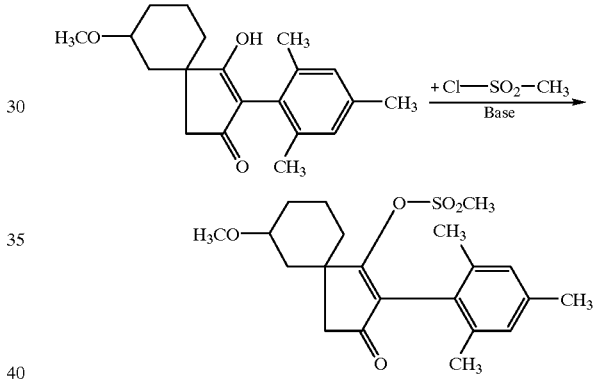

If 2-(2,4,6-trimethylphenyl)-3-hydroxy-4,4-dimethyl-Δ²-cyclopentenone and methanethio-phosphonic acid chloride-(2,2,2-trifluoroethyl ester) are used as starting substances according to process (F), the course of the reaction can be represented by the following equation:

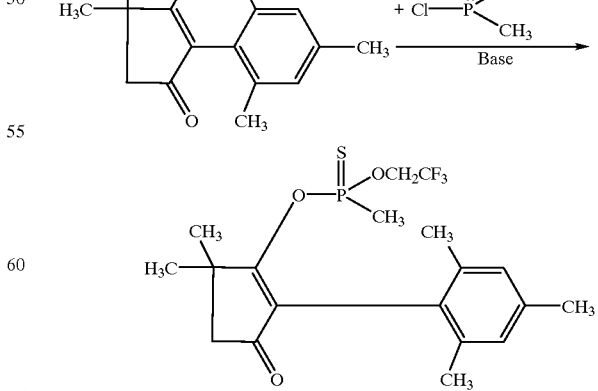

If 2-(2,4,6-trimethylphenyl)-3-hydroxy-4,4-tetraethylene-$\Delta^2$-cyclopentenone and ethyl isocyanate are used as starting substances according to process ($G_\alpha$), the course of the reaction can be represented by the following equation:

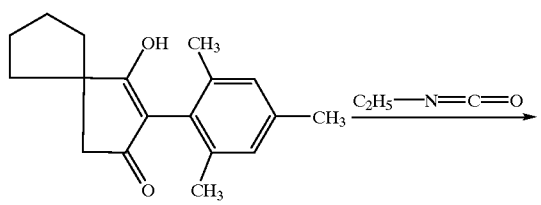

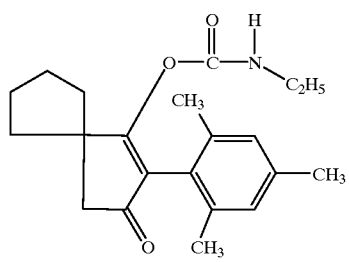

If 2-(2,4,6-trimethylphenyl)-3-hydroxy-4-trifluoromethyl-4-methyl-$\Delta^2$-cyclopentenone and dimethylcarbamoyl chloride are used as starting substances according to process ($G_\beta$), the course of the reaction can be represented by the following scheme:

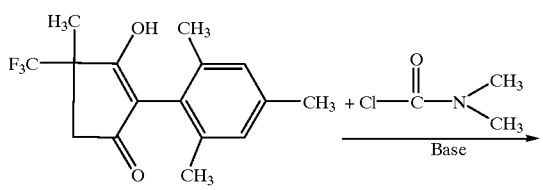

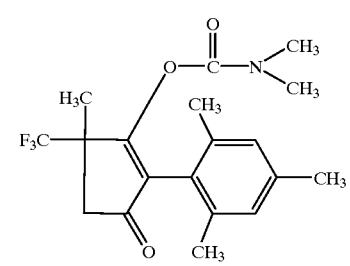

If 2-(2,4,6-trimethylphenyl)-3-hydroxy-4,4-dimethyl-$\Delta^2$-cyclopentenone and NaOH are used as components according to process (H), the course of the process according to the invention can be represented by the following equation:

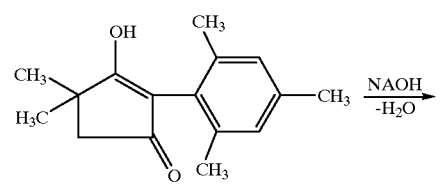

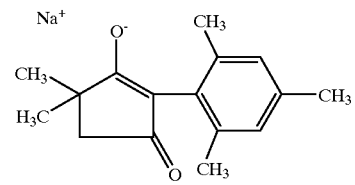

The compounds of the formula (II)

(II)

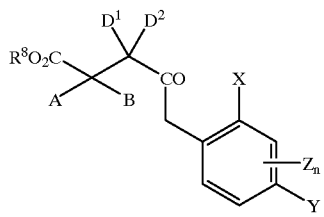

in which

A, B, $D^1$, $D^2$, X, Y, Z, n and $R^8$ have the abovementioned meaning, required as starting substances in the above process (A) are novel.

They can be prepared by methods which are known in principle.

The 5-aryl-4-ketocarboxylic acid esters of the formula (II) are obtained, for example, when 5-aryl-4-ketocarboxylic acids of the formula (XIV)

(XIV)

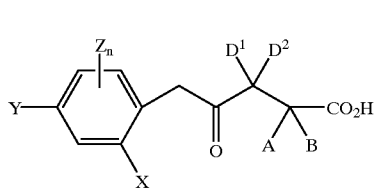

in which

X, Y, Z, A, B, $D^1$, $D^2$ and n have the abovementioned meaning, are esterified (cf. for example, Organikum, 15th Edition, Berlin, 1977, page 499).

The 5-aryl-4-ketocarboxylic acids of the formula (XIV)

(XIV)

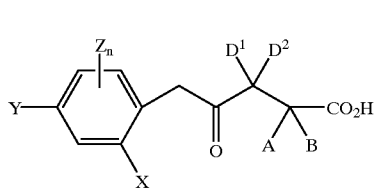

in which

A, B, $D^1$, $D^2$, X, Y, Z and n have the abovementioned meaning, are novel, but can be prepared by methods which are known in principle.

The 5-aryl-4-ketocarboxylic acids of the formula (XIV) are obtained, for example, when carboxylic acid anhydrides of the formula (XV)

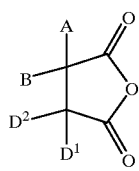
(XV)

in which

A, B, D$^1$ and D$^2$ have the abovementioned meaning, are reacted with organometallic compounds of the formula (XVI)

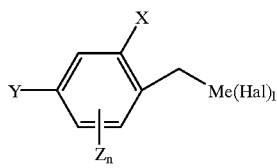
(XVI)

in which

X, Y, Z and n have the abovementioned meaning,

Me represents mono- or divalent metal ions, for example of lithium or magnesium, Hal represents chlorine or bromine and l represents a number 0 or 1 in the presence of a diluent (cf., for example, Organikum, 15th Edition, Berlin, 1977, Page 623).

The compounds (XV) and (XVI) are known in some cases and/or can be prepared in a simple manner by known processes (cf., for example, Organikum, 15th Edition, Berlin, 1977, pages 525, 526 and 623).

5-Aryl-4-ketocarboxylic acids of the formula (XIV)

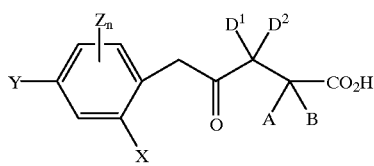
(XIV)

in which

A, B, D$^1$, D$^2$, X, Y, Z and n have the abovementioned meaning, furthermore are obtained when 2-phenyl-3-oxo-adipic acid esters of the formula

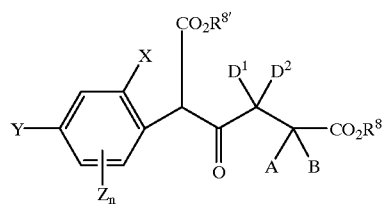
(XVII)

in which

A, B, D$^1$, D$^2$, X, Y, Z and n have the abovementioned meaning and

R$^8$ and R$^{8'}$ represent alkyl (in particular C$_1$–C$_8$-alkyl), are decarboxylated, if appropriate in the presence of a diluent and if appropriate in the presence of a base or acid (cf., for example, Organikum, 15th Edition, Berlin, 1977, page 519 to 521).

The compounds of the formula (XVII)

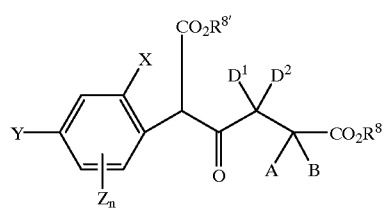
(XVII)

in which

A, B, D$^1$, D$^2$, X, Y, Z, R$^8$, R$^{8'}$ and n have the abovementioned meaning, are novel.

The compounds of the formula (XVII) are obtained, for example, when dicarboxylic acid half-ester chlorides of the formula (XVIII),

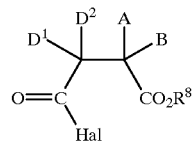
(XVIII)

in which

A, B, D$^1$, D$^2$ and R$^8$ have the abovementioned meaning and Hal represents chlorine or bromine, are acylated with a phenylacetic acid ester of the formula (XIX)

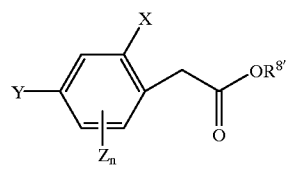
(XIX)

in which

X, Y, Z, R$^{8'}$ and n have the abovementioned meaning, in the presence of a diluent and in the presence of a base (cf., for example, M. S. Chambers, E. J. Thomas, D. J. Williams, J. Chem. Soc. Chem. Commun., (1987), 1228).

The compounds of the formulae (XVIII) and (XIX) are generally known compounds of Organic Chemistry and/or can be prepared in a simple manner by methods known in principle.

The process (A) is characterized in that compounds of the formula (II) in which A, B, $D^1$, $D^2$, Y, Z, n and $R^8$ have the abovementioned meaning are subjected to an intramolecular condensation reaction in the presence of bases.

Diluents which can be employed in process (A) according to the invention are all the organic solvents which are inert towards the reaction participants. Solvents which can preferably be used are hydrocarbons, such as toluene and xylene, and furthermore ethers, such as dibutyl ether, tetrahydrofuiran, dioxane, glycol dimethyl ether and diglycol dimethyl ether, and furthermore polar solvents, such as dimethyl sulphoxide, sulpholane, dimethylformamide and N-methyl-pyrrolidone. Alcohols, such as methanol, ethanol, propanol, iso-propanol, butanol, isobutanol, tert-butanol, can moreover be employed.

Bases (deprotonating agents) which can be employed in carrying out process (A) according to the invention are all the customary proton acceptors. Proton acceptors which can preferably be used as alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be employed in the presence of phase transfer catalysts, such as, for example, triethylbenzylammonium chloride, tetrabutyl-ammonium bromide, Adogen 464 (methyltrialkyl($C_8$–$C_{10}$)ammonium chloride) or TDA 1 (tris-(methoxyethoxyethyl)-amine). Alkali metals, such as sodium or potassium, can moreover be used. It is furthermore possible to employ alkali metal and alkaline earth metal amides and hydrides, such as sodium amide, sodium hydride and calcium hydride, and in addition also alkali metal alcoholates, such as sodium methylate, sodium ethylate and potassium tert-butylate.

The reaction temperatures can be varied within a substantial range in carrying out process (A) according to the invention. The reaction is in general carried out at temperatures between 0° C. and 250° C., preferably between 50° C. and 150° C.

Process (A) according to the invention is in general carried out under normal pressure.

In carrying out process (A) according to the invention, the reaction components of the formula (II) and the deprotonating bases are in general employed in approximately equimolar amounts. However, it is also possible to use one or other of the components in a relatively large excess (up to 3 mol).

Process (Bα) is characterized in that compounds of the formula (Ia) are reacted with carboxylic acid halides of the formula (III).

Diluents which can be employed in process (Bα) according to the invention are all the solvents which are inert towards the acid halides. Solvents which can preferably be used are hydrocarbons, such as benzine, benzene, toluene, xylene and tetralin, and furthermore halogenated hydrocarbons, such as methylene chloride, chloroform, carbonated tetrachloride, chlorobenzene and o-dichlorobenzene, and in addition ketones, such as acetone and methyl isopropyl ketone, and furthermore ethers, such as diethyl ether, methyl tert-butyl ether, tetra-hydrofuran and dioxane, and additionally carboxylic acid esters, such as ethyl acetate, and also strongly polar solvents, such as dimethyl sulphoxide and sulpholane. If the stability of the acid halide to hydrolysis allows, the reaction can also be carried out in the presence of water.

Possible acid-binding agents in the reaction by process (Bα) according to the invention are all the customary acid acceptors. Acid acceptors which can preferably be used are tertiary amines, such as triethylamine, pyridine, diazabiyclooctane (DABCO), diazabicycloundecane (DBU), diazabicyclononene (DBN), Hünig base and N,N-dimethyl aniline, and furthermore alkaline earth metal oxides, such as magnesium oxide and calcium oxide, and additionally alkali metal and alkaline earth metal carbonates, such as sodium carbonate, potassium carbonate and calcium carbonate.

The reaction temperatures can be varied within a substantial range in process (Bα) according to the invention. The reaction is in general carried out at temperatures between −20° C. and +150° C., preferably between 0° C. and 100° C.

In carrying out process (Bα) according to the invention, the starting substances of the formula (Ia) and the carboxylic acid halide of the formula (III) are in general used in approximately equivalent amounts. However, it is also possible to employ the carboxylic acid halide in a relatively large excess (up to 5 mol). Working up is carried out by customary methods.

Process (Bβ) is characterized in that compounds of the formula (Ia) are reacted with carboxylic acid anhydrides of the formula (IV).

Diluents which can be used in process (Bβ) according to the invention are preferably those diluents which are also preferably possible when acid halides are used. In addition, a carboxylic acid anhydride employed in excess can also simultaneously function as the diluent.

The reaction temperatures can be varied within a substantial range in process (Bβ) according to the invention. The reaction is in general carried out at temperatures between −20° C. and +150° C., preferably between 0C and 100° C.

In carrying out the process according to the invention, the starting substances of the formula (Ia) and the carboxylic acid anhydride of the formula (IV) are in general used in approximately equivalent amounts. However, it is also possible to employ the carboxylic acid anhydride in a relatively large excess (up to 5 mol). Working up is carried out by customary methods.

In general, a procedure is followed in which the diluent and the carboxylic acid anhydride present in excess, as well as the carboxylic acid formed, are removed by distillation or by washing with an organic solvent or with water.

Process (C) is characterized in that compounds of the formula (Ia) are reacted with chloroformic acid esters or chloroformic acid thiol esters of the formula (V).

Possible acid-binding agents in the reaction by process (C) according to the invention are all the customary acid acceptors. Acid acceptors which can preferably be used are tertiary amines, such as triethylamine, pyridine, DABCO, DBN, DBU, Hümig base and N,N-dimethyl aniline, and furthermore alkaline earth metal oxides, such as magnesium oxide and calcium oxide, and in addition alkali metal and alkaline earth metal carbonates, such as sodium carbonate, potassium carbonate and calcium carbonate.

Diluents which can be employed in process (C) according to the invention are all the solvents which are inert towards the chloroformic acid esters or chloroformic acid thiol esters. Solvents which can preferably be used are hydrocarbons, such as benzine, benzene, toluene, xylene and tetralin, and furthermore halogenated hydrocarbons, such as methylene chloride, chloroform, carbon tetrachloride, chlorobenzene and o-dichlorobenzene, and in addition ketones, such as acetone and methyl isopropyl ketone, and moreover ethers, such as diethyl ether, tetrahydrofuran and dioxane, and additionally carboxylic acid esters, such as ethyl acetate, and also strongly polar solvents, such as dimethyl sulphoxide and sulpholane.

The reaction temperatures can be varied within a substantial range in carrying out process (C) according to the invention. If the reaction is carried out in the presence of a diluent and an acid-binding agent, the reaction temperatures are in general between −20° C. and +100° C., preferably between 0° C. and 50° C.

Process (C) according to the invention is in general carried out under normal pressure.

In carrying out process (C) according to the invention, the starting substances of the formula (Ia) and the corresponding chloroformic acid esters or chloroformic acid thiol esters of the formula (V) are in general used in approximately equivalent amounts. However, it is also possible to employ one or other of the components in a relatively large excess (up to 2 mol). Working up is then carried out by customary methods. In general, a procedure is followed in which salts which have precipitated out are removed and the reaction mixture which remains is concentrated by stripping off the diluent.

In preparation process (Dα), about 1 mol of chloromonothioformic acid ester or chlorodithioformic acid ester of the formula (VI) is reacted per mol of starting compound of the formula (Ia) at 0 to 120° C., preferably at 20 to 60° C.

Possible diluents which are optionally added are all the inert polar organic solvents, such as halogenohydrocarbons, nitrites, carboxylic acid esters, ethers, amides, sulphones and sulphoxides.

Acetonitrile, ethyl acetate, dimethyl sulphoxide, tetrahydrofuran, dimethylformamide or methylene chloride are preferably employed.

If, in a preferred embodiment, the enolate salt of the compound of the formula (Ia) is prepared by addition of strong deprotonating agents, such as, for example, sodium hydride or potassium tert-butylate, further addition of acid-binding agents can be omitted.

If acid-binding agents are employed, the customary inorganic or organic bases are possible, and sodium hydroxide, sodium carbonate, potassium carbonate, pyridine and triethylamine may be listed as examples.

The reaction can be carried out under normal pressure or under increased pressure, and is preferably carried out under normal pressure. Working up is carried out by customary methods.

In preparation process (Dβ), the equimolar amount or an excess of carbon disulphide is added per mol of starting compound of the formula (II). This reaction is preferably carried out at temperatures from 0 to 50° C. and in particular at 20 to 30° C.

If appropriate, process (Dβ) is carried out in the presence of a base.

Bases which can be employed in process (DO are all the customary proton acceptors. Proton acceptors which can preferably be used are alkali metal hydrides, alkali metal alcoholates, alkali metal or alkaline earth metal carbonates or bicarbonates or nitrogen bases. Examples which may be mentioned are sodium hydride, sodium methanolate, sodium hydroxide, calcium hydroxide, potassium carbonate, sodium bicarbonate, triethylamine, dibenzylamine, diisopropylamine, pyridine, quinoline, diazabicyclooctane (DABCO), diazabicyclononene (DBN) and diazabicycloundecene (DBU).

Diluents which can be used in this process are all the customary solvents.

Solvents which can preferably be used are aromatic hydrocarbons, such as benzene or toluene, alcohols, such as methanol, ethanol, isopropanol or ethylene glycol, nitriles, such as acetonitrile, ethers, such as tetrahydrofuran or dioxane, amides, such as dimethylformamide, or other polar solvents, such as dimethyl sulphoxide or sulpholane.

It is often expedient first to prepare the corresponding salt from the compound of the formula (Ia) by addition of a deprotonating agent (such as, for example, potassium tert-butylate or sodium hydride). The compound of the formula (Ia) is reacted with carbon disulphide until the formation of the intermediate compound has ended, for example after the mixture has been stirred at room temperature for several hours.

The further reaction with the alkyl halide of the formula (VII) is preferably carried out at 0 to 70° C., and in particular at 20 to 50° C. At least the equimolar amount of alkyl halide is employed for this reaction.

The reaction is carried out under normal pressure or under increased pressure, preferably under normal pressure.

Working up is again carried out by customary methods.

In preparation process (E), about 1 mol of sulphonic acid chloride of the formula (VIII) is reacted per mol of starting compound of the formula (Ia) at 0 to 150° C., preferably at 20 to 70° C.

Possible diluents which are optionally added are all the inert polar organic solvents, such as halogenohydrocarbons, carboxylic acid esters, ethers, amides, nitrites, sulphones and sulphoxides.

Acetonitrile, ethyl acetate, dimethyl sulphoxide, tetrahydrofuran, dimethylformamide or methylene chloride are preferably employed.

If, in a preferred embodiment, the enolate salt of the compound of the formula (Ia) is prepared by addition of strong deprotonating agents (such as, for example, sodium hydride or potassium tert-butylate), further addition of acid-binding agents can be omitted.

If acid-binding agents are employed, the customary inorganic or organic bases are possible, examples which may be mentioned being sodium hydroxide, sodium carbonate, potassium carbonate, pyridine and triethylamine.

The reaction can be carried out under normal pressure or under increased pressure, and is preferably carried out under normal pressure. Working up is carried out by customary methods.

If appropriate, preparation process (E) can be carried out under phase transfer conditions (W. J. Spillane et. al.; J. Chem. Soc., Perkin Trans I, (3) 677–9 (1982)). In this case, 0.3 to 5 mol of sulphonic acid chloride of the formula (VIII), preferably 1 mol, are reacted per mol of starting compound of the formula Ia) at 0° to 150° C., preferably at 20 to 70° C.

Phase transfer catalysts which can be used are all the quaternary ammonium salts, preferably tetraoctylammonium bromide and benzyltriethylammonium chloride. Organic solvents which can be used in this case are all the non-polar inert solvents, and benzene and toluene are preferably employed.

In preparation process (F), I mol of the compound (la) and 1 to 2, preferably 1 to 1.3, mol of the phosphorus compound of the formula (IX) are reacted at temperatures between −40° C. and 150° C., preferably between −10 and 110° C., to give compounds of the formula (Ie).

Possible diluents which are optionally added are all the inert polar organic solvents, such as halogenohydrocarbons, ethers, amides, nitrites, sulphides, sulphones, sulphoxides etc.

Acetonitrile, ethyl acetate, dimethyl sulphoxide, tetrahydrofuran, dimethylformamide or methylene chloride are preferably employed.

Possible acid-binding agents which are optionally added are the customary inorganic or organic bases, such as hydroxides and carbonates. Examples which may be mentioned are sodium hydroxide, sodium carbonate, potassium carbonate, pyridine, triethylamine and DABCO.

The reaction can be carried out under normal pressure or under increased pressure, and is preferably carried out under normal pressure. Working up is carried out by customary methods of organic chemistry. Purification of the end products obtained is preferably carried out by crystallization, chromatographic purification or by so-called "incipient distillation", i.e. removal of the volatile constituents in vacuo.

In preparation process (Gα), about 1 mol of isocyanate or isothiocyanate of the formula (X) is reacted per mol of starting compound of the formula (Ia) at 0 to 100° C., preferably at 20 to 50° C.

Possible diluents which are optionally added are all the inert organic solvents, such as hydrocarbons, halogenated hydrocarbons, carboxylic acid esters, ethers, amides, nitriles, sulphones and sulphoxides. Toluene, methylene chloride, tetrahydrofuran, ethyl acetate, dimethylformamide or dimethyl sulphoxide are preferably employed.

If appropriate, catalysts can be added to accelerate the reaction. Catalysts which can very advantageously be employed are organotin compounds, such as, for example, dibutyltin dilaurate. The reaction is preferably carried out under normal pressure.

In preparation process (Gβ), about 1 mol of carbamic acid chloride or thiocarbamic acid chloride of the formula (XI) is reacted per mol of starting compound of the formula (Ia) at 0 to 150° C., preferably at 20 to 70° C.

Possible diluents which are optionally added are all the inert polar organic solvents, such as halogenohydrocarbons, carboxylic acid esters, ethers, amides, sulphones or sulphoxides.

Acetonitrile, ethyl acetate, dimethyl sulphoxide, tetrahydrofuran, dimethylformamide or methylene chloride are preferably employed.

If, in a -preferred embodiment, the enolate salt of the compound of the formula (Ia) is prepared by addition of strong deprotonating agents (such as, for example, sodium hydride or potassium tert-butylate), further addition of acid-binding agents can be omitted.

If acid-binding agents are employed, the customary inorganic or organic bases are possible, examples which may be mentioned being sodium hydroxide, sodium carbonate, potassium carbonate, pyridine, triethylamine and DABCO.

The reaction can be carried out under normal pressure or under increased pressure, and is preferably carried out under normal pressure. Working up is carried out by customary methods.

Process (H) is characterized in that compounds of the formula (Ia) are reacted with metal compounds of the formula (XII) or amines of the formula (XIII).

Diluents which can be employed in the process according to the invention are preferably ethers, such as tetrahydrofuran, dioxane or diethyl ether, or alcohols, such as methanol, ethanol or isopropanol, or else water. Process (H) according to the invention is in general carried out under normal pressure. The reaction temperatures are in general between −20° C. and 100° C., preferably between 0° C. and 50° C.

In carrying out process (H) according to the invention, the starting substances of the formula (Ia) and (XII) or (XIII) are in general used in approximately equimolar amounts. However, it is also possible to employ one or other of the components in a relatively large excess (up to 2 mol). In general, a procedure is followed in which the reaction mixture is concentrated by stripping off the diluent The following compounds of the formula (II) may be mentioned as examples:

methyl 5-(2,4-dichlorophenyl)-4-oxo-2,2-dimethyl-pentanecarboxylate
methyl 5-(2,4-dichlorophenyl)-4-oxo-2-methyl-2-ethyl-pentanecarboxylate
methyl 5-(2,4-dichlorophenyl)-4-oxo-2-methyl-2-isopropyl-pentanecarboxylate
methyl 5-(2,4-dichlorophenyl)-4-oxo-pentamethylene-pentanecarboxylate
methyl 5-(2,4-dichlorophenyl)-4-oxo-2,2-tetamethylene-pentanecarboxylate
methyl 5-(2,4-dichlorophenyl)-4-oxo-2,2-(2,3-benzotetramethylene)-pentanecarboxylate
methyl 5-(2,4-dichlorophenyl)-4-oxo-2,2-hexamethylene-pentanecarboxylate
methyl 5-(2,4-dichlorophenyl)-4-oxo-2,2-(2-methylpentamethylene)-pentanecarboxylate
methyl 5-(2,4-dichlorophenyl)-4-oxo-2,2-(3-methylpentamethylene)-pentanecarboxylate
methyl 5-(2,4-dichlorophenyl)-4-oxo-2,2-(3-ethylpentamethylene)-pentanecarboxylate
methyl 5-(2,4-dichlorophenyl)-4-oxo-2,2-(3-(1-methylethylpentamethylene)-pentanecarboxylate
methyl 5-(2,4-dichlorophenyl)-4-oxo-2,2-(3-methoxypentamethylene)-pentanecarboxylate
methyl 5-(2,4-dichlorophenyl)-4-oxo-2,2-(3-ethoxypentamethylene)-pentanecarboxylate
methyl 5-(2,4-dichlorophenyl)-4-oxo-2,2-(2,3-dimethylpentamethylene)-pentanecarboxylate
methyl 5-(2,4-dimethylphenyl)-4-oxo-2,2-dimethyl-pentanecarboxylate
methyl 5-(2,4-dimethylphenyl)-4-oxo-2-methyl-2-ethyl-pentanecarboxylate
methyl 5-(2,4-dimethylphenyl)-4-oxo-2-methyl-2-isopropyl-pentanecarboxylate
methyl 5-(2,4-dimethylphenyl)-4-oxo-2,2-pentamethylene-pentanecarboxylate
methyl 5-(2,4-dimethylphenyl)-4-oxo-2,2-tetramethylene-pentanecarboxylate
methyl 5-(2,4-dimethylphenyl)-4-oxo-2,2-(2,3-benzotetramethylene)-pentanecarboxylate
methyl 5-(2,4-dimethylphenyl)-4-oxo-2,2-hexamethylene-pentanecarboxylate
methyl 5-(2,4-dimethylphenyl)-4-oxo-2,2-(2-methylpentamethylene)-pentanecarboxylate
methyl 5-(2,4-dimethylphenyl)-4-oxo-2,2-(3-methylpentamethylene)-pentanecarboxylate
methyl 5-(2,4-dimethylphenyl)-4-oxo-2,2-(3-ethylpentamethylene)-pentanecarboxylate
methyl 5-(2,4-dimethylphenyl)-4-oxo-2,2-(3-(1-methylethyl)pentamethylene)-pentanecarboxylate
methyl 5-(2,4-dimethylphenyl)-4-oxo-2,2-(3-methoxypentamethylene)-pentanecarboxylate
methyl 5-(2,4-dimethylphenyl)-4-oxo-2,2-(3-ethoxypentamethylene)-pentanecarboxylate
methyl 5-(2,4-dimethylphenyl)-4-oxo-2,2-(2,3-dimethylpentamethylene)-pentanecarboxylate
methyl 5-(2,4,6-trimethylphenyl)-4-oxo-2,2-dimethyl-pentanecarboxylate
methyl 5-(2,4,6-trimethylphenyl)-4-oxo-2-methyl-2-ethyl-pentanecarboxylate
methyl 5-(2,4,6-trimethylphenyl)-4-oxo-2-methyl-2-isopropyl-pentanecarboxylate
methyl 5-(2,4,6-trimethylphenyl)-4-oxo-2,2-pentamethylene-pentanecarboxylate
methyl 5-(2,4,6-trimethylphenyl)-4-oxo-2,2-tetramethylene-pentanecarboxylate
methyl 5-(2,4,6-trimethylphenyl)-4-oxo-2,2-(2,3-benzotetramethylene)-pentanecarboxylate
methyl 5-(2,4,6-trimethylphenyl)-4-oxo-2,2-hexamethylene-pentanecarboxylate
methyl 5-(2,4,6-trimethylphenyl)-4-oxo-2,2-(2-methylpentamethylene)-pentanecarboxylate
methyl 5-(2,4,6-trimethylphenyl)-4-oxo-2,2-(3-methylpentamethylene)-pentanecarboxylate
methyl 5-(2,4,6-trimethylphenyl)-4-oxo-2,2-(3-ethylpentamethylene)-pentanecarboxylate
methyl 5-(2,4,6-trimethylphenyl)-4-oxo-2,2-(3-(I-methylethyl)penta-methylene)-pentanecarboxylate
methyl 5-(2,4,6-trimethylphenyl)-4-oxo-2,2-(3-methoxypentamethylene)-pentanecarboxylate
methyl 5-(2,4,6,-trimethylphenyl)-4-oxo-2,2-(3-ethoxypentamethylene)-pentanecarboxylate
methyl 5-(2,4,6-trimethylphenyl)-4-oxo-2,2-(2,3-dimethylpentamethylene)-pentanecarboxylate The active compounds according to the invention are suitable for controlling animal pests, preferably arthropods and nematodes, in particular insects and arachnids, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadiffidium vulgare* and *Porcellio scaber.*

From the order of the Diplopoda, for example, *Blaniulus guttulatus.*

From the order of the Chilopoda, for example, *Geophilus carpophagus* and *Scutigera spec.*

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus, Gryllotalpa spp., Locusta migratoria migratorioides, Melanoplus differentialis, Schistocerca gregaria* and *Supella spp..*

From the order of the Dermaptera, for example, *Forficula auricularia.*

From the order of the Isoptera, for example, Reticulitermes spp.

From the order of the Anoplura, for example, *Phylloxera vastatrix,* Pemphigus spp., Phthirus spp., Pediculus spp., Haematopinus spp., Linognathus spp., Solenopotes spp..

From the order of the Mallophaga, for example, *Trichodectes spp., Damalinea spp., Trimenopon spp., Monopon spp., Tinoton spp., Bovicola spp., Werneckiella spp., Lepikentron spp., Felicola spp.*

From the order of the Thysanoptera, for example, *Hercinothrips femoralis* and *Thrips tabaci.*

From the order of the Heteroptera, for example, *Eurygaster spp., Dysdercus intermedius, Piesma quadrata, Cimex lectularius, Rhodnius prolixus, Triatoma spp., Panstrongylus spp.*

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens, Aonidiella auranfti, Aspidiotus hederae, Pseudococcus spp.* and *Psylla spp..*

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp. Bucculatrix thurberiella, Phyllocnistis citrella, Agrotis spp., Euxoa spp., Feltia spp., Earias insulana, Heliothis spp., Spodoptera exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehnieha, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae, Diabrotica spp., Psylliodes chrysocephala, Epilachna varive stis, Atomaria spp., Oryzaephilus surinamensis, Antho nomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Cono derus spp., Melolontha melolontha, Amphimallon solsti tialis* and *Costelytra zealandica.*

From the order of the Hymenoptera, for example, *Diprion spp., Hoplocampa spp., Lasius spp., Monomorium pharaonis* and *Vespa spp.*

From the order of the Diptera, for example, *Aedes spp., Anopheles spp., Culex spp., Drosophila melanogaster, Musca spp., Fannia spp., Calliphora, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae* and *Tipula paludosa, Simulium spp., Eusimulium spp. Phlebotomus spp., Lutzomyia spp. Culicoides spp., Chrysops spp., Hybomitra spp., Atylotus spp., Tabanus spp., Haematopota spp., Philipomyia spp., Bravla spp., Hydrotaea spp., Stomoxys spp., Haematobia spp., Morellia spp., Fannia spp., Glossina spp., Calliphora spp., Wohlfahrlia spp., Sarcophaga spp., Oestrus spp., Hypoderma spp., Gasterophilus spp., Hippobosca spp., Lipoptena spp., Melophagus spp.* and *Muscina spp.*

From the order of the Siphonapterida, for example, *Xenopsylla spp., Ceratophyllus spp., Pulex spp.* and *Ctenocephalides spp.,*

From the order of the Arachnida, for example, *Scorpio maurus* and *Latrodectus mactans.*

From the order of the Acarina, for example, *Myocoptes spp., Otodectes spp., Acarus siro, Argas spp., Ornithodoros spp., Ornithodoros spp., Derrmanyssus spp., Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp., Tetranychus spp., Dermacentor spp., Haemaphysalis spp., Raillietia spp., Pneumonyssus spp., Sternostorma spp.* and *Varroa spp..*

From the order of the Actinedida (Prostigmata) and Acaridida (Astigmata), for example: *Acarapis spp., Cheyletiella spp., Omithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp., Laminosioptes spp..*

The active compounds according to the invention are distinguished by a potent insecticidal and acaricidal activity.

They can be employed particularly successfully for the control of insects which are harmful to plants, such as, for example, against the larvae of the mustard beetle (*Phaedon cochleariae*) or against the larvae of the green rice leafhopper (*Nephotettix cincticeps*) or against the caterpillars of the cabbage moth (Plutella maculipennis).

The active compounds according to the invention can furthermore be used as defoliants, desiccants, haulm killers and, especially, as weedkilers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotola, Lindernia, Lamium, Veronica, Abutilon, Emex, Datura, Viola, Galeopsis, Papaver Centaurea, Trifolium, Ranunculus and Taraxacum.

Dicotyledon crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cycnodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon crops of the genera: Oryza, Zea, Triticum, Hordeum, Avena, Secale, Sorghum, Panicum, Sachharum, Ananas, Asparagus and Allium.

However, the use of the active compounds according to the invention is in no way restricted to these genera, but also extends in the same manner to other plants.

Depending on the concentration, the compounds are suitable for total weed control, for example on industrial terrain and rail tracks, and on paths and areas with or without tree stands. Equally, the compounds can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pastures, and for selective weed control in annual crops.

The novel active compounds are highly suitable for selective control of monocohyledon weeds in dicotyledon crops, both pre- and post-emergence. For example, they can be used very successfully in cotton or sugar-beet to combat grass weeds.

The active compounds can be converted into the customary formulations, such as solutions, emulsions, wettable powders, suspensions, powders, dusts, pastes, soluble powders, granules, suspoemulsion concentrates, natural and synthetic materials impregnated with active compound, and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If water is used as an extender, organic solvents can, for example, also be used as auxiliary solvents. Liquid solvents which are mainly suitable are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol as well as their ethers and esters, ketones such as acetone, methyl ethyl ketone, methyl isobutyl ketone or cyclohexanone, strongly polar solvents such as dimethylformamide and dimethyl sulphoxide, and water.

Suitable solid carriers are: for example ammonium salts and ground natural minerals such as kaolins, clays, talc, chalk, quartz, attapulgite, montmorillonite or diatomaceous earth, and ground synthetic minerals such as highly disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam-formers are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignin-sulphite waste liquors and methylcellulose.

Adhesives such as carboxymethylcellulose and natural and synthetic polymers in the form of powders, granules or latexes such as gum arabic, polyvinyl alcohol and polyvinyl acetate, or else natural phospholipids such as cephalins and lecithins, and synthetic phospholipids can be used in the formulations. Further additives can be mineral and vegetable oils.

It is possible to use colourants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, bactericides, acaricides, nematocides, fungicides, growth regulating substances or herbicides. The insecticides include, for example, phosphates, carbamates, carboxylates, chlorinated hydrocarbons, phenylureas, substances produced by microorganisms and the like.

Fungicides:

2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)-benzanide; (E)-2-methoxyimino-N-methyl-2-(2-phenoxyphenyl)-acetamide; 8-hydroxyquinoline sulphate; methyl-(E)-2-{2-[6-(2-cyanophenoxy)-pyrimidine-4-yloxy]-phenyl}-3-methoxyacrylate; methyl-(E)-methoximino-[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, chinomethionate, (quinomethionate), chloroneb, chloropicrin, chlorothalonil, chlozolinate, cufraneb, cymoxanil, cyproconazole, cyprofuram, dichlorophen, diclobutrazole, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbaim, fedimzone, fluazinanm, fludioxonil, fluoromide, fluquinconazole, flusilazole, flusulfamide, flutolanil, flutriafol, folpet, fosetyl aluminium, fthalide, fuberidazole, furalaxyl, furmecyclox, guazatine, hexachlorobenzene, hexaconazole, hymexazole, imazalil, imibenconazole, iminoctadin, iprobenfos (IBP), iprodione, isoprothiolane, kasugamycin, copper formulations, such as: copper hydroxide, copper naphthenate, copper oxychloride, copper sulfate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphene, phthalide, pimaricin, piperalin, polycarbamate, polyoxin, probenazole, prochloraz, procymidon, propamocarb, propiconazole, propineb, pyrazophos, pyrifenox, pyrimethanil, pyroquilon, quintozene (PCNB), sulphur and sulphur formulations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxid, trichlamid, tricyclazol, tridemorph, triflumizol, triforin, triticonazole, validamycin A, vinclozolin, zineb, ziram.

Bactericides:

bronopol, dichlorophen, nitrapyrin, nickel dimethyldithiocarbamate, kasugamycin, octhilinon, furancarboxylic acid, oxytetracycline, probenazole, streptomycin, tecloftalam, copper sulphate and other copper formulations.

Insecticides/acaricides/nematicides:

abamectin, abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, betacylutliin, bifenthrin, BPMC, brofenprox, bromophos A, bufencarb, buprofezn, butocarboxin, butylpyridaben, cadusafos, carbaryl, carbofuran, carbophenothion, carbosulfan, cartap, CGA 157 419, CGA 184699, chloethocarb, chlorethoxyfos, chlorfenvinphos, chlorfluazuron, chlormephos, chlorpyrifos, chlorpyrifos M, cis-resmethrin, cocytlrin, clofentezin, cyanophos, cycloprothrin, cyfluthrin, cyhalothrin, cyhexatin, cypermethrin, cyromazin, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivemectin, lamda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamdon, phoxim, pirimicarb, pirimiphos M, primiphos A, profenofos, promecarb, propaphos, propoxur, prothiofos, prothoate, pymetrozin, pyrachlophos, pyradaphenthion, pyresmethrin, pyrethrum, pyridaben, pyrimidifen, pyriproxrfen, quinalphos, RH 5992, salithion, sebufos, silafluofen, sulfotep, suiprofos, tebufenozide, tebufenpyrad, tebupirimphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetamethrin.

Herbicides:

for example anilides such as, for example, diflufenican and propanil; arylcarboxylic acids such as, for example, dichloropicolinic acid, dicamba and picloram; aryloxyalkanoic acids such as, for example, 2,4 D, 2,4 DB, 2,4 DP, fluroxypyr, MCPA, MCPP and triclopyr; aryloxy-phenoxyalkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates such as, for example, butylate, cycloate, diallate, EPTC, esprocarb, molinate, prosulfocarb, thiobencarb and triallate; triazines such as, for example, atrazjne, cyanazine, simazine, simetryne, terbutryne and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

The active compound according to the invention can furthermore be present in commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound is distinguished by an outstanding residual action on wood and clay and by a good stability to alkali on lined substrates.

The active compounds according to the invention act not only against plant pests, hygiene pests and pests of stored products, but also in the veterinary medicine sector against animal parasites (ectoparasites), such as hard ticks, soft ticks, mange mites, harvest mites, flies (biting and licking), parasitic fly larvae, lice, hair lice, feather lice and fleas. For example, they display an outstanding activity against ticks, such as, for example, Boophilus microplus.

The active compounds of the formula (I) according to the invention are also suitable for combating arthropods which infest agricultural productive livestock such as, for example, cattle, sheep, goats, horses, pigs, donkeys, camels, buffalo, rabbits, chickens, turkeys, ducks, geese, bees and other pets, such as, for example, dogs, cats, cage birds and aquarium fish, and also so-called test animals, such as, for example, hamsters, guinea pigs, rats and mice. By combating these anthropods cases of death and reductions in productivity (for meat, milk, wool, hides, eggs, honey, etc.) should be diminished, so that more economic and more simple animal husbandry is possible by use of the active compounds according to the invention.

The active compounds according to the invention are used in the veterinary sector in a known manner by enteral administration in the form of, for example, tablets, capsules, potions, drenches, granules, pastes, boli, the feed-through process and suppositories, by parenteral administration, such as, for example, by injection (intramuscular, subcutaneous, intravenous, intraperitoneal etc), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices, etc.

When used for livestock, poultry, pets etc. the active compounds of the formula (I) can be used as formulations (for example powders, emulsions, free-flowing compositions), which comprise the active compounds in an amount of 1 to 80% by weight, directly or after a 100 to 10,000 fold dilution, or they can be used as a chemical bath.

The preparation and the use of the active compounds according to the invention is illustrated in the following examples.

PREPARATION EXAMPLES
Example Ia-1

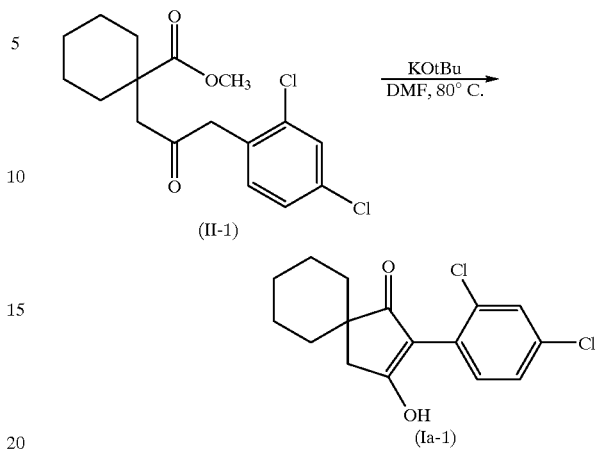

1.85 g of potassium tert-butylate are added to a solution of the compound according to Example II-1 (5.19 g, 15.13 mmol) in dimethylformamide (25 ml) and the mixture is stirred at 80° C. for 2 hours. 5 ml of acetic acid are added, the mixture is concentrated and the residue is chromatographed over silica gel (2:1 ethyl acetate:hexane). 3.07 g (65%) of the compound shown above are isolated. White solid, melting point: 219° C.

The compounds of the formula (Ia) listed in Table 14, which are shown in the form of one of the possible isomers, were prepared analogously or in accordance with the general instructions of the preparation.

TABLE 14

(Ia)

| Ex. No. | A | B | X | Y | $Z_n$ | m.p. ° C. |
|---|---|---|---|---|---|---|
| Ia-2 | | —(CH$_2$)$_5$— | CH$_3$ | CH$_3$ | H | 206 |
| Ia-3 | | —(CH$_2$)$_5$— | CH$_3$ | CH$_3$ | 6-CH$_3$ | 255 |
| Ia-4 | | (benzyl-CH$_2$—, CH$_2$—) | CH$_3$ | CH$_3$ | H | 216 |
| Ia-5 | | (benzyl-CH$_2$—, CH$_2$—) | CH$_3$ | CH$_3$ | 6-CH$_3$ | 232 |
| Ia-6 | | —(CH$_2$)$_5$— | OCH$_3$ | CH$_3$ | 6-CH$_3$ | 193 |
| Ia-7 | | —(CH$_2$)$_2$—CHCH$_3$—(CH$_2$)$_2$— | CH$_3$ | CH$_3$ | 6-CH$_3$ | 248 |
| Ia-8 | CH$_3$ | CH$_3$ | CH$_3$ | CH$_3$ | 6-CH$_3$ | 248 |

Example Ib-1

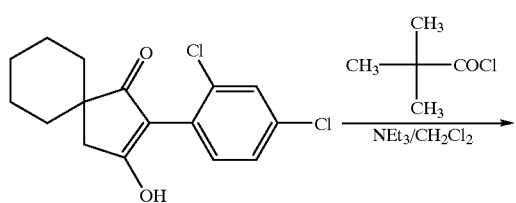

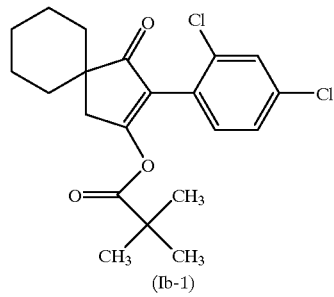

(Ib-1)

Pivaloyl chloride (0.7 ml) is added to a solution of the compound according to Example Ia-1 (936 mg, 3 mmol) in methylene chloride (10 ml) and triethylamine (1 ml). After one hour at room temperature, the reaction mixture is filtered directly over silica gel (mobile phase 1:4, ethyl ether: petroleum ether). 1.1 g (97%) of the compound shown above are obtained. White solid, melting point 93° C.

The compounds of the formula (Ib) listed in Table 15, which are shown in the form of one of the possible isomers, were prepared analogously and in accordance with the general instructions relating to preparation.

TABLE 15

(Ib)

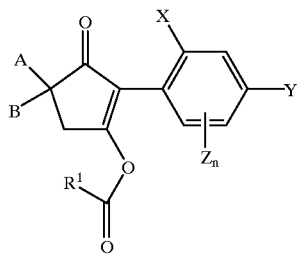

| Ex. No. | A | B | X | Y | $Z_n$ | $R^1$ | m.p. ° C. |
|---|---|---|---|---|---|---|---|
| Ib-2 | | —(CH$_2$)$_5$— | CH$_3$ | CH$_3$ | H | CH$_3$— | oil |
| Ib-3 | | —(CH$_2$)$_5$— | CH$_3$ | CH$_3$ | H | (CH$_3$)$_3$C— | oil |
| Ib-4 | | —(CH$_2$)$_5$— | CH$_3$ | CH$_3$ | H | Cl—CH$_2$— | oil |
| Ib-5 | | —(CH$_2$)$_5$— | CH$_3$ | CH$_3$ | H | n-H$_9$C$_4$—CH(C$_2$H$_5$)— | oil |
| Ib-6 | | —(CH$_2$)$_5$— | CH$_3$ | CH$_3$ | 6-CH$_3$ | CH$_3$— | 58 |
| Ib-7 | | —(CH$_2$)$_5$— | CH$_3$ | CH$_3$ | 6-CH$_3$ | (CH$_3$)$_3$C— | 94 |
| Ib-8 | | —(CH$_2$)$_5$— | CH$_3$ | CH$_3$ | 6-CH$_3$ | Cl—CH$_2$— | oil |
| Ib-9 | | —(CH$_2$)$_5$— | CH$_3$ | CH$_3$ | 6-CH$_3$ | n-H$_9$C$_4$—CH(C$_2$H$_5$)— | oil |
| Ib-10 | | —(CH$_2$)$_5$— | CH$_3$ | CH$_3$ | H | C$_6$H$_5$— | oil |
| Ib-11 | | —(CH$_2$)$_5$— | Cl | Cl | H | CH$_3$— | 68 |
| Ib-12 | | o-C$_6$H$_4$(CH$_2$—)$_2$ | CH$_3$ | CH$_3$ | 6-CH$_3$ | CH$_3$— | 118 |

TABLE 15-continued (Ib)

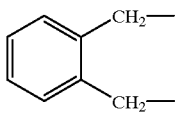

| Ex. No. | A | B | X | Y | $Z_n$ | $R^1$ | m.p. ° C. |
|---|---|---|---|---|---|---|---|
| Ib-13 | \multicolumn{2}{c|}{o-xylylene} | $CH_3$ | $CH_3$ | 6-$CH_3$ | $(CH_3)_3C-$ | 124 |
| Ib-14 | \multicolumn{2}{c|}{o-xylylene} | $CH_3$ | $CH_3$ | 6-$CH_3$ | n-$H_9C_4$—CH($C_2H_5$)— | 105 |
| Ib-15 | \multicolumn{2}{c|}{o-xylylene} | $CH_3$ | $CH_3$ | H | $CH_3-$ | 91 |
| Ib-16 | \multicolumn{2}{c|}{o-xylylene} | $CH_3$ | $CH_3$ | H | $(CH_3)_3C-$ | 78 |
| Ib-17 | \multicolumn{2}{c|}{o-xylylene} | $CH_3$ | $CH_3$ | H | n-$H_9C_4$—CH($C_2H_5$)— | oil |
| Ib-18 | \multicolumn{2}{c|}{—$(CH_2)_5$—} | $OCH_3$ | $CH_3$ | 6-$CH_3$ | $(CH_3)_3C-$ | 103 |
| Ib-19 | \multicolumn{2}{c|}{—$(CH_2)_5$—} | $OCH_3$ | $CH_3$ | 6-$CH_3$ | $CH_3-$ | 105 |
| Ib-20 | \multicolumn{2}{c|}{—$(CH_2)_2$—CHCH$_3$—$(CH_2)_2$—} | $CH_3$ | $CH_3$ | 6-$CH_3$ | $(CH_3)_3C-$ | 112 |
| Ib-21 | \multicolumn{2}{c|}{—$(CH_2)_2$—CHCH$_3$—$(CH_2)_2$—} | $CH_3$ | $CH_3$ | 6-$CH_3$ | $CH_3-$ | 115 |
| Ib-22 | $CH_3$ | $CH_3$ | $CH_3$ | $CH_3$ | 6-$CH_3$ | $(CH_3)_3C-$ | 65 |
| Ib-23 | $CH_3$ | $CH_3$ | $CH_3$ | $CH_3$ | 6-$CH_3$ | $CH_3-$ | oil |

Example Ic-1:

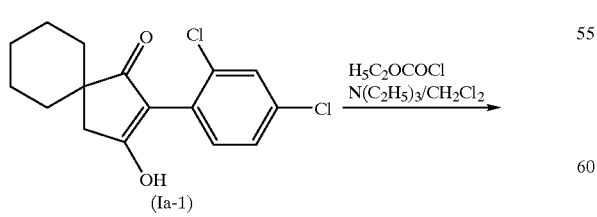

-continued

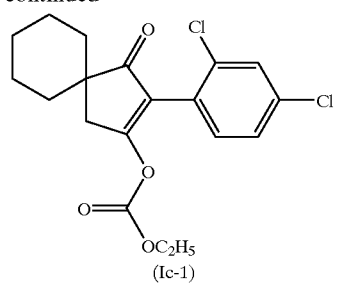

0.8 ml of ethyl chloroformate is added to a solution of the compound according to Example Ia-1 (1.43 g, 4.58 mmol) in $CH_2Cl_2$ (10 ml) and triethylamine (2 ml) at room temperature. After 2.5 hours, the reaction mixture is filtered directly over silica gel (mobile phase 4:1, $CH_2Cl_2$: petroleum ether). 1.37 g (77%) of the compound shown above are obtained as an oil.

$^1$HNMR($CDCl_3$, 200 MHz, δ ppm): 3.00 (bs, 1H); 4.28 (q, 2H, J=7 Hz).

The compounds of the formula (1c) listed in Table 16, which are shown in the form of one of the possible isomers, were prepared analogously and in accordance with the general instructions relating to preparation.

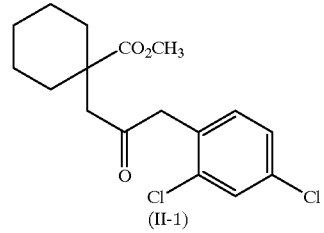
(II-1)

A mixture of the compound according to Example XIV-1 (1.95 g; 5.93 mmol), potassium carbonate (0.82 g), acetone

TABLE 16

(Ic)

| Ex. No. | A | B | X | Y | $Z_n$ | M | $R^2$ | m.p. °C. |
|---|---|---|---|---|---|---|---|---|
| Ic-2 | | —$(CH_2)_5$— | $CH_3$ | $CH_3$ | H | O | $CH_3$— | 92 |
| Ic-3 | | —$(CH_2)_5$— | $CH_3$ | $CH_3$ | H | O | $(CH_3)_2CH$— | 76 |
| Ic-4 | | —$(CH_2)_5$— | $CH_3$ | $CH_3$ | 6-$CH_3$ | O | $CH_3$— | 100 |
| Ic-5 | | —$(CH_2)_5$— | $CH_3$ | $CH_3$ | 6-$CH_3$ | O | $(CH_3)_2CH$— | 108 |
| Ic-6 | | o-xylylene | $CH_3$ | $CH_3$ | 6-$CH_3$ | O | $(CH_3)_2CH$— | 161 |
| Ic-7 | | o-xylylene | $CH_3$ | $CH_3$ | H | O | $(CH_3)_2CH$— | 63–70 |
| Ic-8 | | —$(CH_2)_5$— | $OCH_3$ | $CH_3$ | 6-$CH_3$ | O | $(CH_3)_2CH$— | 112 |
| Ic-9 | | —$(CH_2)_2$—$CHCH_3$—$(CH_2)_2$— | $CH_3$ | $CH_3$ | 6-$CH_3$ | O | $(CH_3)_2CH$— | 78 |
| Ic-10 | $CH_3$ | $CH_3$ | $CH_3$ | $CH_3$ | 6-$CH_3$ | O | $(CH_3)_2CH$— | 93 |

Preparation of the starting compounds

Example I1-1

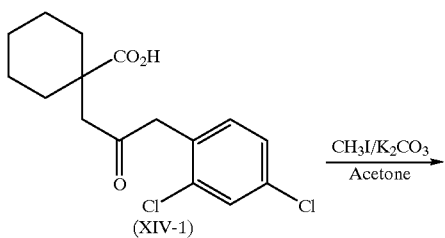
(XIV-1)

(30 ml) and iodomethane (2 ml) is boiled under reflux for 5 hours and concentrated and the residue is chromatographed directly over silica gel (mobile phase: 15% of ethyl acetate, 85% of petroleum ether). 1.89 g of the compound shown above are obtained as an oil (93%).

$^1$HNMR ($CDCl_3$, 200 MHz, δ ppm): 2.86 (s, 2H); 3.65 (s, 3H); 3.78 (s, 2H).

The examples of the formula (II) listed in Table 17 were prepared analogously.

TABLE 17

(II)

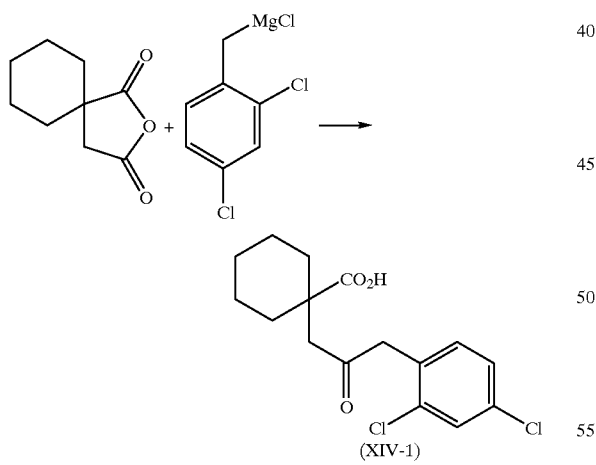

| Ex.—No. | A | B | X | Y | $Z_n$ | $R^8$ | $^1$HNMR (200 MHz, CDCl$_3$, δppm) |
|---|---|---|---|---|---|---|---|
| II-2 | | —(CH$_2$)$_5$— | CH$_3$ | CH$_3$ | H | CH$_3$ | 2.31(s, 3H); 2.79(m, 2H) |
| II-3 | | —(CH$_2$)$_5$— | CH$_3$ | CH$_3$ | 6-CH$_3$ | CH$_3$ | 2.75(s, 2H); 3.67(s, 2H) |
| II-4 | | (o-xylylene) | CH$_3$ | CH$_3$ | H | CH$_3$ | 2.18(s, 3H); 2.30(s, 3H) |
| II-5 | | (o-xylylene) | CH$_3$ | CH$_3$ | 6-CH$_3$ | CH$_3$ | 2.92(s, 2H); 6.85(s, 2H) |
| II-6 | | —(CH$_2$)$_5$— | OCH$_3$ | CH$_3$ | 6-CH$_3$ | CH$_3$ | 2.16(s, 3H); 2.30(s, 3H); 2.76(s, 2H) |
| II-7 | | —(CH$_2$)$_2$—CHCH$_3$—(CH$_2$)$_2$— | CH$_3$ | CH$_3$ | 6-CH$_3$ | CH$_3$ | 0.86(d, 3H, J=7 Hz); 2.86 (s, 2H) |
| II-8 | CH$_3$ | CH$_3$ | CH$_3$ | CH$_3$ | 6-CH$_3$ | CH$_3$ | 1.39(s, 6H); 2.68(s, 2H) |

Example XIV-1

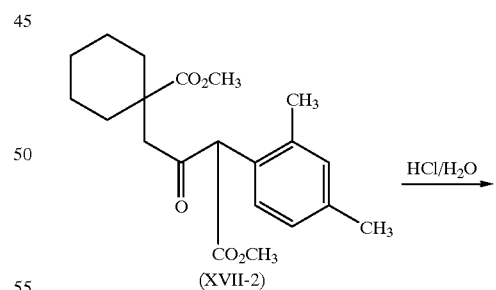

(XIV-1)

A solution of 2,4-dichlorobenzylmagnesium chloride (prepared from 12.6 g of 2,4-dichlorobenzyl chloride and 3 g of magnesium in 100 ml of ethyl ether) is added to a solution of 10 g of 2,2-pentamethylenesuccinic anhydride (cf.: M. Qudrat-Khuda et al., J. Indian Chem. Soc., (1947), 24, 15) in ethyl ether (100 ml) at room temperature. After 30 minutes at room temperature, 100 ml of water and 20 g of ammonium chloride are added. The product is extracted with ethyl ether. Chromatography over silica gel (mobile phase 30% of ethyl acetate: 70% of petroleum ether) gives 3.95 g (22%) of the compound shown above as a white solid of melting point 115° C.

Example XIV-2

(XVII-2)

HCl/H$_2$O

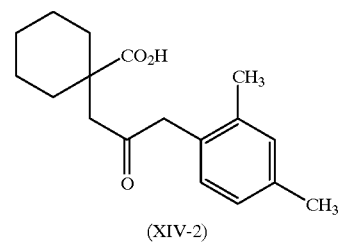

(XIV-2)

A suspension of the compound according to Example (XVII-2) (18.2 g mol) in 20% strength aqueous HCl (300 ml) is heated under reflux for 50 hours, cooled and extracted with ethyl ether. After concentration, the residue is washed with petroleum ether. 9.5 g (65%) of the compound shown above are obtained as an oil.

The following compounds were prepared analogously to the process described under Example XIV-1 and XIV-2:

14.4 g of methyl 2,4,6-trimethylphenylacetate are added to a solution of lithium diisopropylamide (80 mmol) in tetrahydrofuran (100 ml) at −40° C. After 30 minutes at room temperature, 10 g of 2,2-pentamethylene-succinic acid methyl ester chloride are added and the mixture is stirred at room temperature (1 hour). 100 ml of water and 30 g of ammonium chloride are then added. The product is extracted with ethyl ether. After concentration, the residue is chro-

TABLE 18

(XIV)

| Ex. No. | A | B | X | Y | $Z_n$ | $^1$HNMR (200 MHz, CDCl$_3$, δppm) |
|---|---|---|---|---|---|---|
| XIV-3 | | —(CH$_2$)$_5$— | CH$_3$ | CH$_3$ | 6-CH$_3$ | 2.78(s, 2H); 3.69(s, 2H) |
| XIV-4 | | —(CH$_2$)$_5$— | OCH$_3$ | CH$_3$ | 6-CH$_3$ | 2.30(s, 3H); 2.78(s, 2H) |
| XIV-5 | | —(CH$_2$)$_2$—CHCH$_3$—(CH$_2$)$_2$— | CH$_3$ | CH$_3$ | 6-CH$_3$ | oil |
| XIV-6 | CH$_3$ | CH$_3$ | CH$_3$ | CH$_3$ | 6-CH$_3$ | oil |
| XIV-7 | | (o-C$_6$H$_4$)(CH$_2$—)$_2$ | CH$_3$ | CH$_3$ | H | oil |
| XIV-8 | | (o-C$_6$H$_4$)(CH$_2$—)$_2$ | CH$_3$ | CH$_3$ | 6-CH$_3$ | oil |

Example XVII-1

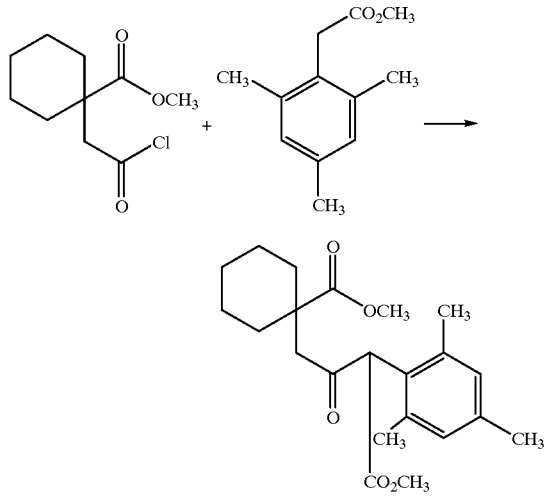

(XVII-1)

matographed over silica gel (mobile phase: $CH_2Cl_2$). 6.2 g (32%) of a solid of melting point 89° C. are obtained.

The compounds listed in Table 19 were prepared analogously:

TABLE 19

(XVII)

$$R^8O_2C-\underset{A}{\overset{}{C}}-\underset{B}{\overset{}{CH_2}}-\underset{\overset{\parallel}{O}}{C}-CH(CO_2R^{8'})-\text{Ar}(X)(Y)(Z_n)$$

| Ex. No. | A | B | $R^{8'}$ | $R^8$ | X | Y | $Z_n$ | $^1$HNMR (200 MHz, $CDCl_3$, δ[ppm]) |
|---|---|---|---|---|---|---|---|---|
| XVII-2 | | $-(CH_2)_5-$ | $CH_3$ | $CH_3$ | $CH_3$ | $CH_3$ | H | 2.30(bs, 6H); 6.9–7.1(m, 3H). |
| XVII-3 | | $-(CH_2)_5-$ | $CH_3$ | $CH_3$ | Cl | Cl | H | 2.88 (m, 2H); 13.12(s, 1H). |
| XVII-4 | | o-xylylene ($-CH_2-C_6H_4-CH_2-$) | $CH_3$ | $CH_3$ | $CH_3$ | $CH_3$ | 6-$CH_3$ | 3.66 (s, 3H); 3.72(s, 3H). |
| XVII-5 | | $-(CH_2)_5-$ | $CH_3$ | $CH_3$ | $OCH_3$ | $CH_3$ | 6-$CH_3$ | 6.55 (s, 1H); 6.65 (s, 1H). |
| XVII-6 | $-(CH_2)_2-CHCH_3-(CH_2)_2-$ | | $CH_3$ | $CH_3$ | $CH_3$ | $CH_3$ | 6-$CH_3$ | oil |
| XVII-7 | $CH_3$ | $CH_3$ | $CH_3$ | $CH_3$ | $CH_3$ | $CH_3$ | 6-$CH_3$ | oil |
| XVII-8 | | o-xylylene ($-CH_2-C_6H_4-CH_2-$) | $CH_3$ | $CH_3$ | $CH_3$ | $CH_3$ | H | oil |

The compounds of the formulae (XVII) and (XIV) obtained as oils were not characterized further, but were employed as crude products in the reactions for the preparation of compounds of the formula (II).

Use Examples

Example A

Tetranychus Test (resistant)

Solvent: 3 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration Bean plants (Phaseolus vulgaris) which are heavily infested with all development stages of the common spider mite or bean spider mite (*Tetranychus urticae*) are treated by being dipped into the preparation of active compound of the desired concentration.

After the desired time, the destruction in % is determined. 100% means that all the spider mites have been killed; 0% means that none of the spider mites have been killed.

In this test, for example, the compounds according to Preparation Examples Ia-l, Ia-2 and Ia-3 caused a destruction of at least 80% after 13 days at an active compound concentration of, for example, 0.01%.

Example B

Phaedon larvae test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with mustard beetle larvae (*Phaedon cochleariae*), as long as the leaves are still moist.

After the desired time, the destruction in % is determined. 100% means that all the beetle larvae have been killed; 0% means that none of the beetle larvae have been killed.

In this test, for example, the compounds according to Preparation Examples Ia-1, Ia-2, Ia-3, Ib-1, Ib-2, Ib-3, Ib4, lb-5, Db-7, Ib-8, Ib-9, Ic-1, Ic-2, Ic-3, Ic-4 and Ic-5 caused a destruction of 100% after 7 days at an active compound concentration of, for example, 0.1%.

Example C

Plutella test

Solvent: 7 parts by weight of dimethylformamide

Emulsifier: 1 part by weight of alkylaryl polyglycol ether

To produce a suitable preparation of active compond, 1 part by weight of active compound is mixed with the stated amount of solvent and the stated amount of emulsifier, and the concentrate is diluted with water to the desired concentration Cabbage, leaves (*Brassica oleracea*) are treated by being dipped into the preparation of active compound of the desired concentration and are infested with caterpillars of the diamond-back moth (*Plutella maculipennis*) while the leaves are still moist.

After the desired time, the destruction in % is determined. 100% means that all the caterpillars have been killed; 0% means that none of the caterpillars have been killed.

In this test, for example, the compounds according to Preparation Examples Ia-1, Ia-2, Ia-3, Ib-1, Ib-2, Ib-3, Ib-4, Ib-5, Ib-7, lb-8, Tb-9, Ic-1, Ic-2, Ic3, Ic4 and Ic-5 caused a destruction of 100% after 7 days at an active compound concentration of, for example, 0.1%.

Example D

Spodoptera test

Solvent: 7 parts by weight of dimethylformamide

Emulsifier: I part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the owlet moth (*Spodoptera frugiperda*), as long as the leaves are still moist.

After the desired time, the destruction in % is determined. 100% means that all the caterpillars have been killed; 0% means that none of the caterpillars have been killed.

In this test, for example, the compounds according to Preparation Examples Ia-2, Ib-2, Ib-3 and Ic-2 caused a destruction of at least 85% after 7 days at an active compound concentration of, for example, 0.1%.

Example E

Nephotettix Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Rice seedlings (*Oryzae sativa*) are treated by being dipped into the preparation of active compound of the desired concentration and are infested with larvae of the green rice leafhopper (*Nephotettix cincticeps*), as long as the seedlings are still moist.

After the desired time, the destruction in % is determined. 100% means that all the leafhoppers have been killed; 0% means that none of the leafhoppers have been killed.

In this test, for example, the compounds according to Preparation Examples Ia-2, Tb-2, Ib-3 and Ic-2 caused a destruction of 100% after 6 days at an active compound concentration of, for example, 0.1%.

Example F

Myzus Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) which are heavily infested by the peach aphid (*Myzus persicae*) are treated by being dipped into the preparation of active compound of the desired concentration.

After the desired time, the destruction in % is determined. 100% means that all the leaf aphids have been killed; 0% means that none of the leaf aphids have been killed.

In this test, for example, the compound according to Preparation Example Ib-7 caused a destruction of 98% after 6 days at an active compound concentration of, for example, 0.1%.

Example G

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added, and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)

100%=total destruction

In this test, for example, the compound according to Preparation Example Ia-1 showed, when applied in an amount of, for example, 250 g/ha, good tolerance by, for example, Beta vulgaris and a degree of damage of at least 95% with the following test plants: *Digitaria sanguinalis, Echinocloa colonom, Panicum miliaceum* and *Setaria viridis*.

Example H

Test with Boophilus microplus resistant/SP-resistant Parkhurst strain

Test animals: Adult satiated females

Solvent: Dimethyl sulphoxide 20 mg of active compound are dissolved in 1 ml of dimethyl sulphoxide, and lower concentrations are prepared by dilution with the same solvent.

The test is carried out as a 5-fold determination. 1 µl of the solutions is injected into the abdomen and the animals are transferred to dishes and kept in a controlled-environment chamber. The action is determined by the inhibition of the egg plant. An action of 100% means that no tick has laid fertile eggs.

In this test, for example, the compounds according to Preparation Examples Ia-1, Ib-6, Ic-4 and Ic-5 in each case showed an action of 100% at an active compound concentration of, for example, 20 µg/animal.

We claim:
1. Compounds of the formula (I)

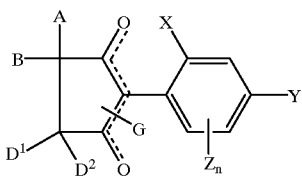 (I)

in which

X represents halogen, nitro, cyano, alkyl, alkoxy, alkenyloxy, alkylthio, alkylsulphinyl, alkylsulphonyl, halogenoalkyl or halogenoalkoxy, Y represents hydrogen, halogen, nitro, cyano, alkyl, alkoxy, alkenyloxy, alkylthio, alkylsulphinyl, alkylsulphonyl, halogenoalkyl or halogenoalkoxy, Z represents halogen, nitro, cyano, alkyl, alkoxy or halogenoalkoxy, n represents an integer from 0 to 3, or wherein the radicals X and Z, together with the phenyl radical to which they are bonded, form the naphthalene radical of the formula

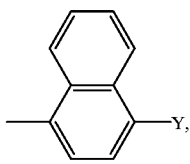

in which

Y has the abovementioned meaning,

A and B independently of one another represent alkyl, alkenyl, alkinyl, alkoxyalkyl, polyalkoxyalkyl or alkylthioalkyl, in each case optionally substituted once or several times in an identical or different manner by halogen, or saturated or unsaturated, unsubstituted or substituted cycloalkyl which is optionally interrupted by at least one heteroatom, or phenyl or phenylalkyl, in each case optionally substituted once or several times in an identical or different manner by halogen, alkyl, halogenoalkyl, alkoxy, halogenoalkoxy, cyano or nitro, or A and B, together with the carbon atom to which they are bonded, form a saturated or unsaturated ring which is optionally interrupted by at least one heteroatom and is optionally substituted, or A and B, together with the carbon atom to which they are bonded, form a ring in which two substituents, together with the carbon atoms to which they are bonded, form a saturated or unsaturated ring which is optionally substituted once or several times in an identical or different manner by halogen, alkyl or alkoxy and jay comprise oxygen or sulphur, $D^1$ and $D^2$ independently of one another represent hydrogen, halogen or alkyl which is optionally substituted by halogen or optionally substituted phenyl, G represents hydrogen (a), or represents one of the groups

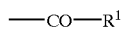 (b)

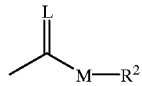 (c)

 (d)

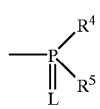 (e)

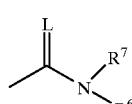 (f)

or

E (g)

E represents a metal ion equivalent or an ammonium ion,

L represents oxygen or sulphur,

M represents oxygen or sulphur, $R^1$ represents alkyl, alkenyl, alkoxyalkyl, alkylthioalkyl or polyalkoxyallyl, in each case optionally substituted once or several times in an identical or different manner by halogen, or optionally substituted, saturated or unsaturated cycloalkyl, which may be interrupted by at least one heteroatom, or represents in each case optionally substituted phenyl, phenylalkyl, hetaryl phenoxyalkyl or hetaryloxyalkyl, $R^2$ represents alkyl, alkenyl, alkoxyalkyl or polyalkoxyalkyl in each case optionally substituted once or several times in an identical or different manner by halogen, or in each case optionally substituted cycloalkyl, phenyl or benzyl, $R^3$ represents alkyl which is in each case optionally substituted once or several times in an identical or different manner by halogen, or represents in each case optionally substituted phenyl or phenylalkyl, $R^4$ and $R^5$ independently of one another represent alkyl, alkoxy, alkylamino, alkenylamino, dialkylamino, dialkenylamino, alkylthio, alkenylthio, alkenylthio or cycloalkylthio, in each case optionally substituted once or several times in an identical or different manner by halogen, or represent in each case optionally substituted phenyl, phenoxy or phenylthio, $R^6$ and $R^7$ independently of one another represent hydrogen or alkyl, alkenyl, alkoxy or alkoxyalkyl, in each case optionally substituted once or several times in an identical or different manner by halogen, or represent optionally substituted phenyl or represent optionally substituted benzyl, or $R^6$ and $R^7$ together represent an alkylene radical which is optionally interrupted by oxygen or sulphur, and the enantiomerically pure forms of compounds of the formula (I).

2. Compounds of the formula (I) according to claim 1, which, incorporating the various meanings (a), (b), (c), (d), (e), (f) and (g) of the group G, have following structures (Ia) to (Ig):

(Ia)
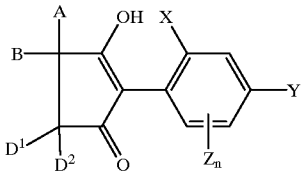

(Ib)
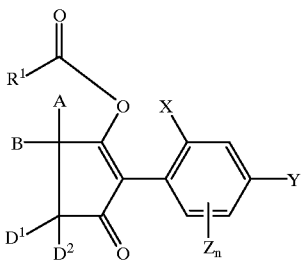

(Ic)
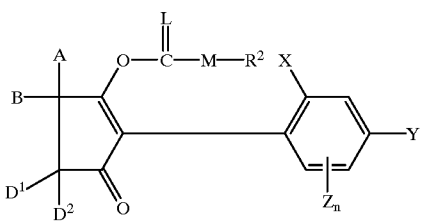

(Id)
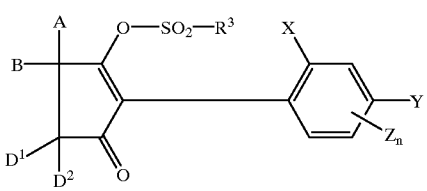

(Ie)
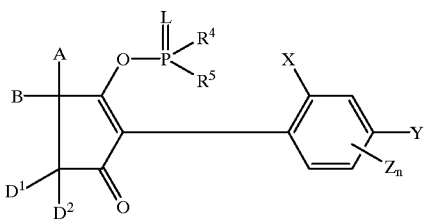

(If)
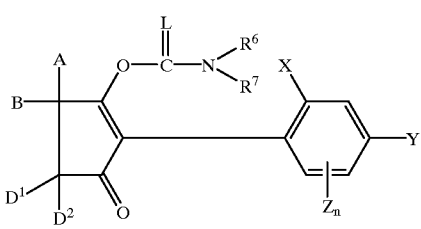

(Ig)
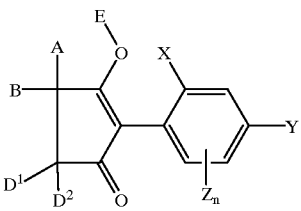

wherein

A, B, $D^1$, $D^2$, E, L, M, X, Y, Z, $R^1$, $R^2$, $R^3$, $R^4$, $R^5$, $R^6$, $R^7$ and n have the meanings given in claim 1.

3. Compounds of the formula (I) according to claim 1, in which

X represents halogen, nitro, cyano, $C_1$–$C_6$-alkyl, $C_1$–$C_6$-alkoxy, $C_3$–$C_6$-alkenyloxy, $C_1$–$C_6$-alkylthio, $C_1$–$C_6$-alkylsulphinyl, $C_1$–$C_6$-alkylsulphonyl, $C_1$–$C_3$-halogenoalkyl or $C_1$–$C_3$-halogenoalkoxy, Y represents hydrogen, halogen, nitro, cyano, $C_1$–$C_6$-alkyl $C_1$–$C_6$-alkoxy, $C_3$–$C_6$-alkenyloxy, $C_1$–$C_6$-alkylthio, $C_1$–$C_6$-alkylsulphinyl, $C_1$–$C_6$-alkylsulphonyl, $C_1$–$C_3$-halogenoalkyl or $C_1$–$C_3$-halogenoalkoxy, Z represents halogen, nitro, cyano, $C_1$–$C_6$-alkyl, $C_1$–$C_6$alkoxy or $C_1$–$C_3$-halogenoalkoxy, n represents 0, 1, 2 or 3, or the radicals X and Z, together with the phenyl radical to which they are bonded, represent the naphthalene radical of the formula

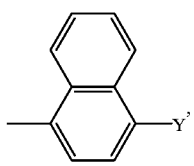

in which

Y has the abovementioned meaning,

A and B independently of one another represent $C_1$–$C_{12}$-alkyl, $C_3$–$C_8$-alkenyl, $C_3$–$C_8$-alkinyl, $C_1$–$C_{10}$-alkoxy-$C_1$–$C_8$-alkyl, poly-$C_1$–$C_8$-alkoxy-$C_1$–$C_8$-alkyl or $C_1$–$C_{10}$-alkylthio-$C_{1-8}$-alkyl, in each case optionally substituted once or several times in an identical or different manner by halogen, or saturated or unsaturated cycloalkyl which has 3 to 8 ring atoms, is optionally substituted once or several times in an identical or different manner by halogen, $C_1$–$C_6$-alkyl or $C_1$–$C_6$-alkoxy and in which at least one methylene group is optionally replaced by oxygen and/or sulphur, or phenyl or phenyl-$C_1$–$C_6$-alkyl, in each case optionally substituted once or several times in an identical or different manner by halogen, $C_1$–$C_6$-alkyl, $C_1$–$C_6$-halogenoalkyl, $C_1$–$C_6$-alkoxy, $C_1$–$C_6$-halogenoalkoxy, cyano or nitro, or A and B, together with the carbon atom to which they are bonded, form a saturated or unsaturated 3- to 8-membered ring which optionally comprises oxygen and/or sulphur and is optionally substituted once or several times in an identical or different manner by halogen, $C_1$–$C_6$-alkyl, $C_1$–$C_6$-alkoxy, $C_1$–$C_4$-halogenoalkyl, $C_1$–$C_4$-halogenoalkoxy, $C_1$–$C_4$-alkylthio or phenyl which is optionally substituted by halogen, $C_1$–$C_6$-alkyl or $C_1$–$C_6$-alkoxy, or A and B, together with the carbon atom to which they are bonded, represent $C_3$–$C_8$-cycloalkyl, in which two substituents, together with the carbon atoms to which they are bonded, represent a saturated or unsaturated 5- to 7-membered ring which is optionally substituted once or several times in an identical or different manner by halogen, $C_1$–$C_6$alkyl, $C_1$–$C_6$-alkoxy and may comprise oxygen or sulphur, $D^1$ and $D^2$ independently of one another represent hydrogen, halogen or $C_1$–$C_6$-alkyl which is optionally substituted once or several times in an identical or different manner by halogen, or represent phenyl which is optionally substituted once or several times in an identical or different manner by halogen, $C_1$–$C_6$-alkyl, $C_1$–$C_6$-alkoxy, nitro, $C_1$–$C_6$-halogenoalkyl or $C_1$–$C_6$-halogenoalkoxy, G represents hydrogen (a), or represents one of the groups (b)
$$-CO-R^1$$

(c)
$$\overset{L}{\underset{M-R^2}{\|}}$$

(d)
$$-SO_2-R^3$$

(e)
$$\overset{R^4}{\underset{L}{\overset{\|}{P}}}_{R^5}$$

(f)
$$\overset{L}{\underset{N}{\|}}\overset{R^7}{\underset{R^6}{}}$$

or (g)
E in which

E represents a metal ion equivalent or an ammonium ion,

L represents oxygen or sulphur,

M represents oxygen or sulphur, $R^1$ represents $C_1$–$C_{20}$-alkyl, $C_2$–$C_{20}$-alkenyl, $C_1$–$C_8$-alkoxy-$C_1$–$C_8$-alkyl $C_1$–$C_8$-alkylthio-$C_1$–$C_8$-alkyl or poly-$C_1$–$C_8$-alkoxy-$C_2$–$C_8$-alkyl, in each case optionally substituted once or several times in an identical or different manner by halogen, or saturated or unsaturated cycloalkyl having 3 to 8 ring atoms, which is optionally substituted once or several times in an identical or different manner by halogen, $C_1$–$C_6$-alkyl or $C_1$–$C_6$-alkoxy and in which at least one methylene group may be replaced by an oxygen and/or sulphur atom, or represents phenyl which is optionally substituted once or several times in an identical or different manner by halogen, nitro, cyano, $C_1$–$C_6$-alkyl, $C_1$–$C_6$-alkoxy, $C_1$–$C_6$-halogenoalkyl or $C_1$–$C_6$-halogenoalkoxy, or represents phenyl-$C_1$–$C_6$-alkyl which is optionally substituted once or several times in an identical or different manner by halogen, $C_1$–$C_6$-alkyl, $C_1$–$C_6$-alkoxy, $C_1$–$C_6$-halogenoalkyl or $C_1$–$C_6$-halogenoalkoxy, or represents hetaryl which has 5 or 6 ring atoms and is optionally substituted once or several times in an identical or different manner by halogen or $C_1$–$C_6$-alkyl, or represents phenoxy-$C_1$–$C_6$-alkyl which is optionally substituted once or several times in an identical or different manner by halogen or $C_1$–$C_6$-alkyl, or represents hetaryloxy-$C_1$–$C_6$-alkyl which has 5 or 6 ring atoms and is optionally substituted once or several times in an identical or different manner by halogen, amino or $C_1$–$C_6$-alkyl, $R^2$ represents $C_1$–$C_{20}$-alkyl, $C_2$–$C_{20}$-alkenyl, $C_1$–$C_8$-alkoxy-$C_2$–$C_8$-alkyl or poly-$C_1$–$C_8$-alkoxy-$C_2$–$C_8$-alkyl, in each case optionally substituted once or several times in an identical or different manner by halogen, or represents $C_3$–$C_8$-cycloalkyl which is optionally substituted once or several times in an identical or different manner by halogen, $C_1$–$C_6$-alkyl or $C_1$–$C_6$-alkoxy, or represents phenyl or benzyl, in each case optionally substituted once or several times in an identical or different manner by halogen, nitro, cyano, $C_1$–$C_6$-alkyl, $C_1$–$C_6$-alkoxy or $C_1$–$C_6$-halogenoalkyl, $R^3$ represents $C_1$–$C_{12}$-alkyl which is in each case optionally substituted once or several times in an identical or different manner by halogen, or represents phenyl or phenyl-$C_1$–$C_4$-alkyl, in each case optionally substituted once or several times in an identical or different manner by halogen, $C_1$–$C_6$-alkyl, $C_1$–$C_6$-alkoxy, $C_1$–$C_3$-halogenoalkyl, $C_1$–$C_3$-halogenoalkoxy, cyano or nitro, $R^4$ and $R^5$ independently of one another represent $C_1$–$C_8$-alkyl, $C_1$–$C_8$-alkoxy, $C_1$–$C_8$-alkylamino, $C_3$–$C_5$-alkenylamino, di-($C_1$–$C_8$-alkyl)-amino, di-($C_3$–$C_8$-alkenyl)-amino, $C_1$–$C_8$-alkylthio, $C_3$–$C_5$-alkenylthio, $C_3$–$C_5$-alkinylthio or $C_3$–$C_7$-cycloalkylthio, in each case optionally substituted once or several times in an identical or different manner by halogen, or represent phenyl, phenoxy or phenylthio, in each case optionally substituted once or several times in an identical or different manner by halogen, nitro, cyano, $C_1$–$C_4$-alkoxy, $C_1$–$C_4$-halogenoalkoxy, $C_1$–$C_4$-alkylthio, $C_1$-$C_4$-halogenoalkylthio, $C_1$–$C_4$-alkyl or $C_1$–$C_4$-halogenoalkyl and $R^6$ and $R^7$ independently of one another represent hydrogen, or represent $C_1$–$C_{10}$-alkyl, $C_1$–$C_{10}$-alkoxy, $C_3$–$C_8$-alkenyl or $C_1$–$C_{10}$-alkoxy-$C_1$–$C_{10}$-alkyl, in each case optionally substituted once or several times in an identical or different manner by halogen, or represent phenyl which is optionally substituted once or several times in an identical or different manner by halogen, $C_1$–$C_3$-halogenoalkyl $C_1$–$C_8$-alkyl or $C_1$–$C_8$-alkoxy, or represent benzyl which is optionally substituted once or several times in an identical or different manner by halogen, $C_1$–$C_8$-alkyl, $C_1$–$C_8$-halogenoalkyl or $C_1$–$C_8$-alkoxy, or together represent a $C_2$–$C_6$-alkylene radical, in which a methylene group may be replaced by oxygen or sulphur and the enantiomerically pure forms of compounds of the formula (I).

4. Compounds of the formula (I) according to claim 1, in which

X represents fluorine, chlorine, bromine, nitro, cyano, $C_1$–$C_4$-alkyl, $C_1$–$C_4$-alkoxy, $C_1$–$C_2$-halogenoalkyl or $C_1$–$C_2$-halogenoalkoxy, Y represents hydrogen, fluorine, chlorine, bromine, nitro, cyano, $C_1$–$C_6$-alkyl, $C_1$–$C_6$-alkoxy, $C_1$–$C_2$-halogenoalkyl or $C_1$–$C_2$-halogenoalkoxy, Z represents fluorine, chlorine, bromine, nitro, cyano, $C_1$–$C_4$-alkyl, $C_1$–$C_4$-alkoxy or $C_1$–$C_2$-halogenoalkoxy, n represents 0, 1 or 2, A and B independently of one another represent $C_1$–$C_{10}$-alkyl $C_3$–$C_6$-alkenyl, $C_3$–$C_6$-alkinyl, $C_1$–$C_8$-alkoxy-$C_1$–$C_6$-alkyl, poly-$C_1$–$C_6$-alkoxy-$C_1$–$C_6$-alkyl, $C_1$–$C_8$-alkylthio-$C_1$–$C_6$-alkyl, in each case optionally substituted once to five times in an identical or different manner by fluorine or chlorine, or saturated or unsaturated cycloalkyl which has 3 to 7 ring atoms, is optionally substituted once to three times in an identical or different manner by fluorine, chlorine, $C_1$–$C_4$-alkyl or $C_1$–$C_4$-alkoxy, and in which one or two methylene groups are optionally replaced by oxygen and/or sulphur atoms, or phenyl or phenyl-$C_1$–$C_4$-alkyl, in each case optionally substituted once to three times in an identical or different manner by fluorine, chlorine, bromine, $C_1$–$C_4$-alkyl, $C_1$–$C_4$-halogenoalkyl, $C_1$–$C_4$-alkoxy, cyano or nitro, or A and B, together with the carbon atom to which they are bonded, form a saturated or unsaturated 3 to 7-membered ring which optionally comprises oxygen and/or sulphur and is optionally substituted once to three times in an identical or different manner by fluorine, chlorine, $C_1$–$C_5$-alkyl, $C_1$–$C_5$-alkoxy, $C_1$–$C_3$-halogenoalkyl, $C_1$–$C_4$-halogenoalkoxy, $C_1$–$C_3$-alkylthio or phenyl which is optionally substituted once or several times in an identical or different manner by fluorine, chlorine, bromine, $C_1$–$C_4$-alkyl or $C_1$–$C_4$-alkoxy, or A and B, together with the carbon atom to which they are bonded, represent $C_4$–$C_7$-cycloalkyl, in which two substituents, together with the carbon atoms to which they are bonded, represent a saturated or unsaturated 5- or 6-membered ring which is optionally substituted once to three times in an identical or different manner by fluorine, chlorine, $G_1$–$C_3$-alkyl or $C_1$–$C_3$-alkoxy and may comprise oxygen or sulphur, $D^1$ and $D^2$ independently of one another represent hydrogen, fluorine, chlorine or $C_1$–$C_4$-alkyl which is optionally substituted once to five times in an identical or different manner by fluorine or chlorine, or represent phenyl which is optionally substituted once to three times in an identical or different manner by fluorine, chlorine, bromine, $C_1$–$C_4$-alkyl, $C_1$–$C_4$-alkoxy, nitro, $C_1$–$C_2$-halogenoalkyl or $C_1$–$C_2$-halogenoalkoxy, G represents hydrogen (a), or represents one of the groups (b)

—CO—$R^1$ (c)

(d)

—$SO_2$—$R^3$ (e)

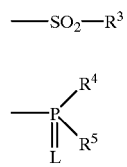

(f)

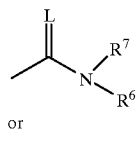

or (g)

E in which

E represents a metal ion equivalent or an ammonium ion,

L represents oxygen or sulphur,

M represents oxygen or sulphur, $R^1$ represents $C_1$–$C_{16}$-alkyl, $C_2$–$C_{16}$-alkenyl, $C_1$–$C_6$-alkoxy-$C_1$–$C_6$-alkyl, $C_1$–$C_6$-alkylthio-$C_1$–$C_6$-alkyl or poly-$C_1$–$C_6$-alkoxy-$C_2$–$C_6$-alkyl, in each case optionally substituted once to nine times in an identical or different manner by halogen, or cycloalkyl which has 3 to 7 ring atoms, is optionally substituted once or six times in an identical or different manner by fluorine, chlorine, $C_1$–$C_4$-alkyl or $C_1$–$C_4$-alkoxy, and in which one or two methylene groups are optionally replaced by oxygen and/or sulphur atoms, or represents phenyl which is optionally substituted once to three times in an identical or different manner by fluorine, chlorine, bromine, nitro, cyano, $C_1$–$C_4$-alkyl, $C_1$–$C_4$-alkoxy, $C_1$–$C_3$-halogenoalkyl or $C_1$–$C_3$-halogenoalkoxy, or represents phenyl-$C_1$–$C_4$-alkyl which is optionally substituted once to three times in an identical or different manner by fluorine, chlorine, bromine, $C_1$–$C_4$-alkyl $C_1$–$C_4$-alkoxy, $C_1$–$C_3$-halogenoalkyl or $C_1$–$C_3$-halogenoalkoxy, or represents pyridyl, thienyl, furanyl, pyrimidyl, thiazolyl or pyrazolyl, in each case optionally substituted once or twice in an identical or different manner by fluorine, chlorine or $C_1$–$C_6$-alkyl, or represents phenoxy-$C_1$–$C_5$-alkyl which is optionally substituted once to three times in an identical or different manner by fluorine, chlorine, bromine or $C_1$–$C_4$-alkyl, or represents pyridyloxy-$C_1$–$C_5$-alkyl, pyrimidyloxy-$C^1$–$C_5$-alkyl or thiazolyloxy-$C_1$–$C_5$-alkyl, in each case optionally substituted once or twice in an identical or different manner by fluorine, chlorine, bromine, amino or $C_1$–$C_4$-alkyl, $R^2$ represents $C_1$–$C_{16}$alkyl, $C_2$–$C_{16}$-alkenyl, $C_1$–$C_6$-alkoxy-$C_2$–$C_6$-alkyl or poly-$C_1$–$C_6$-alkoxy-$C_2$–$C_6$-alkyl, in each case optionally substituted once to nine times in an identical or different manner by fluorine or chlorine, or represents $C_3$–$C_7$-cycloalkyl which is optionally substituted once to five times in an identical or different manner by fluorine, chlorine, $C_1$–$C_4$-alkyl or $C_1$–$C_4$-alkoxy, or represents phenyl or benzyl, in each case optionally substituted once to three times in an identical or different manner by fluorine, chlorine, bromine, nitro, cyano, $C_1–C_4$-alkyl, $C_1–C_3$-alkoxy or $C_1–C_3$-halogenoalkyl, $R^3$ represents $C_1–C_8$-alkyl which is in each case optionally substituted once to five times in an identical or different manner by fluorine or chlorine, or represents phenyl or phenyl-$C_1–C_2$-alkyl, in each case optionally substituted once to three times in an identical or different manner by fluorine, chlorine, bromine, $C_1–C_4$-alkyl, $C_1–C_4$-alkoxy, $C_1–C_2$-halogenoalkyl, $C_1–C_2$-halogenoalkoxy, cyano or nitro, $R^4$ and $R^5$ independently of one another represent $C_1–C_6$-alkyl, $C_1–C_6$-alkoxy, $C_1–C_6$-alkylamino, $C_3–C_6$-alkenylamino, di-($C_1–C_6$-alkyl)-amino, di-($C_3–C_6$-alkenyl)-amino, $C_1–C_6$-alkylthio, $C_3–C_4$-alkenylthio, $C_3–C_4$-alkinylthio or $C_3–C_6$cycloalkylthio, in each case optionally substituted once to five times in an identical or different manner by fluorine or chlorine, or represent phenyl, phenoxy or phenylthio, in each case optionally substituted once to three times in an identical or different manner by fluorine, chlorine, bromine, nitro, cyano, $C_1–C_3$-alkoxy, $C_1–C_3$-halogenoalkoxy, $C_1–C_3$-alkylthio, $C_1–C_3$-halogenoalkylthio, $C_1–C_3$-alkyl or $C_1–C_3$-halogenoalkyl and $R^6$ and $R^7$ independently of one another represent hydrogen, or represent $C_1–C_6$-alkyl, $C_1–C_6$-alkoxy, $C_3–C_6$-alkenyl or $C_1–C_6$-alkoxy-$C_1–C_6$-alkyl, in each case optionally substituted once to five times in an identical or different manner by fluorine or chlorine, or represent phenyl which is optionally substituted once to three times in an identical or different manner by fluorine, chlorine, $C_1–C_3$-halogenoalkyl, $C_1–C_3$-alkyl or $C_1–C_3$-alkoxy, or represent benzyl which is optionally substituted once to five times in an identical or different manner by fluorine, chlorine, $C_1–C_3$-alkyl, $C_1–C_3$-halogenoalkyl or $C_1–C_3$-alkoxy, or together represent a $C_4C_6$-alkylene radical, in which a methylene group may be replaced by oxygen or sulphur, and the enantiomerically pure forms of compounds of the formula (I).

5. Compounds of the formula (I) according to claim 1, in which

X represents fluorine, chlorine, bromine, nitro, cyano, methyl ethyl, n-propyl, i-propyl, methoxy, ethoxy, tirfuoromethyl, trifluoromethoxy, difluoromethoxy or chlorodifluoromethoxy, Y represents hydrogen, fluorine, chlorine, bromine, nitro, cyano, methyl, ethyl, n-propyl, i-propyl, n-butyl, i-butyl, tert-butyl, methoxy, ethoxy, trifluoromethyl trifluoromethoxy, difluoromethoxy or chlorodifluoromethoxy, Z represents fluorine, chlorine, bromine, nitro, cyano, methyl ethyl n-propyl, i-propyl, n-butyl, i-butyl, tert-butyl, methoxy, ethoxy, trifluoromethoxy, difluoromethoxy or chlorodifluoromethoxy, n represents 0 or 1, A and B independently of one another represent $C_1–C_8$-alkyl $C_3–C_4$-alkenyl, $C_3–C_4$-alkinyl, $C_1–C_6$-alkoxy-$C_1–C_4$-alkyl, poly-$C_1–C_4$-alkoxy-$C_1–C_4$-alkyl or $C_1–C_6$-alkylthio-$C_1–C_4$-alkyl, in each case optionally substituted once to three times in an identical or different manner by fluorine or chlorine, or cycloalkyl which has 3 to 6 ring atoms, is optionally substituted once or twice in an identical or different manner by fluorine, chlorine, methyl ethyl, methoxy or ethoxy, and in which one or two methylene groups are optionally replaced by oxygen and/or sulphur atoms, or phenyl or benzyl, in each case optionally substituted once or twice in an identical or different manner by fluorine, chlorine, methyl, ethyl, propyl, iso-propyl, methoxy, ethoxy, trifluoromethyl, cyano or nitro, or A and B, together with the carbon atom to which they are bonded, form a saturated or unsaturated 3- to 6-membered ring which optionally comprises oxygen and/or sulphur and is optionally substituted once or twice in an identical or different manner by fluorine, chlorine, $C_1–C_4$-alkyl, $C_1–C_4$-alkoxy, trifluoromethyl, $C_1–C_2$-alkylthio or phenyl which is optionally substituted once or twice in an identical or different manner by fluorine, chlorine, methyl or methoxy, or A and B, together with the carbon atom to which they are bonded, represent $C_5–C_6$-cycloalkyl, in which two substituents, together with the carbon atoms to which they are bonded, represent a salted or unsaturated 5- or 6-membered ring which is optionally substituted once or twice in an identical or different manner by fluorine, chlorine, methyl, ethyl, methoxy or ethoxy and may comprise oxygen or sulphur, $D^1$ and $D^2$ independently of one another represent hydrogen, fluorine, chlorine, methyl or ethyl, or represent phenyl which is optionally substituted once or twice in an identical or different manner by fluorine, chlorine, methyl, methoxy or trifluoromethyl, G represents hydrogen (a), or represents one of the groups (b)

(c)
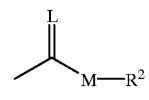

(d)
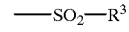

(e)
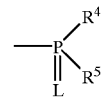

(f)
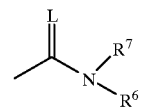

or (g)

E in which

E represents a metal ion equivalent or an ammonium ion,

L represents oxygen or sulphur,

M represents oxygen or sulphur, $R^1$ represents $C_1–C_{14}$-alkyl, $C_2–C_{14}$-alkenyl, $C_1–C_4$-alkoxy-$C_1–C_6$-alkyl, $C_1–C_4$-alkylthio-$C_1–C_6$-alkyl or poly-$C_1–C_4$-alkoxy-$C_1–C_4$-alkyl in each case optionally substituted once to three times in an identical or different manner by fluorine or chlorine, or cycloalkyl which has 3 to 6 ring atoms, is optionally substituted once or twice in an identical or different manner by fluorine, chlorine, methyl, ethyl, methoxy or ethoxy, and in which one or two methylene groups are optionally replaced by oxygen and/or sulphur atoms, or represents phenyl which is optionally substituted once or twice in an identical or different manner by fluorine, chlorine, bromine, methyl, ethyl, propyl, i-propyl, methoxy, ethoxy, trifluoromethyl, trifluoromethoxy, cyano or nitro, or represents phenyl-$C_1$–$C_3$-alkyl, in particular benzyl, which is optionally substituted once or twice in an identical or different manner by fluorine, chlorine, bromine, methyl, ethyl, propyl, i-propyl, methoxy, ethoxy, trifluoromethyl or trifluoromethoxy, or represents pyridyl, thienyl or furanyl, in each case optionally substituted once or twice in an identical or different manner by fluorine, chlorine, bromine, methyl or ethyl, or represents phenoxy-$C_1$–$C_4$-alkyl which is optionally substituted once or twice in an identical or different manner by fluorine, chlorine, methyl or ethyl or represents pyridyloxy-$C_1$--alkyl, pyrimidyloxy-$C_1$–$C_3$-akyl or thiazolyloxy-$C_1$–$C_3$-alkyl, in each case optionally substituted once or twice in an identical or different manner by fluorine, chlorine, amino, methyl or ethyl, $R^2$ represents $C_1$–$C_{14}$-alkyl, $C_2$–$C_{14}$-alkenyl, $C_{1-4}$-alkoxy-$C_{26}$-akyl or poly-$C_1$–$C_4$-alkoxy-$C_2$–$C_6$-alkyl, in each case optionally substituted once to five times in an identical or different manner by fluorine or chlorine, or represents $C_3$–$C_6$-cycloalkyl which is optionally substituted once to three times in an identical or different manner by fluorine, chlorine, methyl, ethyl, methoxy or ethoxy, or represents phenyl or benzyl, in each case optionally substituted once or twice in an identical or different manner by fluorine, chlorine, nitro, cyano, methyl, ethyl, propyl, i-propyl, methoxy, ethoxy or trifluoromethyl, $R^3$ represents $C_1$–$C_6$-alkyl which is optionally substituted once to three times in an identical or different manner by fluorine or chlorine, or represents phenyl or benzyl, in each case optionally substituted once or twice in an identical or different manner by fluorine, chlorine, bromine, methyl, methoxy, trifuoromethyl trifluoromethoxy, cyano or nitro, $R^4$ and $R^5$ independently of one another represent $C_1$–$C_4$-alkyl, $C_1$–$C_4$-alkoxy, $C_1$–$C_4$-alkylamino, $C_3$–$C_4$-alkenylamino, di-($C_1$-$C_4$-alkyl)-amino, di-($C_3$-$C_4$-alkenyl)-amino, $C_1$–$C_4$-alkylthio, in each case optionally substituted once to three times in an identical or different manner by fluorine or chlorine, or represent phenyl, phenoxy or phenylthio, in each case optionally substituted once or twice in an identical or different manner by fluorine, chlorine, bromine, nitro, cyano, $C_1$–$C_2$-alkoxy, $C_1$–$C_2$-fluoroalkoxy, $C_1$–$C_2$-chloroalkoxy, $C_1$–$C_2$-alkylthio, $C_1$–$C_2$-fluoroalkylthio, $C_1$–$C_2$-chloroalkylthio or $C_1$–$C_3$-alkyl, $R^6$ and $R^7$ independently of one another represent hydrogen, or represent $C_1$–$C_4$-alkyl, $C_1$–$C_4$-alkoxy or $C_1$–$C_4$-alkoxy-$C_1$–$C_4$-alkyl in each case optionally substituted once to three times in an identical or different manner by fluorine or chlorine, or represent phenyl which is optionally substituted once or twice in an identical or different manner by fluorine, chlorine, $C_1$–$C_2$-halogenoalkyl, $C_1$–$C_2$-alkyl or $C_1$–$C_2$-alkoxy, or represent benzyl which is optionally substituted once or twice in an identical or different manner by fluorine, chlorine, bromine, $C_1$–$C_2$-alkyl, $C_1$–$C_2$-halogenoalkyl or $C_1$–$C_2$-alkoxy, or together represent a $C_4$–$C_6$-alkylene radical, in which a methylene group may be replaced by oxygen or sulphur, and the enantiomerically pure forms of compounds of the formula (I).

6. Process for the preparation of compounds of the formula (I) according to claim 1, wherein (A) to prepare compounds of the formula (Ia)

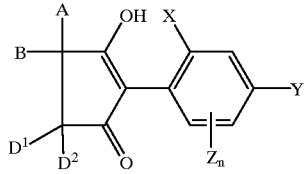

(Ia)

in which

A, B, $D^1$, $D^2$, X, Y, Z and n have the meaning given in claim 1, ketocarboxylic acid esters of the formula (II)

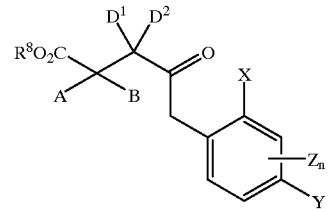

(II)

in which

A, B, $D^1$, $D^2$, X, Y, Z and n have the abovementioned meaning and $R^8$ represents alkyl, are subjected to intermolecular cyclization, optionally in the presence of a diluent and in the presence of a base, and (B) to prepare compounds of the formula (Ib)

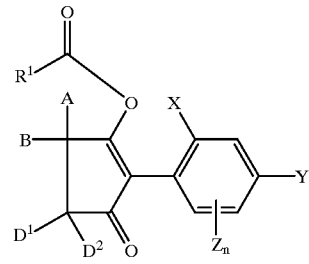

(Ib)

in which

A, B, $D^1$, $D^2$, X, Y, Z, $R^1$ and n have the meaning given in claim 1, compounds of the formula (Ia)

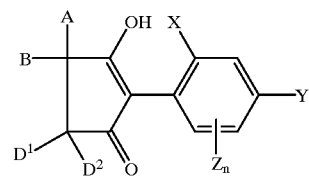

(Ia)

in which

A, B, $D^1$, $D^2$, X, Y, Z and n have the abovementioned meaning,

α) are reacted with acid halides of the formula (III)

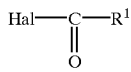 (III)

in which

R¹ has the abovementioned meaning and

Hal represents halogen, optionally in the presence of a diluent and optionally in the presence of an acid-binding agent, or β) are reacted with carboxylic acid anhydrides of the formula (IV)

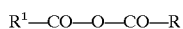 (IV)

in which

R¹ has the abovementioned meaning, optionally in the presence of a diluent and optionally in the presence of an acid-binding agent, and (C) to prepare compounds of the formula (Ic)

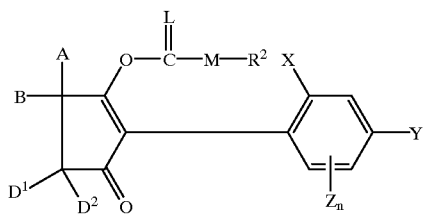 (Ic)

in which

A, B, D¹, D², X, Y, Z, R² and n have the meaning given in claim 1,

L represents oxygen and

M represents oxygen or sulphur, compounds of the formula (Ia)

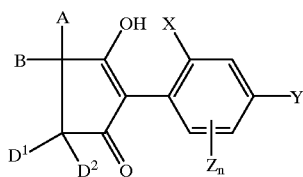 (Ia)

in which

A, B, D¹, D², X, Y, Z and n have the abovementioned meaning, are reacted with a chloroformic acid ester or chloroformic acid thiol ester of the formula (V)

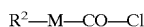 (V)

in which

R² and M have the abovementioned meaning, optionally in the presence of a diluent and optionally in the presence of an acid-binding agent, and (D) to prepare compounds of the formula (Ic)

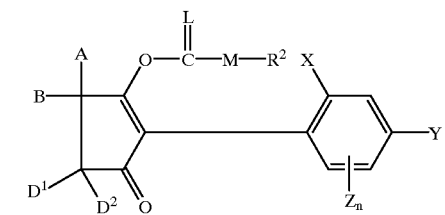 (Ic)

in which

A, B, D¹, D², R², X, Y, Z and n have the abovementioned meaning,

L represents sulphur and

M represents oxygen or sulphur, compounds of the formula (Ia)

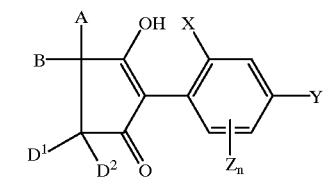 (Ia)

in which

A, B, D¹, D², X, Y, Z and n have the abovementioned meaning,

α) are reacted with a chloromonothioformic acid ester or chlorodithioformic acid ester of the formula (VI)

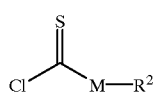 (VI)

in which

M and R² have the abovementioned meaning, optionally in the presence of a diluent and optionally in the presence of an acid-binding agent, or β) are reacted with carbon disulphide and then with alkyl halides of the formula (VI)

 (VII)

in which

R² has the abovementioned meaning and

Hal represents chlorine, bromine or iodine, optionally in the presence of a diluent and optionally in the presence of a base, and (E) to prepare compounds of the formula (Id)

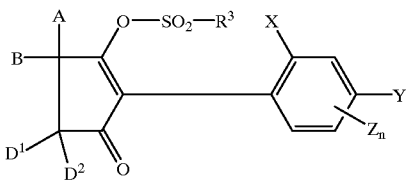

in which

A, B, $D^1$, $D^2$, X, Y, Z, $R^3$ and n have the meaning given in claim 1, compounds of the formula (Ia)

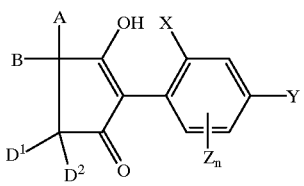

in which

A, B, $D^1$, $D^2$, X, Y, Z and n have the abovementioned meaning, are reacted with sulphonic acid chlorides of the formula (VIII)

in which $R^3$ has the abovementioned meaning, optionally in the presence of a diluent and optionally in the presence of an acid-binding agent, and (F) to prepare compounds of the formula (Ie)

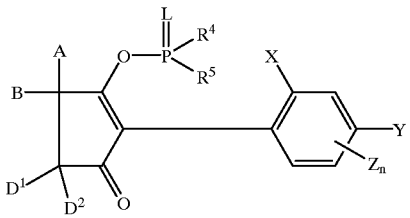

in which

A, B, $D^1$, $D^2$, L, X, Y, Z, $R^4$, $R^5$ and n have the meaning given in claim 1, compounds of the formula (Ia)

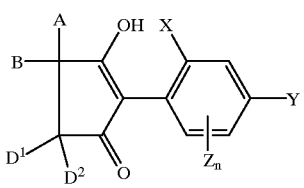

in which

A, B, $D^1$, $D^2$, X, Y, Z and n have the abovementioned meaning, are reacted with phosphorus compounds of the formula (IX)

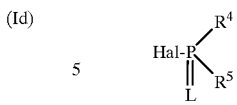

in which

L, $R^4$ and $R^5$ have the abovementioned meaning and

Hal represents halogen, optionally in the presence of a diluent and optionally in the presence of an acid-binding agent, and (G) to prepare compounds of the formula (If)

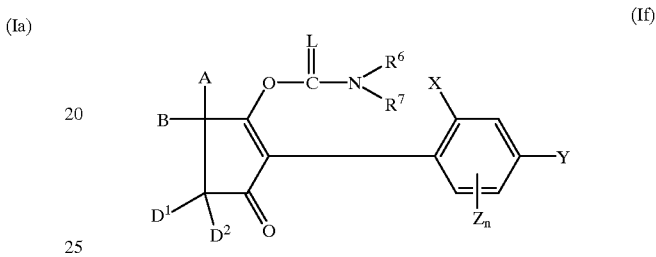

in which

A, B, $D^1$, $D^2$, L, X, Y, Z, $R^6$, $R^7$ and n have the meaning given in claim 1, compounds of the formula (Ia)

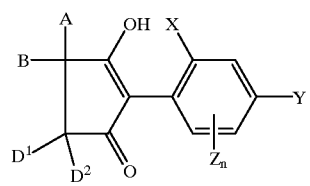

in which

A, B, $D^1$, $D^2$, X, Y, Z and n have the abovementioned meaning,

α) are reacted with isocyanates or isothiocyanates of the formula (X)

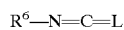

in which $R^6$ and L have the abovementioned meaning, optionally in the presence of a diluent and optionally in the presence of a catalyst, or β) are reacted with carbamic acid chlorides or thiocarbamic acid chlorides of the formula (XI)

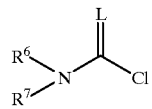

in which

L, $R^6$ and $R^7$ have the abovementioned meaning, optionally in the presence of a diluent and optionally in the presence of an acid-binding agent, and (H) to prepare compounds of the formula (Ig)

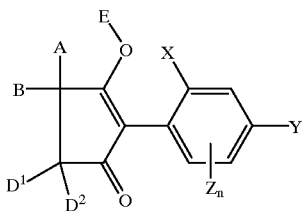
(Ig)

in which

X, Y, $D^1$, $D^2$, Z, A, B and n have the abovementioned meaning and

E represents a metal ion equivalent or an ammonium ion, compounds of the formula (Ia)

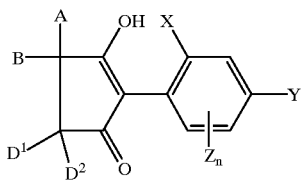
(Ia)

in which

X. Y, Z, A, B, $D^1$, $D^2$ and n have the abovementioned meaning, are reacted with metal compounds of the formula (XII) or amines of the formula (XIII)

$MeR^9_s$      (XII)

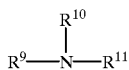
(XIII)

in which

Me represents mono- or divalent metal ions and t represents the number 1 or 2 and $R^9$, $R^{10}$ and $R^{11}$ independently of one another represent hydrogen, alkyl, alkoxy or hydroxyl, optionally in the presence of a diluent.

7. Compounds of the formula (II)

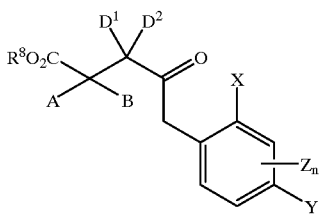
(II)

in which

A, B, $D^1$, $D^2$, X, Y, Z and n have the meaning given in claim 1 and $R^8$ represents alkyl.

8. Process for the preparation of compounds of the formula (II) according to claim 7, wherein compounds of the formula (XIV)

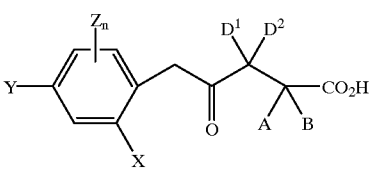
(XIV)

in which

X, Y, Z, A, B, $D^1$, $D^2$ and n have the meaning given in claim 1, are esterified.

9. Compounds of the formula (XIV)

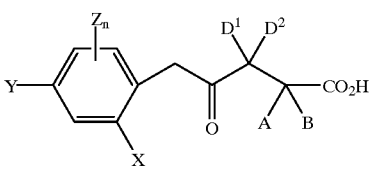
(XIV)

in which

A, B, $D^1$, $D^2$, X, Y, Z and n have the meaning given in claim 1.

10. Process for the preparation of compounds of the formula (XIV) according to claim 9, wherein either carboxylic acid anhydrides of the formula (XV)

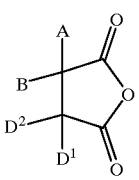
(XV)

in which

A, B and D have the abovementioned meaning, are reacted with organometallic compounds of the formula (XVI)

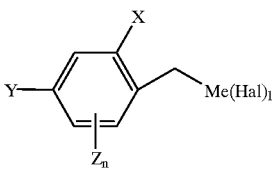
(XVI)

in which

X, Y, Z and n have the abovementioned meaning,

Me represents mono- or divalent metal ions,

Hal represents chlorine or bromine and

I represents the number 0 or 1, in the presence of a diluent, or compounds of the formula (XVII)

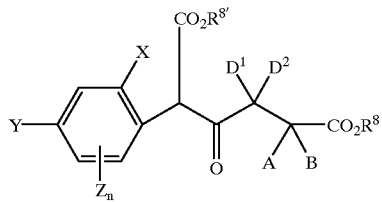

(XVII)

in which

A, B, $D^1$, $D^2$, X Y, Z and n have the abovementioned meaning and $R^8$ and $R^{8'}$ represent ally, are decarboxylated, optionally in the presence of a diluent and optionally in the presence of a base or acid.

11. An insecticidal composition comprising an insecticidally effective amount of a compound according to claim 1 and an extender.

12. A method of controlling unwanted insects which comprises administering to such insects or to a locus from which it is desired to exclude such insects an insecticidally effective amount of a compound according to claim 1.

13. An herbicidal composition comprising an herbicidally effective amount of a compound according to claim 1 and an extender.

14. A method of controlling unwanted vegetation which comprises applying to such vegetation or to a locus from which it is desired to exclude such vegetation an herbicidally effective amount of a compound according to claim 1.

* * * * *